United States Patent
Dally et al.

(10) Patent No.: US 8,217,032 B2
(45) Date of Patent: *Jul. 10, 2012

(54) SELECTIVE ESTROGEN RECEPTOR MODULATORS FOR THE TREATMENT OF VASOMOTOR SYMPTOMS

(75) Inventors: Robert Dean Dally, Indianapolis, IN (US); Jeffrey Alan Dodge, Indianapolis, IN (US); Scott Alan Frank, Indianapolis, IN (US); Ronald Jay Hinklin, Longmont, CO (US); Timothy Alan Shepherd, Indianapolis, IN (US); Owen Brendan Wallace, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/167,343

(22) Filed: Jun. 23, 2011

(65) Prior Publication Data

US 2011/0281847 A1   Nov. 17, 2011

Related U.S. Application Data

(63) Continuation of application No. 10/597,241, filed as application No. PCT/US2005/000020 on Jan. 18, 2005.

(60) Provisional application No. 60/538,342, filed on Jan. 22, 2004, provisional application No. 60/538,442, filed on Jan. 22, 2004.

(51) Int. Cl.
*A61P 15/12* (2006.01)
*A61K 31/4453* (2006.01)
*A61K 31/4523* (2006.01)
*A61K 31/55* (2006.01)
*C07D 295/08* (2006.01)
*C07D 311/78* (2006.01)
*C07D 335/04* (2006.01)
*C07D 221/18* (2006.01)

(52) U.S. Cl. ............ 514/217.03; 514/217.04; 514/284; 514/320; 514/324; 514/422; 540/596; 540/597; 546/61; 546/196; 546/202; 548/525

(58) Field of Classification Search ............ 514/217.03, 514/217.04, 284, 320, 324, 422; 540/596, 540/597; 546/61, 196, 202; 548/525
See application file for complete search history.

(56) References Cited

U.S. PATENT DOCUMENTS

| | | | |
|---|---|---|---|
| 5,567,712 A | 10/1996 | Palkowitz | |
| 5,726,186 A | 3/1998 | Grese | |
| 6,004,971 A | 12/1999 | Grese | |
| 6,133,288 A | 10/2000 | Grese | |

FOREIGN PATENT DOCUMENTS

| | | |
|---|---|---|
| EP | 0 761 669 | 3/1997 |
| EP | 0826 679 | 3/1998 |
| EP | 0 835 867 | 4/1998 |
| EP | 0 835 868 | 4/1998 |
| EP | 0 895 989 | 2/1999 |
| WO | 2004/009086 | 1/2004 |

OTHER PUBLICATIONS

Timothy A. Grese, et. al., Structure-Activity Relationships of Selective Estrogen Receptor Modulators: Modifications to the 2-Arylbenzothiophene Core of Raloxifene, J. Med. Chem. 1997, 40, 146-167, Lilly Research Laboratories, Eli Lilly and Company, Indianapolis, Indiana, USA.

*Primary Examiner* — Brenda Coleman

(74) *Attorney, Agent, or Firm* — Gilbert T. Voy

(57) ABSTRACT

The present invention relates to a selective estrogen receptor modulator of formula I or Ia: (I) (Ia); or a pharmaceutical acid addition salt thereof; useful for treating vasomotor symptoms, in particular hot flashes, night sweats and other symptoms that affect women around menopause.

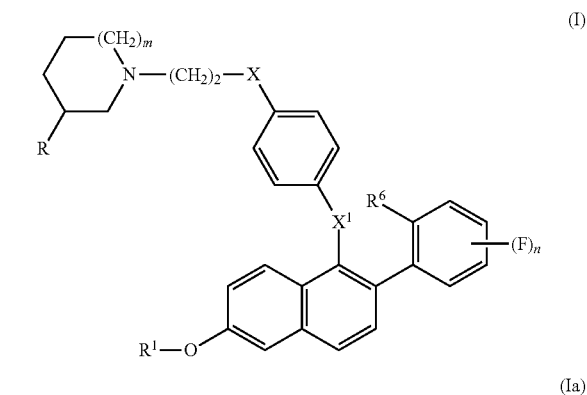

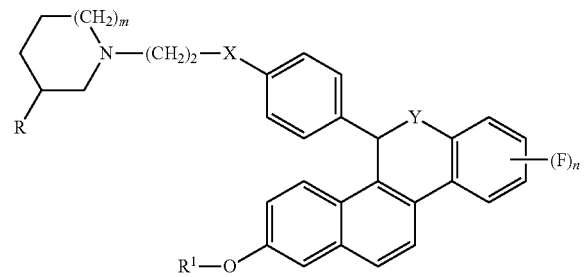

14 Claims, No Drawings

SELECTIVE ESTROGEN RECEPTOR MODULATORS FOR THE TREATMENT OF VASOMOTOR SYMPTOMS

This application is a continuation, and claims the benefit under 35 U.S.C. §120, of U.S. application Ser. No. 10/597,241 filed Jul. 18, 2006, which claims the benefit under 35 U.S.C. §120 of International Application No. PCT/US2005/000020 filed Jan. 18, 2005, which claims the benefit under 35 U.S.C. §119(e) of U.S. Ser. No. 60/538,342 filed Jan. 22, 2004 and U.S. Ser. No. 60/538,442 filed Jan. 22, 2004.

BACKGROUND OF THE INVENTION

"Vasomotor symptoms", i.e., hot flashes, night sweats, vaginal dryness, sleep disturbances, nausea and mood swings commonly affect women around menopause. In fact, a majority of postmenopausal women will experience vasomotor symptoms with a significant percentage of these women continuing to suffer symptoms for more than five years (Psychosom. Med. 1965, 27, 266; Med. Gynecol. Soc. 1969, 4, 268). Women who have undergone bilateral oophorectomy, radiotherapy or treatment with GnRH (gonadotropin releasing hormone) agonists are particularly prone to experiencing hot flashes (Br. J. Obstet. Gynaecol. 1977, 84, 769). Men have also been reported to experience vasomotor symptoms following treatment with a GnRH agonist (N. Engl. J. Med. 1981, 305, 663) or after orchidectomy (Urology 1980, 16, 620).

In spite of being identified as an ailment of menopause for hundreds of years, the precise mechanism underlying the cause of vasomotor symptoms is not clear. However, a link with declining estrogen levels (due to natural menopause or otherwise) is widely accepted. Interestingly, women with low estrogen levels due to ovarian dysgenesis generally do not suffer from vasomotor symptoms unless they are first given hormone replacement therapy (HRT) and then have it discontinued (Clin. Endocrinol. (Oxf) 1985, 22, 293), suggesting that estrogen withdrawal may be an underlying cause of vasomotor instability. HRT is currently a preferred standard treatment for vasomotor symptoms and is effective in >80% of women who initiate treatment, which again is supportive of an estrogenic role in the etiology thereof.

Hot flashes (flushes) are characterised by a warming sensation that begins in the chest and moves towards the neck and head, and are often accompanied by sweating, palpitations and cutaneous flashing. The episodes last from 30 seconds to 10 minutes. The hot flash event itself is thought to be centrally mediated resulting from a transient lowering of the thermoregulatory set point in the hypothalamus (for a review, see: Can. J. Physiol. Pharmacol. 1987, 65, 1312). Regulation of the thermoregulatory process may involve catecholamines, estrogen, testosterone, opioids and serotonin, among others (for a review, see: Mayo. Clin. Proc. 2002, 77, 1207). In fact, compounds that modulate the signaling pathway of each of these hormones/neurotransmitters have been evaluated for the treatment of hot flashes. See, e.g., Ann. Intern. Med. 2000, 132, 788; Br. Med. J. 1974, i, 409; Maturitas, 1978, 1, 21; Med. J. Aust. 1986, 144, 369; Fertil. Steel 1985, 43, 401; Br. J. Obstet. Gynaecol. 1981, 88, 919; J. Olin. Endocrinol. Metab. 1984, 58, 578; Clin. Endocrinol. 1985, 22, 293; Maturitas 2000, 36, 155; J. Clin. Oncol 2002, 20, 1583; JAMA 2003, 289, 2827; Lancet 2000, 356, 2059; N. Engl. J. Med. 1994, 331, 347; Obstet. Gynecol. 1984, 63, 1; Obstet. Gynecol. 1999, 94, 225; Br. J. Obstet. Gynecol. 1998, 105, 904; Neurology 2000, 54, 2161; Obstet. Gynecol. 1998, 72, 688; J. Chit Oncol. 1998, 16, 495; J. Clin. Oncol. 2001, 19, 2739; and J. Nutr. 2001, 131 (11, supl), 3095s.

In spite of the apparent large number of treatments for hot flashes, all the current therapies suffer from poor efficacy, are associated with unacceptable side effects or are contraindicated for certain patient populations. For example, HRT is not recommended for women with a history of breast cancer, uterine cancer, ovarian cancer, or venous thromboembolism. Recent data also suggests HRT may not be suitable for women with coronary artery disease. Non-hormonal treatments generally are not fully efficacious (e.g. clonidine) and/or cause adverse effects (e.g., venlafaxine, gabapentin).

Many publications have appeared within the last ten years disclosing selective estrogen receptor modulators (SERMs), e.g., U.S. Pat. Nos. 5,484,795, 5,484,798, 5,510,358, 5,998,401 and WO 96/09040. Many of these SERMs, generally speaking, have been found to have a beneficial estrogen agonist activity in the bone and cardiovascular systems with a concomitant beneficial estrogen antagonist activity in the breast. A small, particularly useful subset of such compounds has also been found to have an estrogen antagonist effect or to have a non-estrogenic effect in the uterus. However, the actual use of a SERM in the treatment of vasomotor symptoms has also been hampered by problems with efficacy, e.g., during Phase III clinical studies of raloxifene for the treatment/prevention of post-menopausal osteoporosis, raloxifene was associated with a slight increased incidence of hot flash compared to placebo and tamoxifen is known to induce hot flashes in more than 50% of patients (Arch. Intern. Med. 1991, 151, 1842).

There, therefore, remains an unmet medical need for vasomotor symptom therapies that overcome the liabilities of current treatments. In particular, there is a need for a medication that possesses the positive attributes of previously disclosed SERMs such as raloxifene (i.e., positive effects on bone, uterus, breast and cardiovascular system) but also alleviates vasomotor symptoms.

SUMMARY OF INVENTION

The present invention relates to a compound of formula I:

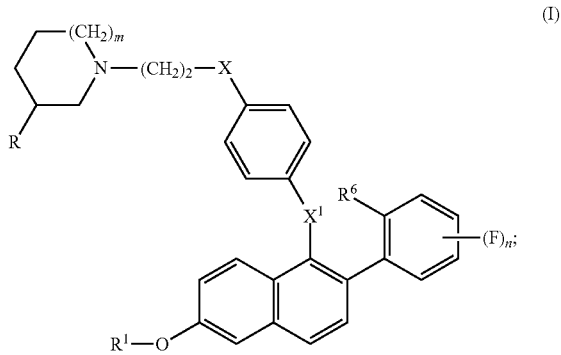

wherein:
m is 0, 1 or 2;
n is 1, 2, 3 or 4;
R is H or methyl provided that if m is 1 or 2, then R must be H and that if m is 0, then R must be methyl;
$R^1$ is H, $SO_2(n-C_4-C_6$ alkyl) or $COR^2$;
X is O or $NR^3$;
$X^1$ is O, $CH_2$ or C=O;

$R^6$ is H or F or $R^6$ combines with $X^1$ to form a moiety of the formula:

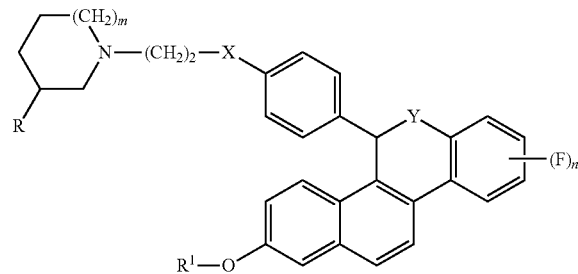

wherein Y is O, S, SO or $NR^4$;

$R^2$ is $C_1$-$C_6$ alkyl; $C_1$-$C_6$ alkoxy; $NR^5R^{5a}$; phenoxy; or phenyl optionally substituted with halo;

$R^3$ and $R^4$ are independently H or $C_1$-$C_6$ alkyl; and $R^5$ and $R^{5a}$ are independently H, $C_1$-$C_6$ alkyl or phenyl; or a pharmaceutical acid addition salt thereof.

The present invention also relates to a pharmaceutical composition that comprises a compound of formula I, or a pharmaceutical acid addition salt thereof, and a pharmaceutical carrier. In another embodiment, the pharmaceutical composition of the present invention may be adapted for use in treating one or more vasomotor symptoms.

The present invention also relates to methods for treating one or more vasomotor symptoms employing a compound of formula I, or a pharmaceutical acid addition salt thereof.

In addition, the present invention relates to a compound of formula I, or a pharmaceutical acid addition salt thereof, for use in treating one or more vasomotor symptoms. The present invention is further related to the use of a compound of formula I, or a pharmaceutical acid addition salt thereof, for the manufacture of a medicament for treating one or more vasomotor symptoms.

The present invention also relates to a compound of formula II:

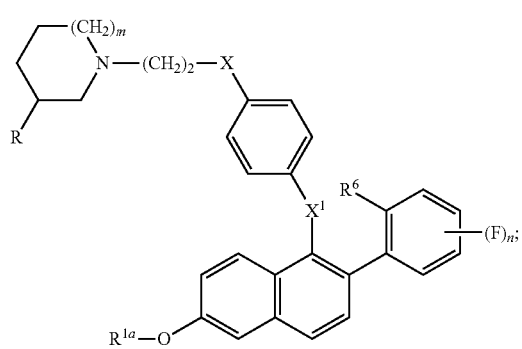

or an acid addition salt thereof; wherein m, n, R, and $X^1$ areas defined above for a formula I compound and:

$R^{1a}$ is H, $SO_2CH_3$, $SO_2$(n-$C_4$-$C_6$ alkyl), $COR^2$, $C_1$-$C_6$ alkyl or benzyl;

$R^6$ is H or F or $R^6$ combines with $X^1$ to form a moiety of the formula.

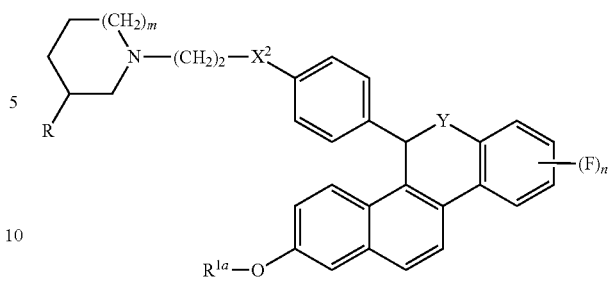

wherein Y is as defined above for a formula I compound;

$X^2$ is O or $NR^7$; and $R^7$ is H, $C_1$-$C_6$ alkyl or $CO_2$($C_1$-$C_6$ alkyl); provided that if $R^{1a}$ is H, $SO_2$(n-$C_4$-$C_6$ alkyl) or $COR^2$, then $X^2$ is $NR^7$ and $R^7$ is $CO_2$($C_1$-$C_6$ alkyl); useful as an intermediate to a compound of formula I.

The present invention also relates to a compound of formula III:

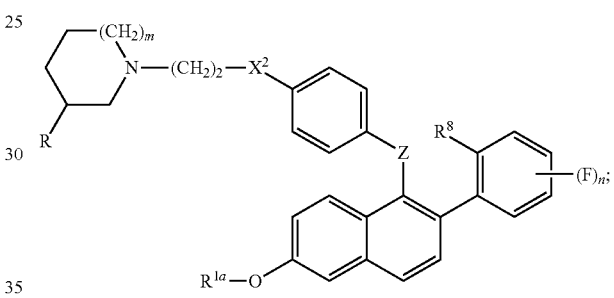

or an acid addition salt thereof, wherein m, n, R and $R^{1a}$ are as defined above for a formula II compound and wherein:

$X^2$ is O or $NR^7$;

$R^8$ is OH, O($C_1$-$C_6$ alkyl), S($C_1$-$C_6$ alkyl) or $NR^4$($CO_2$($C_1$-$C_6$ alkyl))

Z is C=O or CHOH; and $R^7$ is H, $C_1$-$C_6$ alkyl or $CO_2$($C_1$-$C_6$ alkyl); useful as an intermediate to a compound of formula I where $R^6$ combines with $X^1$.

DETAILED DESCRIPTION

Unless specified otherwise, reference hereafter to "a compound of formula I" includes the pharmaceutical acid addition salts thereof.

The compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

For the purposes of the present invention, as disclosed and claimed herein, the following terms are defined below.

The term "halo" refers to fluoro, chloro, bromo and iodo. The term "$C_1$-$C_6$ alkyl" represents a straight, branched or cyclic hydrocarbon moiety having from one to six carbon atoms, e.g., methyl, ethyl, n-propyl, isopropyl, cyclopropyl, n-butyl, isobutyl, sec-butyl, t-butyl, cyclobutyl, pentyl, cyclopentyl, hexyl, cyclohexyl and the like. Moieties such as a cyclobutylmethylenyl and cyclopropylmethyleneyl are also included within the scope of a $C_1$-$C_6$ alkyl group. The term "$C_1$-$C_4$ alkyl" refers specifically to methyl, ethyl, n-propyl, isopropyl, cyclopropyl, n-butyl, isobutyl, sec-butyl, t-butyl, cyclopropylmethyl and cyclobutyl. The term "n-$C_4$-$C_6$ alkyl" refers specifically to n-butyl, n-pentyl and n-hexyl. A "$C_1$-$C_6$ alkoxy" group is a $C_1$-$C_6$ alkyl moiety connected through an oxy linkage.

The term "pharmaceutical" when used herein as an adjective means substantially non-deleterious.

A pharmaceutical "acid addition salt" is a salt formed by reaction of the free base form of a compound of formula I with a pharmaceutical acid, such as described in the Encyclopedia of Pharmaceutical Technology, editors James Swarbrick and James C. Boylan, Vol 13, 1996 "Preservation of Pharmaceutical Products to Salt Forms of Drugs and Absorption". Specific salt forms include, but are not limited to the: acetate, benzoate, benzenesulfonate, 4-chlorobenzenesulfonate; citrate; ethanesulfonate; fumarate; d-gluconate; d-glucuronate; glutarate; glycolate; hippurate; hydrochloride; 2-hydroxyethanesulfonate; dl-lactate; maleate; d-malate; 1-malate; malonate; d-mandelate; 1-mandelate; methanesulfonate; 1,5 napthalenedisulfonate; 2-naphthalenesulfonate; phosphate; salicylate; succinate; sulfate; d-tartrate; 1-tartrate; and p-toluenesulfonate.

The terms "treating" and "treat" as used herein, means alleviating, ameliorating, preventing, prohibiting, restraining, slowing, stopping, or reversing the progression or severity of a pathological condition, or sequela thereof, described herein. The term "preventing" means reducing the likelihood that the recipient of a compound of formula I will incur, further incur or develop any of the pathological conditions, or sequela thereof, described herein.

A "vasomotor symptom" is a condition selected from the list of: hot flash, night sweats, vaginal dryness, sleep disturbances, nausea and mood swings; wherein said condition results from a decrease of circulating endogenous estrogen that occurs in a woman following cessation or reduction of menstruation due to natural, surgical, or other processes.

The term "woman in need thereof" is a woman either suffering from the claimed pathological condition, or is a woman at a recognized risk thereof, as determined by medical diagnosis, i.e., as determined by the attending physician.

As used herein, the term "effective amount" means an amount of a compound of formula I that is capable of treating the conditions described herein.

PREFERRED COMPOUNDS AND EMBODIMENTS OF THE INVENTION

Certain compounds of the invention are particularly interesting and are preferred. The following listing sets out several groups of preferred compounds. It will be understood that each of the listings may be combined with other listings to create additional groups of preferred compounds. The following numbering system will be used to describe the preferred positions of the fluoro moieties:

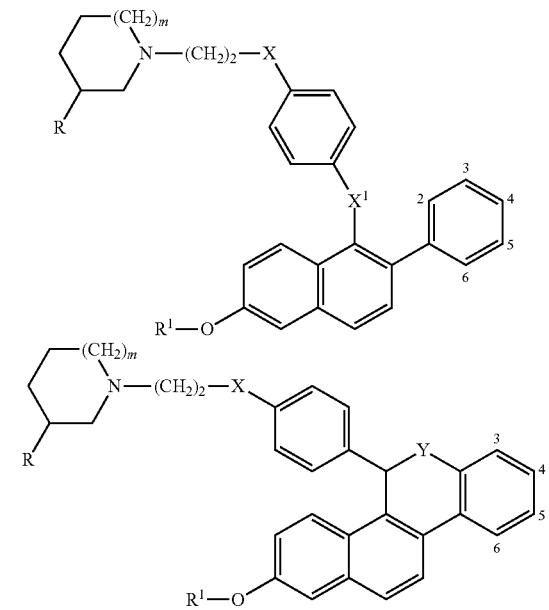

a) m is 1;
b) $R^6$ is H or F and n is 1, 2 or 3;
c) n is 1, 2 or 3;
d) n is 1 or 2;
e) n is 1;
f) n is 2;
g) $R^6$ is H or combines with $X^1$, n is 1 and the corresponding fluoro moiety is in the 4-position;
h) $R^6$ is H or combines with $X^1$, n is 2 and the corresponding fluoro moieties are in the 3,5-positions;
i) $R^1$ is H;
j) $R^1$ is H or $COR^2$ and $R^2$ is $C_1$-$C_6$ alkyl or phenyl;
k) $R^1$ is H or $COR^2$ and $R^2$ is $C_1$-$C_4$ alkyl, $NHCH_3$ or phenyl;
l) $R^3$ is H, methyl or ethyl;
m) $R^3$ is H;
n) X is O;
o) X is $NR^3$ and $R^3$ is H or methyl;
p) $X^1$ is O;
q) $R^6$ is H or F;
r) $R^6$ combines with $X^1$;
s) the hydrochloride salt form.
With respect to the chiral center designated below:

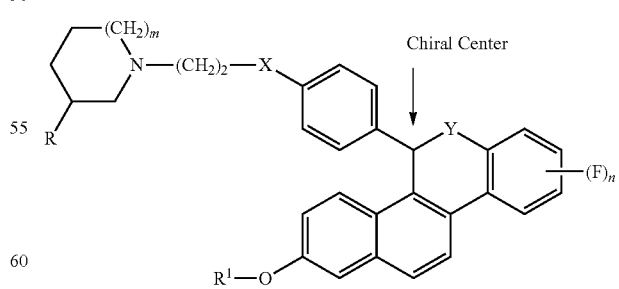

an enantiomeric excess (ee) of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column (see, e.g., J. Jacques, et al., "*Enantiomers, Racemates, and Resolutions*", John Wiley and Sons, Inc., 1981; E. L. Eliel and S. H. Wilen, "*Stereochemistry of Organic Compounds*", (Wiley-Interscience 1994), and European Patent Application No. EP-A-838448, published Apr. 29, 1998). Of course, the preferred enantiomer is that which possesses favorable activity in the biological assays disclosed herein. Employing the chiral chromatography techniques disclosed herein, the preferred enantiomer (the enantiomer with favorable activity) typically possesses the slower retention time, i.e., elutes second. In order to verify the identify of the preferred enantiomer in any given racemic mixture, the activity of the individual isomers should be verified in the biological assays described herein.

The compound of formula I is preferably employed in the treatment of hot flashes.

The compound of formula I is preferably formulated in a dosage unit form, i.e., in an individual delivery vehicle, for example, a tablet or capsule, prior to administration to the recipient woman.

The compound of formula I is preferably administered orally.

Synthesis

The compound of formula I may be prepared as described in the following Scheme (where $R^{8a}$ is $R^8$, H, or F), Preparations and Examples.

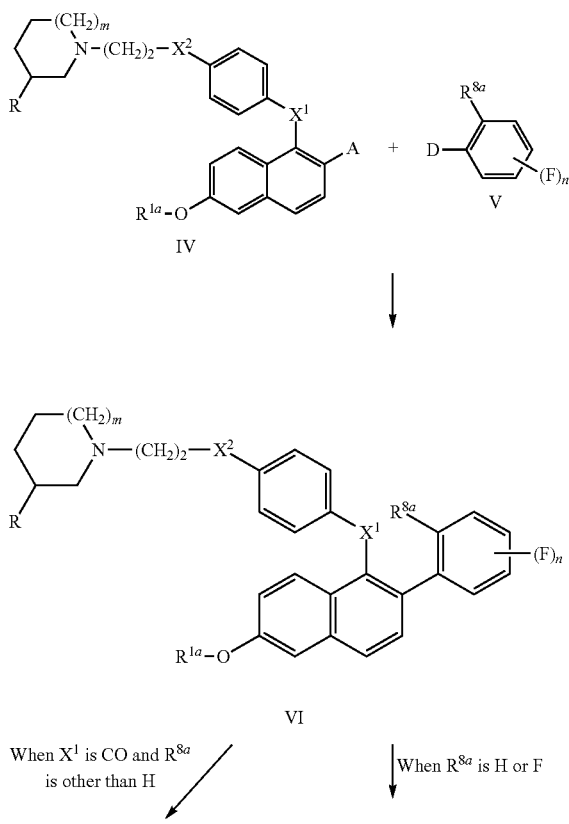

In Scheme 1, a compound of formula V is reacted with a compound of formula IV under usual "Suzuki" or "Stille" reaction conditions, i.e., wherein one of substituent "A" or "D" is a boronic acid/ester or alkyl stannane moiety and the other is a leaving group, e.g., chloro, bromo or iodo or a sulfonate group such as trifluoromethyl sulfonate, to provide a compound of formula VI (when $R^{8a}$ is $R^8$ then of formula III). When $X^1$ is CO in the formula VI compound, the keto group may be reduced under standard conditions, e.g., employing borane to provide the corresponding benzyl alcohol. This reduced product may be cyclized under standard conditions, e.g., when $R^{8a}$ is F, base catalyzation with potassium t-butoxide or when $R^{8a}$ is other than F, acid catalyzation with HCl, to provide the corresponding compound of formula I or II. Alternatively, the keto group may be reduced under conditions that promote the cyclization reaction thus performing both steps in "one-pot" (see, e.g., Examples 96 and 108 below).

When $R^{1a}$ is $SO_2CH_3$, $C_1$-$C_6$ alkyl or benzyl (preferably methyl, benzyl or $SO_2CH_3$) said hydroxy protecting groups may be removed under standard conditions (see, e.g., the procedures that follow or the latest edition of Greene, Protective Groups in Organic Synthesis, John Wiley & Sons, New York, N.Y.) to provide the compound of formula I where $R^1$ is H. Similarly, when $X^2$ is $NR^7$ and $R^7$ is $CO_2(C_1$-$C_6$ alkyl), said amino protecting group may also be removed as taught in the Greene. A formula I compound where $R^1$ is H may be further derivatized employing standard acylation or sulfonylation methodology to prepare a compound of formula I where $R^1$ is $COR^2$ or $SO_2(n$-$C_4$-$C_6$ alkyl).

Compounds of formula IV may be prepared as shown below or by procedures analogous to those found in the art. Compounds of formula V are, in general, commercially available or can be prepared by procedures readily available to the ordinarily skilled synthetic organic chemist or as shown below.

PREPARATIONS AND EXAMPLES

Chiral Separation Conditions:
All prep conditions use Chiralpak AD columns.
Conditions A: 3:2 heptane/IPA w/0.2% dimethylethylamine (DMEA), 8×30 cm 365 nm, 350 ml/min.
Conditions B: 3:2 heptane/IPA w/0.2% DMEA, 8×30 cm, 365 nm, 350 ml/min.
Conditions C: 80/10/10 heptane/3A/MeOH w/0.2% DMEA, 8×34 cm, 260 nm, 375 ml/min.
Conditions D: 75/15/10 heptane/IPA/MeOH w/0.2% DMEA, 8×34 cm, 260 nm, 375 ml/min.
Conditions E: 70/30 heptane/IPA w/0.2% DMEA, 8×34 cm, 260 nm, 375 ml/min.
Conditions F: 4:1 heptane/IPA w/0.2% DMEA, 8×30 cm, 350 nm, 350 ml/min.
Conditions G: 3:1 heptane/IPA w/0.2% DMEA, 8×33 cm, 340 nm, 375 ml/min.

Conditions H: 3:1 heptane/IPA w/0.2% DMEA, 8×33 cm, 340 nm, 375 ml/min.
Conditions I: 3:1 heptane/IPA w/0.2% DMEA, 8×33 cm, 360 nm, 375 ml/min.
Conditions J: 4:1 heptane/IPA w/0.2% DMEA, 8×30 cm, 260 nm, 350 ml/min.
Conditions K: 70/30 heptane/IPA w/0.2% DMEA, 8×34 cm, 320 nm, 350 ml/min.
Conditions L: 100% 3A w/0.2% DMEA, 8×30 cm, 260 nm, 300 ml/min.
Conditions M: 70/30 heptane/IPA w/0.2% DMEA, 8×30 cm, 260 nm, 350 ml/min.
Conditions N: 70/30 heptane/IPA w/0.2% DMEA, 8×30 cm, 260 nm, 350 ml/min.
Conditions O: 65/35 3A/heptane w/0.2% DMEA, 8×30 cm, 260 nm, 350 ml/min.
Conditions P: 100% 3A w/0.2% DMEA, 8×30 cm, 260 nm, 350 ml/min.
Conditions Q: 70/30 heptane/IPA w/0.2% DMEA, 8×30 cm, 260 nm, 350 ml/min.

Preparation 1

Trifluoromethanesulfonic acid 6-methoxy-1-[4-(2-piperidin-1-yl-ethoxy)-phenoxy]-naphthalen-2-yl ester

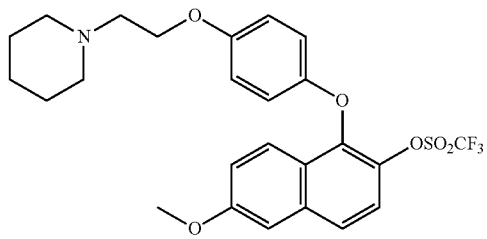

Add 6-methoxynaphthalene-2-ol (20 g, 114.8 mmol) to dimethylformamide (DMF, 250 mL) at ambient temperature followed by N-bromosuccinimide (NBS, 21.5 g, 120 mmol) over a 30 minute period. After 45 minutes, dilute with water (800 mL), collect and dry the precipitate to provide 25.5 g (87%) of 1-bromo-6-methoxy-naphthalen-2-ol.

Add 1-bromo-6-methoxy-naphthalen-2-ol (66.7 g, 264 mmol), potassium carbonate ($K_2CO_3$, 40.0 g, 290 mmol) and benzyl bromide (49.6 g, 290 mmol) to DMF (800 mL). Stir the mixture at ambient temperature for 1 hour. Add water (400 mL) to precipitate the product. Collect the precipitate and wash the filter cake with heptane (3×125 mL) then dry to provide 83.7 g of 2-benzyloxy-1-bromo-6-methoxy-naphthalene (86.2%).

Combine toluene (200 mL), 2-benzyloxy-1-bromo-6-methoxy-naphthalene (30 g, 87.4 mmol), 4-(2-piperidin-1-yl-ethoxy)phenol (23.2 g, 105 mmol) and cesium carbonate (34.4 g, 105 mmol), and heat the mixture to reflux. Remove a portion of the toluene (100 mL). Add ethyl acetate (390 mg, 437 mmol) and copper triflate benzene complex (2.20 g, 4.37 mmol) to the reaction mixture and stir for 5 minutes. Remove the solvent by distillation and heat the resulting residue to 174° C. for 1.5 hours. Dissolve the residue in a mixture of ethyl acetate (200 mL) and aqueous HO (1 N, 90 mL). Separate and concentrate the organics to a residue. Column chromatograph the residue to give 12.4 g of 1-{2-[4-(2-benzyloxy-6-methoxy-naphthalen-1-yloxy)-phenoxy]-ethyl}-piperidine (30%).

Add 1-{2-[4-(2-benzyloxy-6-methoxy-naphthalen-1-yloxy)-phenoxy]-ethyl}-piperidine (12.4 g, 25.5 mmol) to a methanol/ethyl acetate mixture (1:1, 490 mL) and heat to form a solution. Remove the heat and add ammonium formate (4.83 g, 76.6 mmol) and Pd(OH)$_2$ on carbon (20% ww, 1.58 g, 1.12 mmol). Reflux for 50 minutes then filter the mixture. Concentrate the filtrate to provide 9.9 g of 6-methoxy-1-[4-(2-piperidin-1-yl-ethoxy)-phenoxy]-naphthalene-2-ol (98.5%).

Cool dichloromethane (290 mL), triethylamine (3.08 g, 30.4 mmol) and 6-methoxy-1-[4-(2-piperidin-1-yl-ethoxy)-phenoxy]-naphthalene-2-ol (9.2 g, 23.4 g) to −50° C. and add trifluoromethane sulfonic acid anhydride (7.26 g, 25.7 mmol). Stir the resulting mixture at −50° C. for 2 hours then allow the mixture to warm to ambient temperature before stirring for an additional hour. Add brine (150 mL) and separate the organics. Wash the organics with NaHCO$_3$ then dry before concentrating to a residue. Crystallize the residue with ethyl ether—hexanes to provide 11.2 g of the title compound (90.9%).

Example 1

1-(2-{4-[2-(2,6-Difluoro-phenyl)-6-methoxy-naphthalen-1-yloxy]-phenoxy}-ethyl)-piperidine

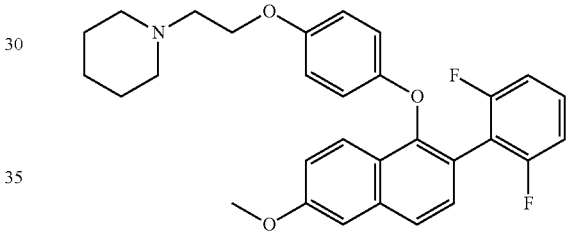

Dissolve trifluoromethanesulfonic acid 6-methoxy-1-[4-(2-piperidin-1-yl-ethoxy)-phenoxy]-naphthalen-2-yl ester (1.0 gm., 1.9 mmoles) in 20 ml DMF. To this solution add 2,6-difluorophenylboronic acid (0.6 gm., 3.8 mmoles), potassium phosphate (2.42 gm., 11.4 mmoles) and tetrakis(triphenylphosphine)palladium (0) (0.44 gm., 0.38 mmoles) and heat to 100° C. for 18 hours. Cool and filter the mixture and purify on an SCX column, eluting the impurities with methanol, then eluting the product with 2N ammonia/methanol. Purify further on a silica gel column eluting with a gradient of 50-100% methylene chloride/hexane containing 1% isopropyl amine to give 300 mg (32%) of the title compound.

Example 2

6-(2,6-Difluoro-phenyl)-5-[4-(2-piperidin-1-yl-ethoxy)-phenoxy]-naphthalen-2-ol hydrochloride Dissolve 1-(2-{4-[2-(2,6-difluoro-phenyl)-6-methoxy-naphthalen-1-yloxy]-phenoxy}-ethyl)-piperidine (300 mg., 0.61 mmoles) in 20 ml methylene chloride and chill in ice. To this add 2.0 ml of boron tribromide with swirling and allow to warm to room temperature. Pour this mixture into a two-phase mixture consisting of saturated sodium bicarbonate and a 3/1 mixture of chloroform/isopropanol. Wash the organic layer with brine and dry over 3A molecular sieves. Purify further using reverse phase chromatography to give 138 mg of the title compound (48%). Convert to hydrochloride salt and lyophilize. $^1$H-NMR (CDCl$_3$, 300 MHz) δ7.92 (d, J=9.0 Hz, 1H); 7.59 (d, J=8.4 Hz, 1H); 7.35 (d, J=8.4 Hz, 1H); 7.20-7.17 (m, 2H); 7.03 (dd, J=9.0, 2.1 Hz, 1H); 6.85-6.80 (m, 2H); 6.52 (s, 4H); 3.95 (t, J=5.7 Hz, 2H); 2.73 (t, J=6.0 Hz, 2H); 2.52-2.52 (m, 4H); 1.64-1.59 (m, 4H); 1.46-1.44 (m, 2H).

Example 3

1-(2-{4-[2-(2-Fluoro-phenyl)-6-methoxy-naphthalen-1-yloxy]-phenoxy}-ethyl)-piperidine hydrochloride

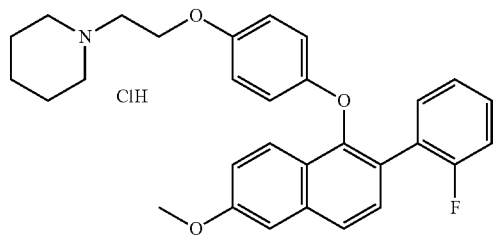

Charge an oven-dried 100 mL round-bottom flask with trifluoromethanesulfonic acid 6-methoxy-1-[4-(2-piperidin-1-yl-ethoxy)-phenoxy]-naphthalen-2-yl ester (300 mg, 0.57 mmol.) and place under nitrogen. Dissolve the solid in acetonitrile (10 ml) and add 2-fluorophenylboronic acid (240 mg, 1.71 mmol), tricyclohexylphosphine (48 mg, 0.17 mmol), palladium acetate (38 mg, 0.17 mmol), and cesium fluoride (780 mg, 5.14 mmol). Bring the solution to 85° C. and stir for 1 hour. Filter the solution over a pad of celite, rinse with acetonitrile and concentrate in vacuo. Purify the crude product using radial chromatography to give 295 mg (110%) of the free base of the title compound. Dissolve the free base in 3 mL ether and add 0.8 ml of 1N HCl. Immediately dry to give 305 mg of the tithe compound: mass spectrum (ion spray) m/z=472 (M−Cl).

Example 4

6-(2-Fluoro-phenyl)-5-[4-(2-piperidin-1-yl-ethoxy)-phenoxy]-naphthalen-2-ol hydrochloride Charge a 100 mL round-bottom flask with 1-(2-{4-[2-(2-fluoro-phenyl)-6-methoxy-naphthalen-1-yloxy]-phenoxy}-ethyl)-piperidine hydrochloride (290 mg, 0.57 mmol) in 5 mL anhydrous CH$_2$Cl$_2$ and cool to 0° C. under nitrogen. Add 2.90 mL (2.90 mmol) of a 1M CH$_2$Cl$_2$ solution of BBr$_3$ and monitor the reaction by ES-MS. After stifling for 1 hour, pour the reaction into a cold saturated solution of aqueous sodium bicarbonate and methylene chloride (150 mL). Dry the organic layer over sodium sulfate and concentrate in vacuo. Purify the crude product using radial chromatography eluting with 8% MeOH/CH$_2$Cl$_2$ to give 137 mg (52%) of the free base of the title compound. Prepare the hydrochloride salt by adding 0.8 mL of a 1N HCl in Et$_2$O solution: mass spectrum (ion spray) m/z=458 (M−Cl).

Example 5

1-(2-{4-[2-(2,4-Difluoro-phenyl)-6-methoxy-naphthalen-1-yloxy]-phenoxy}-ethyl)-piperidine hydrochloride

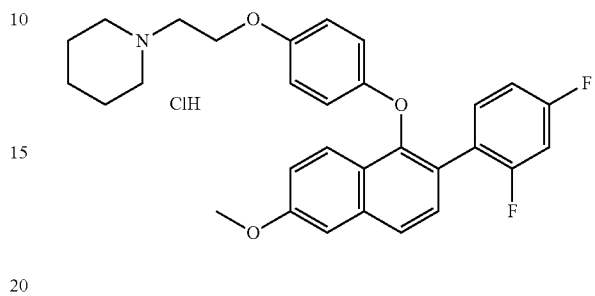

Combine trifluoromethanesulfonic acid 6-methoxy-1-[4-(2-piperidin-1-yl-ethoxy)-phenoxy]-naphthalen-2-yl ester (2.99 g, 5.70 mmol), 2,4-difluoro-benzeneboronic acid (2.70 g, 17.09 mmol), palladium(II)acetate (0.13 g, 0.57 mmol), tricyclohexylphosphine (240 mg, 0.85 mmol), cesium fluoride (7.79 g, 51.25 mmol) and acetonitrile (70 mL) and heat at 90° C. After 10 minutes, cool to ambient temperature, filter and remove solvent under vacuum. Dissolve in dichloromethane and wash with 1N aqueous hydrochloric acid, saturated aqueous sodium bicarbonate, saturated aqueous sodium chloride, dry with magnesium sulfate, filter and remove solvent under vacuum. Chromatograph on silica gel with dichloromethane/methanol mixtures and add 1M hydrogen chloride in ether (10 mL) to give 3.0 g (100%) of the title compound: mass spectrum (ion spray) m/z=488 (M−Cl).

Example 6

6-(2,4-Difluoro-phenyl)-5-[4-(2-piperidin-1-yl-ethoxy)-phenoxy]-naphthalen-2-ol hydrochloride Dissolve 1-(2-{4-[2-(3,4-difluoro-phenyl)-6-methoxy-naphthalene-1-yloxy]-phenoxy}-ethyl)-piperidine hydrochloride (3.00 g, 5.70 mmol) in dichloromethane (90 mL) and cool in an ice bath. Add boron tribromide (1M in dichloromethane, 18.0 mL, 18.0 mmol) and stir for 2.5 hours. Add methanol (20 mL), warm to ambient temperature and remove solvent under vacuum. Dissolve in dichloromethane with a minimum of methanol and wash with saturated aqueous sodium bicarbonate and remove solvent under vacuum. Crystallize with ethyl acetate/dichloromethane, filter solid to give the free base of the title compound. Dissolve the free base in dichloromethane/methanol, add 1M hydrogen chloride in ether (10 mL) and remove solvent under vacuum to give 2.68 g (92%) of the title compound: mass spectrum (ion spray) m/z=476 (M−Cl).

Example 7

1-(2-{4-[2-(2,5-Difluoro-phenyl)-6-methoxy-naphthalen-1-yloxy]-phenoxy}-ethyl)-piperidine hydrochloride

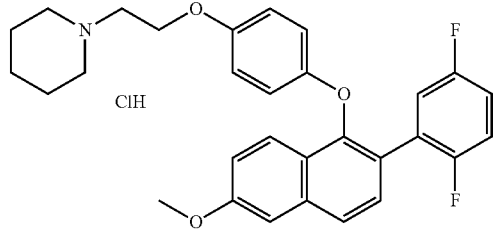

Combine trifluoromethanesulfonic acid 6-methoxy-1-[4-(2-piperidin-1-yl-ethoxy)-phenoxy]-naphthalen-2-yl ester (154 mg, 0.29 mmol), 2,5-difluorophenyl boronic acid (139 mg, 0.88 mmol), [1,1'-bis(diphenylphosphino)-ferrocene]dichloropalladium (II), complex with dichloromethane (1:1) (239 mg, 0.29 mmol), cesium fluoride (400 mg, 2.63 mmol) and acetonitrile (6 mL), stir and heat at 90° C. After 4 hours, cool to ambient temperature and remove solvent under vacuum. Suspend and sonicate the residue in ethyl ether, filter and remove the solvent under vacuum. Chromatograph the crude mixture on silica gel with dichloromethane/methanol mixtures, combine fractions containing product, add 1M hydrogen chloride in ether (1 mL) and remove solvent under vacuum to give 140 mg of the title compound: mass spectrum (ion spray) m/z=490 (M−Cl).

Example 8

6-(2,5-Difluoro-phenyl)-5-[4-(2-piperidin-1-yl-ethoxy)-phenoxy]-naphthalen-2-ol hydrochloride Dissolve 1-(2-{4-[2-(2,5-difluoro-phenyl)-6-methoxy-naphthalen-1-yloxy]-phenoxy}-ethyl)-piperidine hydrochloride (133 mg, 0.25 mmol) in dichloromethane (5 ml), cool in an ice bath and add boron tribromide (1M in dichloromethane, 0.76 mL, 0.76 mmol). Let slowly warm to ambient temperature over 18 hours, quench with saturated aqueous solution of sodium bicarbonate, dry organic layer with magnesium sulfate, filter and chromatograph on silica gel with dichloromethane/methanol mixtures. Combine fractions containing product, add 1M hydrogen chloride in ether (1 mL) and remove solvent under vacuum to give 108 mg (83%) of the title compound: mass spectrum (ion spray) m/z=476 (M−Cl).

Example 9

1-(2-{4-[6-Methoxy-2-(3,4,5-trifluoro-phenyl)-naphthalen-1-yloxy]-phenoxy}-ethyl)-piperidine

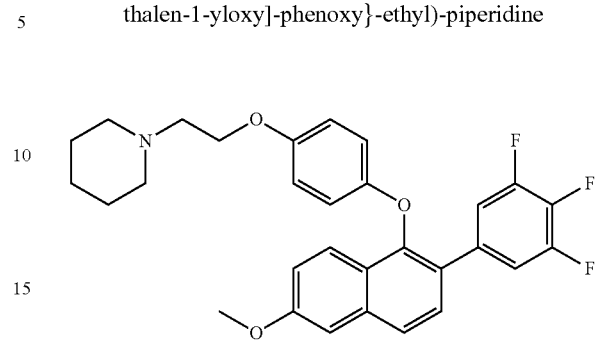

Charge a flask with trifluoromethanesulfonic acid 6-methoxy-1-[4-(2-piperidin-1-yl-ethoxy)-phenoxy]-naphthalen-2-yl ester (800 mg, 1.52 mmol), 3,4,5-trifluorobenzene boronic acid (804 mg, 4.57 mmol) and cesium fluoride (1.1 g, 7.6 mmol) and purge with nitrogen. In a separate flask, charge palladium(II)acetate (34 mg, 0.15 mmol) and tricyclohexylphosphine (64 mg, 0.23 mmol) and purge with nitrogen. Add degassed acetonitrile and sonicate under nitrogen for 10 minutes. Add the catalyst solution to the solids and plunge into an 80° C. oil bath for 10 minutes. Cool to room temperature and filter through celite. Concentrate and redissolve in methylene chloride. Wash with saturated aqueous sodium bicarbonate, separate, dry, filter and concentrate. Purify the residue over silica gel, eluting with 0 to 5% methanol in methylene chloride, to yield 720 mg (93%) of the title compound: mass spectrum (ion spray) 508.3 (M+H).

Example 10

6-(3,4,5-Trifluoro-phenyl)-5-[4-(2-piperidin-1-yl-ethoxy)-phenoxy]-naphthalen-2-ol hydrochloride Dissolve 1-(2-{4-[6-methoxy-2-(3,4,5-trifluoro-phenyl)-naphthalen-1-yloxy]-phenoxy}-ethyl)-piperidine (720 mg, 1.4 mmol) in methylene chloride (15 mL). Add 2M HCl in ether (1.4 mL, 2.8 mmol) and concentrate in vacuo. Dissolve the residue in methylene chloride (15 mL) and add boron tribromide (0.53 mL, 5.6 mmol) dropwise at 0° C. under nitrogen. Pour into cold saturated aqueous sodium bicarbonate after 45 minutes and extract with methylene chloride. Concentrate the organic layer and purify the residue over silica gel, eluting with 0 to 12% methanol in methylene chloride, to yield 554 mg (80%) of the free base of the title compound. Dissolve the free base (554 mg, 1.1 mmol) in ethyl acetate (6 mL) and ether (12 mL). Add 2M HCl in ether (1.1 mL, 2.2 mmol) and collect the precipitate. Dry in a vacuum oven at 50° C. overnight to yield 467 mg (79%) of the title compound: mass spectrum (ion spray) m/z=494.3 (M−Cl).

Example 11

1-(2-{4-[2-(2,3-Difluoro-phenyl)-6-methoxy-naphthalen-1-yloxy]-phenoxy}-ethyl)-piperidine

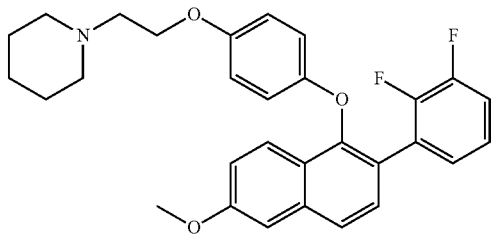

Using the procedure demonstrated in Example 9, react trifluoromethanesulfonic acid 6-methoxy-1-[4-(2-piperidin-1-yl-ethoxy)-phenoxy]-naphthalen-2-yl ester (800 mg, 1.52 mmol), 2,3-difluorobenzene boronic acid (720 mg, 4.57 mmol), cesium fluoride (2.1 g, 13.7 mmol), palladium(II) acetate (34 mg, 0.15 mmol) and tricyclohexylphosphine (64 mg, 0.23 mmol) to obtain 622 mg (84%) of the title compound: mass spectrum (ion spray) 490.4 (M+H).

Example 12

6-(2,3-Difluoro-phenyl)-5-[4-(2-piperidin-1-yl-ethoxy)-phenoxy]-naphthalen-2-ol hydrochloride Using the procedure demonstrated in Example 10, react 1-(2-{4-[2-(2,3-difluoro-phenyl)-6-methoxy-naphthalen-1-yloxy]-phenoxy}-ethyl)-piperidine (622 mg, 1.27 mmol), 2M HCl in ether (1.3 mL, 2.6 mmol) and boron tribromide (0.60 mL, 6.4 mmol) to give 309 mg (48%) of the title compound: mass spectrum (ion spray) 476.4 (M−Cl).

Example 13

1-(2-{4-[2-(3,5-Difluoro-phenyl)-6-methoxy-naphthalen-1-yloxy]-phenoxy}-ethyl)-piperidine

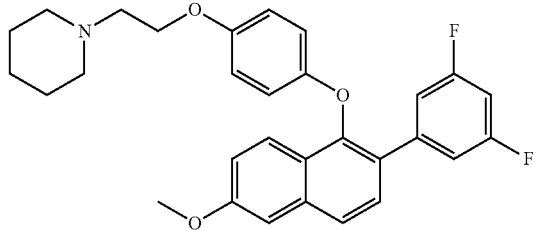

Using the procedure demonstrated in Example 9, react trifluoromethanesulfonic acid 6-methoxy-1-[4-(2-piperidin-1-yl-ethoxy)-phenoxy]-naphthalen-2-yl ester (3.5 g, 6.67 mmol), 3,5-difluorobenzene boronic acid (3.1 g, 19.6 mmol), cesium fluoride (9.2 g, 60.4 mmol), palladium(II)acetate (145 mg, 0.64 mmol) and tricyclohexylphosphine (290 mg, 1.03 mmol) to obtain 3.3 g (100%) of the title compound: mass spectrum (ion spray) 490.3 (M+H).

Example 14

6-(3,5-Difluoro-phenyl)-5-(4-(2-piperidin-1-yl-ethoxy)-phenoxy)-naphthalen-2-ol hydrochloride Using the same procedure as for 6-(3,4,5-trifluoro-phenyl)-5-[4-(2-piperidin-1-yl-ethoxy)-phenoxy]-naphthalen-2-ol hydrochloride salt; react 142-{4-[2-(3,5-difluoro-phenyl)-6-methoxy-naphthalen-1-yloxy]-phenoxy}-ethyl)-piperidine (3.8 g, 7.9 mmol), 2M HCl in ether (7.9 mL, 15.8 mmol) and boron tribromide (3.7 mL, 39.2 mmol) to give 2.6 g (64%) of the title compound after silica gel chromatography: mass spectrum (ion spray) 476.3 (M−Cl).

Example 15

6-(3,4-Difluoro-phenyl)-5-[4-(2-piperidin-1-yl-ethoxy)-phenoxy]-naphthalen-2-ol hydrochloride

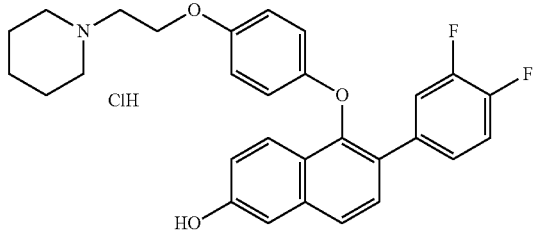

Prepare 6-(3,4-Difluoro-phenyl)-5-[4-(2-piperidin-1-yl-ethoxy)-phenoxy]-naphthalen-2-ol hydrochloride in a manner similar to Examples 7 and 8 to provide 1.79 g of the title compound: mass spectrum (ion spray): m/z=476 (M−Cl).

Preparation 2

4-[2-(3-Fluoro-phenyl)-6-methoxy-naphthalen-1-yloxy]-phenol

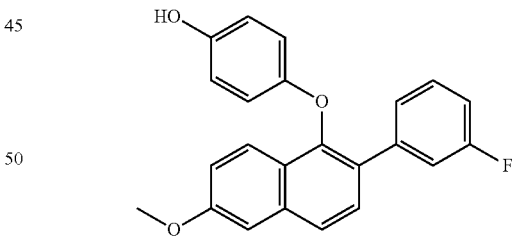

Charge an oven-dried 250 mL round-bottom flask with 6-methoxy-1-tetralone (3.0 g, 17.0 mmol.) and place under nitrogen. Dissolve the solid in toluene (30 mL) and add 1-bromo-3-fluorobenzene (4.7 mL, 42.6 mmol), sodium t-butoxide (6.5 g, 68.1 mmol), palladium acetate (76 mg, 0.34 mmol), and racemic BINAP (212 mg, 0.34 mmol). Heat the solution to 115° C. and stir for 18 hours. Dilute the solution with cold 5N HCl (50 mL) and ethyl acetate (200 mL). Separate the organic layer and dry over sodium sulfate, filter over a pad of celite and concentrate in vacuo. Purify the crude product using radial chromatography to give 3.4 g (74%) of the title compound. This material is used without further purification: mass spectrum (ion spray) m/z=267 (M−H).

Dissolve 2-(3-fluoro-phenyl)-6-methoxy-naphthalen-1-ol (3.36 g, 12.5 mmol) in N-methyl-2-pyrrolidinone (NMP) (10 mL) and add sodium hydride (500 mg, 60% oil dispersion, 12.5 mmol) at room temperature. After stirring for 1 hour this solution is added to a solution of 4-fluorobenzaldehyde (2.4 mL, 22.5 mmol) in NMP (10 mL) that has been heated to 185° C. Continue stirring for 2.5 hours. Cool the reaction to room temperature and add pH 7 buffer (50 mL) and extract with ethyl acetate (2×100 mL). Wash the organic extracts with water and filter through a plug of silica gel. Purify the crude product using radial chromatography giving 2.50 g (54%) of the title compound and use without further purification: mass spectrum (ion spray) m/z=371 (M−H).

Charge a 100 mL round-bottom flask with 4-[2-(3-fluoro-phenyl)-6-methoxy-naphthalen-1-yloxy]-benzaldehyde (2.5 g, 6.71 mmol) and ethyl acetate (5 mL). At room temperature add 2 mL of 35% hydrogen peroxide. To this solution slowly add 2 mL of concentrated sulfuric acid. The mixture warms to approximately 40° C. and returns to room temperature where it is stirred for 2 hours. Dilute the reaction with water and ethyl acetate (100 mL) and dry the organic layer over sodium sulfate, filter and concentrate in vacuo. Purify the crude product using radial chromatography eluting with $CH_2Cl_2$ to yield 540 mg (22%) of the title compound: mass spectrum (ion spray) m/z=359 (M−H).

Example 16

1-(2-{4-[2-(3-Fluoro-phenyl)-6-methoxy-naphthalen-1-yloxy]-phenoxy}-ethyl)-piperidine hydrochloride

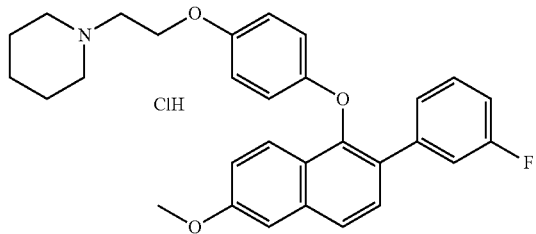

To 4-[2-(3-fluoro-phenyl)-6-methoxy-naphthalen-1-yloxy]-phenol (180 mg, 0.50 mmol) in 10 mL anhydrous DMF is added sodium hydride (60 mg, 60% oil dispersion, 1.50 mmol) and the solution stirred 30 minutes at room temperature. Add 142-chloroethyl)piperidine hydrochloride (138 mg, 0.75 mmol) and stir the reaction for 3 days. Dilute the reaction with methylene chloride, wash with saturated sodium bicarbonate (1×), brine (1×), extract the organics and dry over sodium sulfate. Purify the crude product using radial chromatography eluting with 4% MeOH/$CH_2Cl_2$ to yield 234 mg (99%) of the free base of the title compound. Form the hydrochloride by adding 0.8 mL of a 1N HCl in $Et_2O$ solution; mass spectrum (ion spray) m/z=472 (M−Cl).

Example 17

6-(3-Fluoro-phenyl)-5-[4-(2-piperidin-1-yl-ethoxy)-phenoxy]-naphthalen-2-ol hydrochloride Charge a 100 mL round-bottom flask with 1-(2-{4-[2-(3-fluoro-phenyl)-6-methoxy-naphthalen-1-yloxy]-phenoxy}-ethyl)-piperidine hydrochloride (245 mg, 0.48 mmol) and cooled to 0° C. under nitrogen. Add 1.45 mL of a 1M $CH_2Cl_2$ solution of $BBr_3$ and monitor the reaction by ES-MS. After stirring for 1 hour, pour the reaction into a cold saturated solution of aqueous sodium bicarbonate and methylene chloride (150 mL). Dry the organic layer over sodium sulfate and concentrate in vacuo. Purify the crude product using radial chromatography eluting with 4% MeOH/$CH_2$ to give 139 mg (63%) of the free base of the title compound. Form the hydrochloride salt by adding 0.8 mL of a 1N HCl in $Et_2O$ solution: mass spectrum (ion spray) m/z=458 (M−Cl).

Preparation 3

4-[6-Benzyloxy-2-(4-fluoro-phenyl)-naphthalen-1-yloxy]-phenol

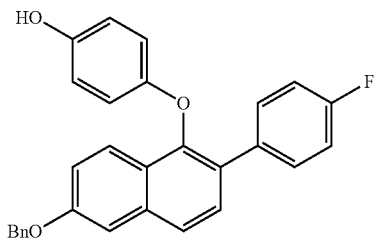

Add bromine (107 mL, 2.08 mol) into a solution of 6-benzyloxy-3,4-dihydro-2H-naphthalen-1-one (250 g, 0.99 mol) in chloroform (2 L) at 5° C. over 1.5 hours. Add sodium thiosulfate solution (250 mL) to quench the reaction at 0° C. Add ethyl acetate (1 L) and separate layers. Extract the aqueous layer with $CH_2Cl_2$ (500 mL) and combine the organic layers, wash with aqueous sodium bicarbonate solution and brine. Dry with sodium sulfate and concentrate in vacuo. Triturate the residue by adding 10% ethyl acetate in hexane (600 mL) to obtain a solid. Filter and dry the solid to get 405 g (100%) of 6-benzyloxy-2,2-dibromo-3,4-dihydro-2H-naphthalen-1-one.

Add 1M sodium methoxide (215 mL, 0.99 mol) into a solution of 6-benzyloxy-2,2-dibromo-3,4-dihydro-2H-naphthalen-1-one (205 g, 0.5 mol) in methanol (1.3 L). Heat the suspension to dissolution. Cool the reaction mixture to 0° C. and add 1N HCl (540 mL). Add $H_2O$ (3 L) and cool to 3° C. to obtain a solid. Filter and dry the solid to obtain 152 g (92%) of 6-benzyloxy-2-bromo-naphthalen-1-ol.

Add sodium hydride (24 g, 0.6 mmol) portionwise to a solution of 6-benzyloxy-2-bromo-naphthalen-1-ol (179 g, 0.54 mol) in THF (3.0 L) at 0° C. Add methanesulfonyl chloride (47 mL, 0.61 mol) over 45 minutes and stir the reaction for 1.5 hours at 10° C. Add sodium bicarbonate solution (500 mL) and water (500 ml). Separate the layers and extract the aqueous layer with ethyl acetate (500 mL×2). Combine the organic layers and wash with brine (200 mL). Dry with magnesium sulfate, filter and concentrate in vacuo. Triturate the residue by adding 20% ethyl acetate in hexane (1 L) to obtain a solid. Filter, wash the solid with toluene (200 mL×2) and dry the solid to get 176 g (80%) of methanesulfonic acid 6-benzyloxy-2-bromo-naphthalen-1-yl ester.

Combine methanesulfonic acid 6-benzyloxy-2-bromo-naphthalen-1-yl ester (10.0 g, 24.4 mmol), 4-fluorophenyl-boronic acid (10.2 g, 729 mmol), sodium carbonate (7.8 g, 73.6 mmol) and tetrakistriphenylphosphine palladium (2.8 g, 2.4 mmol) in a mixture of toluene (300 mL), ethanol (60 mL) and water (40 mL). Heat the mixture at 100° C. for 12 hours. Cool and filter the suspension through a pad of celite. Evaporate the solvent in vacuo. Wash the residue with sodium bicarbonate solution and brine. Dry with magnesium sulfate and concentrate in vacuo. Purify the residue over silica gel, eluting the material with a step gradient of methanol/dichloromethane (0 to 10%), to obtain 10.1 g (98%) of methanesulfonic acid 6-benzyloxy-2-(4-fluoro-phenyl)-naphthalen-1-yl ester.

Dissolve methanesulfonic acid 6-benzyloxy-2-(4-fluoro-phenyl)-naphthalen-1-yl ester (5.2 g, 12.3 mmol) in 5M sodium hydroxide (12 mL, 60 mmol), THF (86 mL) and MeOH (86 mL). Heat to 50° C. for 1 hour. Cool and add ethyl acetate (100 mL). Wash the organic layer with 1N HCl, saturated sodium bicarbonate solution and brine. Dry with magnesium sulfate and concentrate in vacuo to obtain 3.4 g (89%) of 6-benzyloxy-2-(4-fluoro-phenyl)-naphthalen-1-ol.

Add sodium hydride (400 mg, 10 mmol) into a solution of 6-benzyloxy-2-(4-fluoro-phenyl)-naphthalen-1-ol in NMP (40 mL). Add the above alkoxide suspension into a solution of 4-fluorobenzaldehyde (2 mL, 19 mmol) in NMP (30 mL) at 165° C. Heat at 165° C. for 1 hour. Cool and add buffer solution (pH=7, 10 mL). Add diethyl ether (1 L). Separate the layers and wash the aqueous layer with diethyl ether (2×200 mL). Combine the organic layers, dry with magnesium sulfate and concentrate in vacuo. Chromatograph the residue on a biotage column eluting the material with a step gradient of methanol/dichloromethane (0 to 10%) to obtain 2.9 g (70%) of 4-[6-benzyloxy-2-(4-fluoro-phenyl)-naphthalen-1-yloxy]-benzaldehyde.

Add 18M $H_2SO_4$ (1 mL, 16.8 mmol) dropwise into a solution of $H_2O_2$ (1 mL, 9.7 mmol) and 4-[6-benzyloxy-2-(4-fluoro-phenyl)-naphthalen-1-yloxy]-benzaldehyde at 0° C. and stir at room temperature for 12 hours. Add $H_2O$ (20 mL) and $CH_2Cl_2$ (100 mL). Separate layers and extract the aqueous layer with $CH_2Cl_2$ (2×50 mL). Combine the organic layers, dry with magnesium sulfate and concentrate in vacuo to obtain 1.88 g (73%) of the title compound: mass spectrum (ion spray) m/z=435.1 (M–H).

Example 18

1-(2-{4-[6-Benzyloxy-2-(4-fluoro-phenyl)-naphthalen-1-yloxy]-phenoxy}-ethyl)-piperidine

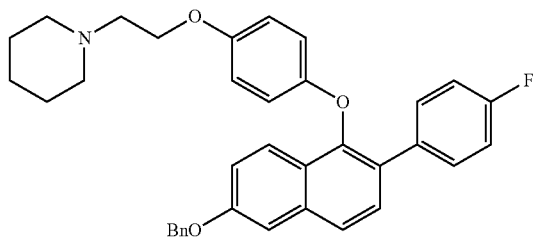

Dissolve 4-[6-benzyloxy-2-(4-fluoro-phenyl)-naphthalen-1-yloxy]-phenol (5.20 g, 11.91 mmol) in DMF (60 mL) under $N_2$ and add NaH (1.43 g, 35.74 mmol, 60% wt). Stir the solution for 0.5 hours at room temperature then add 1-(2-chloro-ethyl)-piperidine, HCl salt (3.29 g, 17.87 mmol). Continue to stir the solution for and then add water (300 mL). Extract the aqueous layer with $CH_2Cl_2$ (3×300 mL) and then combine the organic layers. Dry the organic layer with $Na_2SO_4$, then filter, concentrate and purify it by flash column chromatography (silica gel, 0-4% MeOH—$NH_4OH$ (10/1, v/v)/$CH_2Cl_2$) to give 6.5 g (99%) of the title compound: mass spectrum (ion spray) m/z=548.3 (M+H).

Example 19

6-(4-Fluoro-phenyl)-5-[4-(2-piperidin-1-yl-ethoxy)-phenoxy]-naphthalen-2-ol hydrochloride Dissolve 1-(2-{4-[6-benzyloxy-2-(4-fluoro-phenyl)-naphthalen-1-yloxy]-phenoxy}-ethyl)-piperidine (6.5 g, 11.87 mmol) in MeOH/THF (200 mL, v/v=1/1) under $N_2$. Add Pd/C (0.65 g, 10%) and exchange the $N_2$ for $H_2$ three times. Stir the reaction mixture for two hours then filter out the Pd/C. Remove the solvent and purify the residue by column chromatography (silica gel, 2-8% MeOH—$NH_4OH$ (10/1, v/v)/$CH_2Cl_2$) to give 2.93 g (54%) of the free base of the title compound. Dissolve the free base (2.93 g, 6.41 mmol) in $CH_2Cl_2$ (100 mL), and cool it to −78° C. Add HCl (10 mL, 2.0 M in $Et_2O$), and stir the solution for 10 minutes. Remove the solvent under reduced pressure and at 40° C., overnight, in vacuo to give 3.17 g (100%) of the title compound: mass spectrum (ion spray) m/z=458.2 (M–Cl).

Preparation 4

Trifluoromethanesulfonic acid 1-[4-(2-azepan-1-yl-ethoxy)-phenoxy]-6-methoxy-naphthalen-2-yl ester

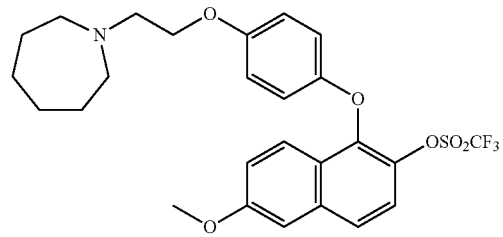

Add sodium hydride (18 g, 0.45 mol) into a solution of 4-benzyloxylphenol (41 g, 0.20 mol) and 2-(hexamethylene-imino)ethyl chloride hydrochloride (44 g, 0.22 mmol) in TIE (600 mL) and DMF (100 mL) at room temperature. Heat to 60° C. for 30 minutes. Pour the solution into ice and water. Dilute with ethyl acetate (500 mL) and separate layers. Dry the organic layer with magnesium sulfate, filter and concentrate under reduced pressure to give brown oil. Dissolve the oil in ethyl acetate (500 mL) and methanol (500 mL). Add ammonium formate (100 g, 1.59 mol) and palladium on carbon (10 g, 9.4 mmol). Heat the mixture to reflux for 30 minutes. Add ammonium formate (100 g, 1.59 mol) and palladium on carbon (10 g, 9.4 mmol). Heat the reaction mixture for 30 minutes. Filter the suspension through a pad of celite and elute with ethyl acetate (500 mL). Evaporate solvent under reduced pressure and add water (100 mL). Dilute the mixture with ethyl acetate (500 mL) and separate layers. Wash the organic layer with saturated sodium bicarbonate solution (2×200 mL), dry with magnesium sulfate, filter and evaporate solvent under reduced pressure to give 31 g (64%) of 4-(2-azepan-1-yl-ethoxy)-phenol.

Combine 2-benzyloxy-1-bromo-6-methoxy-naphthalene (31 g, 90 mmol), 4-(2-azepan-1-yl-ethoxy)-phenol (31 g, 132 mmol), copper bronze (12 g, 189 mmol), potassium carbonate (25 g, 181 mmol) and pyridine (400 ml). Heat the reaction mixture to reflux for 85 hours. Coot and filter the residue with celite and elute with methanol and methylene chloride (500 mL, V/V=1:5). Evaporate solvent under reduced pressure and chromatograph the residue on a silica gel column eluting the material with a step gradient of methanol/dichloromethane (0 to 10%) to get 19 g (43%) of 1-{2-[4-(2-benzyloxy-6-methoxy-naphthalen-1-yloxy)-phenoxy]ethyl}-azepane.

Dissolve 1-{2-[4-(2-benzyloxy-6-methoxy-naphthalen-1-yloxy)-phenoxy]-ethyl}-azepane (19 g, 38 mmol) in ethyl acetate (500 mL) and methanol (600 ml Heat the mixture to obtain a clear solution. Cool to room temperature. Add ammonium formate (30 g, 476 mmol) and palladium on carbon (2 g, 1.9 mmol). Heat to reflux for 30 minutes. Add ammonium formate (7 g, 111 mmol) and palladium on carbon (0.7 g, 0.7 mmol). Heat to reflux for 30 minutes. Filter the suspension through a pad of celite and elute with ethyl acetate (500 mL). Evaporate solvent under reduced pressure and add water (100 mL). Dilute the mixture with ethyl acetate (500 mL) and separate layers. Wash the organic layer with saturated sodium bicarbonate solution (2×200 mL), dry with magnesium sulfate, filter and evaporate solvent under reduced pressure to give 15.1 g (97%) of 1-[4-(2-azepan-1-yl-ethoxy)-phenoxy]-6-methoxy-naphthalen-2-ol.

Add trifluoromethanesulfonic anhydride (7 mL, 42 mmol) into a solution of 1-[4-(2-azepan-1-yl-ethoxy)-phenoxy]-6-methoxy-naphthalen-2-ol (15 g, 37 mmol), triethylamine (20 mL) and methylene chloride (500 mL) at −50° C. Warm the reaction mixture to room temperature and stir for 1 hour at that temperature. Cool the reaction mixture to −78° C. and add brine (20 ml). Warm the reaction to room temperature. Separate layer and wash the organic layer with saturated sodium bicarbonate solution (100 mL) and brine. Dry the organic layer with magnesium sulfate, filter and evaporate solvent under reduced pressure. Chromatograph the residue on a silica gel column eluting the material with a step gradient of methanol/dichloromethane (0 to 10%) to get 20 g (99%) of trifluoro-methanesulfonic acid 1-[4-(2-azepan-1-yl-ethoxy)-phenoxy]-6-methoxy-naphthalen-2-yl ester.

Example 20

1-(2-{4-[2-(3,5-Difluoro-phenyl)-6-methoxy-naphthalen-1-yloxy]-phenoxy}-ethyl)-azepane

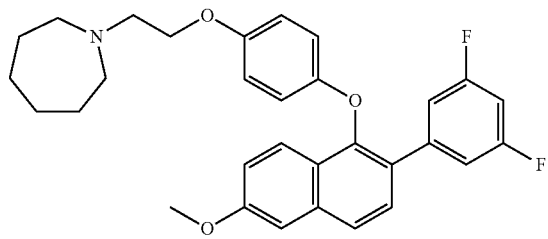

Dissolve trifluoromethanesulfonic acid 1-[4-(2-azepan-1-yl-ethoxy)-phenoxy]-6-methoxy-naphthalen-2-yl ester (435 mg, 0.80 mmol), cesium fluoride (864 mg, 5.7 mmol) and 1,3-difluoro-benzene boronic acid (383 mg, 2.4 mmol) in dry acetonitrile (5 mL) and stir for 10 minutes. In a separate flask suspend palladium acetate (18 mg, 0.08 mmol), and tricyclohexyl phosphine (33 mg, 0.12 mmol) in dry acetonitrile (15 mL) and sonicate under nitrogen for 10 minutes. Combine contents of both flasks and heat reaction at 60° C. for 15 minutes. Cool reaction and filter through celite and concentrate in vacuo. Purify crude product by silica gel chromatography using a 1-3% gradient of methanol in dichloromethane to yield 400 mg (98%) of the title compound: mass spectrum (ion spray) m/z=504.2 (M+H).

Example 21

5-[4-(2-Azepan-1-yl-ethoxy)-phenoxy]-6-(3,5-difluoro-phenyl)-naphthalen-2-ol hydrochloride Dissolve 1-(2-{4-[2-(3,5-difluoro-phenyl)-6-methoxy-naphthalen-1-yloxy]-phenoxy}-ethyl)-azepane (583 mg, 1.2 mmol) in dichloromethane (10 mL). Cool to 0° C., add 2M HCl (1.2 mL, 2.3 mmol) and stir at room temperature for 15 minutes. Concentrate in vacuo. Redissolve the salt in dichloromethane (10 mL) and cool to 0° C. Add boron tribromide (972 mg, 3.5 mmol) dropwise and bring to room temperature. Stir reaction for 1.5 hours and pour reaction mixture onto ice, saturated sodium bicarbonate (10 mL) and methanol (10 mL). Extract with dichloromethane, combine extracts and wash with water and saturated sodium bicarbonate. Dry with sodium sulfate, filter, and concentrate in vacuo. Purify by silica gel chromatography using a 1-4% gradient of methanol in dichloromethane to yield 366 mg (65%) of the free base of the title compound. Dissolve free-base in 10 mL dichloromethane and add 2M HCl (0.8 mL) stir for 10 minutes and concentrate in vacuo to yield 343 mg (88%) of title compound: mass spectrum (ion spray) m/z=490.3 (M–Cl).

Example 22

1-(2-{4-[2-(3,4-Difluoro-phenyl)-6-methoxy-naphthalen-1-yloxy]-phenoxy}-ethyl)-azepane

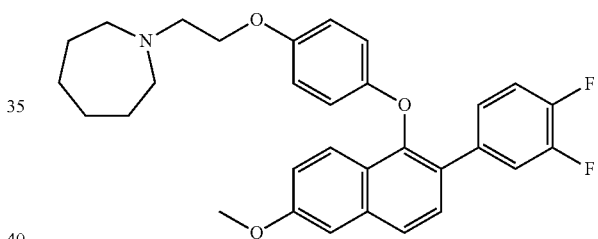

Combine palladium acetate (33 mg, 0.15 mmol), tricyclohexyl phosphine (61 mg, 0.22 mmol) and acetonitrile (6 mL). Sonicate the mixture for 5 minutes. Combine trifluoromethanesulfonic acid 1-[4-(2-azepan-1-yl-ethoxy)-phenoxy]-6-methoxy-naphthalen-2-yl ester (787 mg, 1.46 mmol), cesium fluoride (2.00 g, 13.2 mmol), 3,4-difluorophenylboronic acid (692 mg, 4.38 mmol) and acetonitrile (16 mL). Add the sonicated Pd/Pcy$_3$ suspension to reaction vessel and heat to 90° C. for 30 minutes. Cool to room temperature and filter through pad of Celite and evaporate the solvent. Dissolve residue in ethyl acetate (40 mL) and wash with saturated NaHCO$_3$ (10 mL). Separate the layers, wash the organic layer with brine (10 ml), dry with MgSO$_4$, filter, and concentrate in vacuo. Chromatograph the residue on a SiO$_2$ column eluting the material with methanol in dichloromethane (0 to 5%) to give 630 mg (86%) of the title compound: mass spectrum (ion spray) m/z=504.2 (M+H).

Example 23

5-[4-(2-Azepan-1-yl-ethoxy)-phenoxy]-6-(3,4-difluoro-phenyl)-naphthalen-2-ol hydrochloride Dissolve 1-(2-{4-[2-(3,4-difluoro-phenyl)-6-methoxy-naphthalen-1-yloxy]-phenoxy}-ethyl)-azepane (630 mg, 1.25 mmol) in dichloromethane (20 ml). Add 2M HCl in diethyl ether (1 mL, 2.0 mmol). Stir for 5 minutes. Concentrate the slurry and dry in vacuo. Dilute the residue in dichloromethane (20 ml) and blanket with nitrogen. Cool the solution to 0° C. with external ice bath. Add BBr$_3$ (0.4 mL, 4.3 mmol). Stir the reaction at room temperature for 30 minutes and add the reaction mixture in saturated aqueous NaHCO$_3$ (20 ml), ice (5 g) and methanol (5 mL). Dilute with dichloromethane (20 mL), separate the layers, wash the organic layer with brine (10 ml), dry with MgSO$_4$, filter, and concentrate in vacuo. Chromatograph the residue on a SiO$_2$ column eluting the material with a step gradient of methanol/dichloromethane (0 to 5%) to get the free base of the title compound. Dissolve the free base in diethyl ether (5.0 ml), ethyl acetate (6.0 ml) and methanol (1.0 ml) and add 2M HCl (1 mL, 2.0 mmol) in diethyl ether. Collect the precipitate on filter paper, rinse with diethyl ether and dry in vacuo (<2 mm of Hg) to give 310 mg (47%) of the title compound: mass spectrum (ion spray) m/z=490.3 (M–Cl).

Example 24

1-(2-{4-[2-(3-Fluoro-phenyl)-6-methoxy-naphthalen-1-yloxy]phenoxy}-ethyl)-azepane hydrochloride

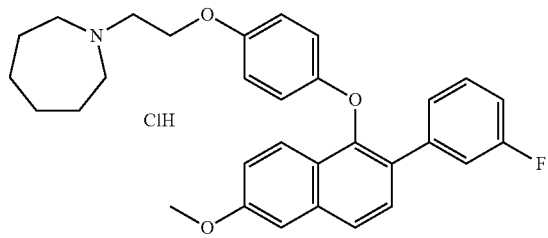

Prepare this compound following the procedure to make 1-(2-{4-[2-(3-fluoro-phenyl)-6-methoxy-naphthalen-1-yloxy]-phenoxy}-ethyl)-piperidine above, using 2-(hexamethyleneimino)-ethyl chloride hydrochloride to get a 100% yield of the free base of the title compound after radial chromatography. Form the hydrochloride salt by adding 0.8 mL of a 1 M HCl in Et$_2$O solution: mass spectrum (ion spray) m/z=4.86 (M–Cl).

Example 25

5-[4-(2-Azepan-1-yl-ethoxy)-phenoxy]-6-(3-fluoro-phenyl)-naphthalen-2-ol hydrochloride Prepare this compound following the procedure to make 6-(3-fluoro-phenyl)-5-[4-(2-piperidin-1-yl-ethoxy)-phenoxy]-naphthalen-2-ol hydrochloride above starting with 1-(2-{-4-[2-(3-fluoro-phenyl)-6-methoxy-naphthalen-1-yloxy]-phenoxy}-ethyl)-azepane hydrochloride, to get a 52% yield of the free of the title compound after radial chromatography. Form the hydrochloride salt by adding 0.8 mL of a 1 M HCl in Et$_2$O solution: mass spectrum (ion spray) m/z=472 (M–Cl).

Example 26

1-(2-{4-[6-Benzyloxy-2-(4-fluoro-phenyl)-naphthalen-1-yloxy]-phenoxy}-ethyl)-azepane

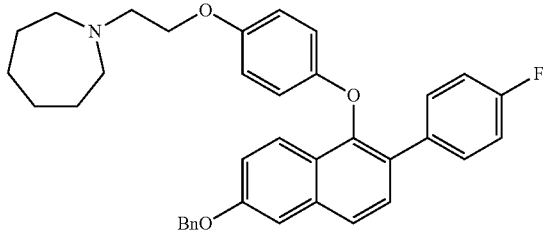

Add sodium hydride (324 mg, 8.0 mmol) into a solution of 4-[6-benzyloxy-2-(4-fluoro-phenyl)-naphthalen-1-yloxy]-phenol (1.18 g, 2.7 mmol) in DMF (10 mL) and stir for 20 minutes at room temperature. Add 2-(hexamethyleneimino) ethyl chloride hydrogen chloride (1.07 g, 5.4 mmol) and stir at room temperature for 12 hours. Add H$_2$O (10 mL) and diethyl ether (100 mL). Separate layers and wash the aqueous layer with diethyl ether (2×50 mL). Combine organic layers, dry with magnesium sulfate and concentrate in vacuo. Purify the residue over silica gel, eluting the material with a step gradient of methanol/dichloromethane (0% to 10%), to obtain 1.0 g of the title compound (66%): mass spectrum (ion spray) m/z=562.3 (M+H).

Example 27

5-[4-(2-Azepan-1-yl-ethoxy)-phenoxy]-6-(4-fluoro-phenyl)-naphthalen-2-ol hydrochloride Add ammonium formate (614 mg, 9.7 mmol) and palladium on carbon (10 mol %) into a solution of 1-(2-{4-[6-benzyloxy-2-(4-fluoro-phenyl)-naphthalen-1-yloxy]-phenoxy}-ethyl)-azepane (709 mg, 1.26 mmol) in MeOH (20 mL) and ethyl acetate (12 mL). Heat to reflux for 1 hour. Cool and filter the suspension through a pad of celite. Evaporate the solvent, dilute with CH$_2$Cl$_2$ and wash with H$_2$O (20 mL). Dry the organic layer with magnesium sulfate and concentrate in vacuo to obtain the free base of the title compound. Dissolve the free base in ethyl acetate (2 mL), diethyl ether (2 mL) and MeOH (0.1 mL). Add 2M HCl (1 mL, 20 mmol), concentrate the slurry and dry in vacuo to give the title compound (270 mg, 50% yield): mass spectrum (ion spray) 472.3 (M–Cl).

Preparation 5

Trifluoromethanesulfonic acid 6-methoxy-1-[4-(2-piperidin-1-yl-ethoxy)-benzoyl]-naphthalen-2-yl ester

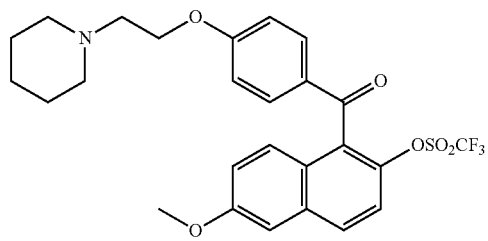

In a dry round bottom flask equipped with stir bar, temperature probe and $N_2$ line, dissolve 2,6-dimethoxynaphthalene (1.0 eq) in $CH_2Cl_2$ (5 volume equivalents) at ambient temperature. Cool the solution to 0° C. in with an ice bath, and add 4-(2-piperidin-1-yl-ethoxy)-benzoyl chloride (1.1 eq). Add aluminum chloride (2.0 eq). Once the reaction is determined to be complete, quench the reaction slowly with 1 N NaOH and dilute with additional water and $CH_2Cl_2$. Wash the aqueous layer with (1×20 mL) of $CH_2Cl_2$. Combine the organic extracts and wash with brine and dry ($Na_2SO_4$). Recrystallize the crude product from methanol to give (2,6-dimethoxy-naphthalen-1-yl)-[4-(2-piperidin-1-yl-ethoxy)-phenyl]-methasone (average yield 68%).

Dissolve (2,6-dimethoxy-naphthalen-1-yl)-[4-(2-piperidin-1-yl-ethoxy)-phenyl]-methanone in $CH_2Cl_2$ (10 volume equivalents) in a 3-neck round bottom flask equipped with a pressure equalizing addition funnel, stirbar, and $N_2$ source. Cool the flask in an ice/brine bath and add 1.0 M $BCl_3$ solution in $CH_2Cl_2$ (1.2 equivalents) dropwise. The reaction solution turns dark red and the temperature initially increases to 5° C. Within one hour, all starting material is consumed, as determined by TLC (1:1, Ether:Petroleum Ether). Quench the reaction with methanol (5 equivalents) and allow to warm to room temperature. Dilute the organic solution with $CH_2Cl_2$ (one volume equivalent) and add to a 1.0 M $NaHCO_3$ solution (5 volume equivalents) and stir for one hour. Separate the aqueous and organic layers. Wash the aqueous layer with $CH_2Cl_2$ (one volume) and the combine organic layers, wash with saturated $NH_4Cl$ and dry over $Na_2SO_4$. Purify the product via column chromatography (50/1 silica gel) eluting with $CH_2Cl_2$/Hexanes (3/1) to yield (2-hydroxy-6-methoxy-naphthalen-1-yl)-[4-(2-piperidin-1-yl-ethoxy)-phenyl]-methanone (typical yield 87%).

Dissolve (2-hydroxy-6-methoxy-naphthalen-1-yl)-[4-(2-piperidin-1-yl-ethoxy)-phenyl]-methanone in $CH_2Cl_2$ (10 volumes) in a three neck round bottom flask equipped with a stir bar and $N_2$ source and chill to 0° C. in an ice/brine bath. Add pyridine (1.3 equivalents). Add trifluoromethane sulfonyl chloride (1.2 equivalents) via syringe over 15 minutes. After 15 minutes, quench the reaction with $H_2O$ (10 volumes), wash with 1 N HCl (5 volumes), wash with 1.0 N $NaHCO_3$, and dry over $Na_2SO_4$. Concentrate to give the title compound in quantitative yield. Use the product without further purification.

Example 28

[2-(2,4-Difluoro-phenyl)-6-methoxy-naphthalen-1-yl]-[4-(2-piperidin-1-yl-ethoxy)-phenyl]-methanone

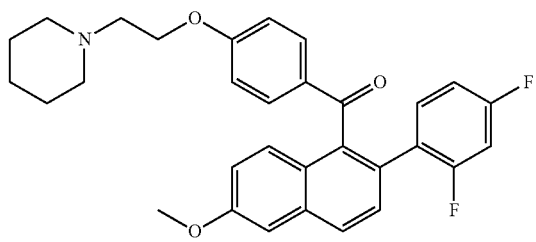

Dissolve trifluoromethanesulfonic acid 6-methoxy-1-[4-(2-piperidin-1-yl-ethoxy)-benzoyl]-naphthalen-2-yl ester (12.4 g, 23.0 mmol) and 2,4-difluorophenylboronic acid (7.0 g, 46.0 mmol) in degassed dimethoxyethane (620 mL). Add 2M aqueous sodium carbonate (73 mL, 145 mmol) and stir at room temperature under nitrogen for 5 minutes. Add palladium(II) acetate (520 mg, 2.3 mmol) and triphenylphosphine (1.2 g, 4.6 mmol) and plunge into a 85° C. oil bath. Stir for 40 minutes and cool to room temperature. Pour into saturated aqueous sodium bicarbonate and extract twice with methylene chloride. Dry the combined organic layers with sodium sulfate, filter and concentrate in vacuo. Purify the resultant oil with SCX columns (load in methanol, elute with 2M $NH_3$/MeOH) to yield 10.8 g (93%) of the title compound: mass spectrum (ion spray) m/z=502.3 (M+H).

Example 29

[2-(2,4-Difluoro-phenyl)-6-hydroxy-naphthalen-1-yl]-[4-(2-piperidin-1-yl-ethoxy)-phenyl]-methanone hydrochloride Dissolve [2-(2,4-difluoro-phenyl)-6-methoxy-naphthalen-1-yl]-[4-(2-piperidin-1-yl-ethoxy)-phenyl]-methanone (10.8 g, 21.5 mmol) in methylene chloride (200 mL). Add 2M HCl in ether (21.5 mL, 43 mmol) and concentrate in vacuo. Redissolve the foam in methylene chloride (200 mL) and cool to 0° C. under nitrogen. Slowly add boron tribromide (10.1 mL, 107 mmol) and stir at 0° C. for 30 minutes. Slowly pour into saturated aqueous sodium bicarbonate and extract with 20% WA in chloroform. Dry the organic layer with sodium sulfate, filter and concentrate in vacuo to yield 10.5 g (100%) of the free base of the title compound: $^1$H-NMR (CDCl$_3$) δ 57.72 (d, J=8.6 Hz, 1H), 7.49 (d, J=8.6 Hz, 3H), 7.35 (d, J=8.4 Hz, 1H), 7.18 (t, J=7.8 Hz, 1H), 7.14 (d, J=1.9 Hz, 1H), 6.96 (dd, J=9.2, 2.3 Hz, 1H), 6.74-6.62 (m, 2H), 6.58 (d, J=8.6 Hz, 2H), 4.08 (t, J=5.9 Hz, 2H), 2.79 (t, J=5.6 Hz, 2H), 2.55 (bs, 4H), 1.63 (bs, 4H), 1.45 (m, 2H). Dissolve the free base in a 1:1 mixture of acetonitrile:water. Add an appropriate amount of 5 M hydrochloric acid and lyophilize the mixture to afford the title compound.

Example 30

[2-(2,5-Difluoro-phenyl)-6-methoxy-naphthalen-1-yl]-[4-(2-piperidin-1-yl-ethoxy)-phenyl]-methanone

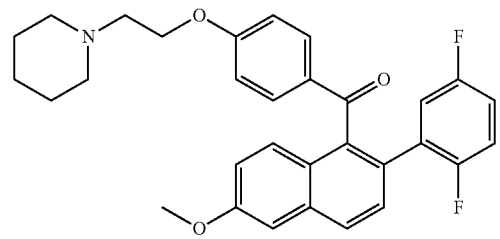

Dissolve trifluoromethanesulfonic acid 6-methoxy-1-[4-(2-piperidin-1-yl-ethoxy)-benzoyl]-naphthalen-2-yl ester (4.51 g, 8.4 mmol) in acetonitrile (140 mL). Add Pd(OAc)$_2$ (0.28 g, 1.3 mmol), tricyclohexylphosphine (0.59 g, 2.1 mmol), cesium fluoride (11.4 g, 75.6 mmol) and 2,5-difluorobenzeneboronic acid (2.56 g, 16.2 mmol). Flush the flask with nitrogen then heat the reaction mixture to 90° C. Heat the reaction mixture for one hour and then cool it to room temperature. Add water (400 mL) and extract the aqueous layer with methylene chloride (3×400 mL). Combine the organic layers and dry with sodium sulfate, filter, concentrate and purify by flash column chromatography (0-4% MeOH—NOH (10/1, v/v)/CH$_2$Cl$_2$) to give 2.42 g (68%) of the title compound: mass spectrum (ion spray) m/z=502.3 (M+H).

Example 31

[2-(2,5-Difluoro-phenyl)-6-hydroxy-naphthalen-1-yl]-[4-(2-piperidin-1-yl-ethoxy)-phenyl]-methanone hydrochloride Demethylate[2-(2,5-difluoro-phenyl)-6-methoxy-naphthalen-1-yl]-[4-(2-piperidin-1-yl-ethoxy)-phenyl]-methanone (2.42 g, 4.82 mmol) with BBr$_3$ in a procedure similar to the preparation of 2-(2,4-difluoro-phenyl)-6-hydroxy-naphthalen-1-yl]-[4-(2-piperidin-1-yl-ethoxy)-phenyl]-methanone to give 1.96 g (83%) of the free base of the title compound: mass spectrum (ion spray) m/z=488.3 (M+H). Dissolve the free base in a 1:1 mixture of acetonitrile:water. Add an appropriate amount of 5 M hydrochloric acid and lyophilize the mixture to afford the title compound.

Example 32

Methanesulfonic acid 6-(2,4-difluoro-phenyl)-5-[4-(2-piperidin-1-yl-ethoxy)-benzoyl]-naphthalen-2-yl ester

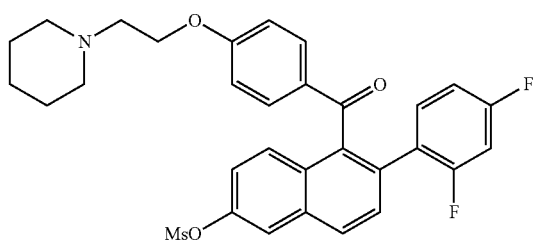

Dissolve [2-(2,4-difluoro-phenyl)-6-hydroxy-naphthalen-1-yl]-[4-(2-piperidin-1-yl-ethoxy)-phenyl]-methanone (540 mg, 1.11 mmoles), and methane sulfonyl chloride (254 mg, 2.22 mmoles) in 10 ml acetonitrile and add triethylamine (224 mg, 2.22 mmoles). Stir the mixture for 5 days at room temp. Add equivalent amounts of the sulfonyl chloride and triethylamine and stir for 30 minutes. Evaporate the mixture to dryness, dissolve in methanol and pass through an SCX column. Wash the column with methanol and elute the product with 2 N ammonia/methanol to yield 433 mg (69%) of the title compound: mass spectrum (ion spray) m/z=566 (M+H).

Example 33

[2-(2,6-Difluoro-phenyl)-6-methoxy-naphthalen-1-yl]-[4-(2-piperidin-1-yl-ethoxy)-phenyl]-methanone

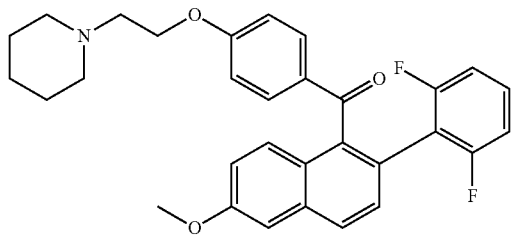

Charge a flask with trifluoromethanesulfonic acid 6-methoxy-1-[4-(2-piperidin-1-yl-ethoxy)-benzoyl]-naphthalen-2-yl ester (2.0 g, 3.7 mmol), 2,6-difluorophenyl boronic acid (1.17 g, 7.4 mmol), tetrakis(triphenylphosphine)palladium (0) (855 mg, 0.74 mmol) and potassium phosphate (4.7 g, 22.2 mmol) add 100 mL, of dry DMF and heat under nitrogen at 100° C. for two hours. Cool the reaction and filter. Purify on an SCX column eluting with 2N ammonia/methanol. Purify further on a silica gel column eluting with a gradient of 0-10% methanol/methylene chloride. The yield is 1.5 g (81%): 1H-NMR (CDCl$_3$, 400 MHz) δ 7.90 (d, J=8.4 Hz, 1H); 7.63 (d, J=8.4 Hz, 1H); 7.62 (d, J=9.2 Hz, 2H); 7.39 (d, J=8.4 Hz, 1H); 7.23 (d, J=2.8 Hz, 1H); 7.18-7.08 (m, 2H); 6.78 (d, J=10.4 Hz, 2H); 6.74 (s, 2H); 4.11-4.08 (m, 2H); 3.95 (s, 3H); 2.75 (t, J=6.4 Hz, 2H); 2.49-2.49 (m, 4H); 1.63-1.58 (m, 4H); 1.47-1.44 (m, 2H).

Example 34

[2-(2,6-Difluoro-phenyl)-6-hydroxy-naphthalen-1-yl]-[4-(2-piperidin-1-yl-ethoxy)-phenyl]-methanone Dissolve [2-(2,6-difluorophenyl)-6-methoxy-naphthalen-1-yl]-[4-(2-piperidin-1-ylethoxy)-phenyl]-methanone (1.5 gm., 3.0 mmoles) in 500 ml methylene chloride and chill in ice. To this solution add boron tribromide (6.0 ml, 63 mmoles) in portions with swirling between additions. Allow to come to room temp. and stir for one hour. Pour into a two-phase system consisting of an organic layer of 3/1 chloroform/isopropanol and an aqueous layer of saturated sodium bicarbonate. Separate the phases and dry the organic layer using 3A molecular sieves. Purify on a silica column eluting with a 0-10% methanol/methylene chloride gradient. The yield of pure product is 600 mg (44%): 1H-NMR (CD$_3$OD, 400 MHz) δ7.87 (d, J=8.0 Hz, 1H); 7.56 (d, J=8.4 Hz, 2H); 7.49 (d, J=9.2 Hz, 1H); 7.33 (d, j=8.8 Hz, 1H); 7.27-7.25 (m, 1H); 7.23-7.21 (m, 1H); 7.06 (dd, J=8.8, 2.4 Hz, 1H); 6.86-6.79 (m, 4H); 4.14 (t, J=5.6 Hz, 2H); 2.76 (t, J=5.6 Hz, 2H); 2.53-2.53 (m, 4H); 1.65-1.59 (m, 4H); 1.50-1.46 (m, 2H).

Preparation 6

Trifluoromethanesulfonic acid 6-benzyloxy-1-[4-(2-piperidin-1-yl-ethoxy)-benzoyl]-naphthalen-2-yl ester

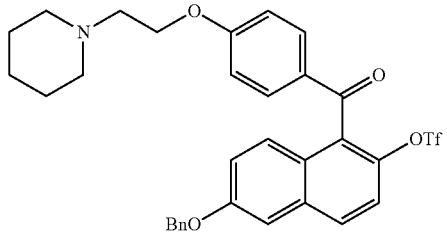

Dissolve trifluoromethanesulfonic acid 6-hydroxy-1-[4-(2-piperidin-1-yl-ethoxy)-benzoyl]-naphthalen-2-yl ester (9.00 g, 17.2 mmol) in THF (540 mL). Stir the solution at 0° C. under $N_2$ and add benzyl alcohol (2.78 g, 25.8 mmol), polymer-$PPh_3$ (8.60 g, 25.8 mmol) and DIAD (5.21 g, 25.8 mmol). Continue to stir the reaction mixture at room temperature for 2 hours. Add water (1000 mL), and extract the aqueous layer with $CH_2Cl_2$ (3×500 mL). Combine the organic layers and dry with $Na_2SO_4$, filter, concentrate and purify by flash chromatography (silica gel, 0-4% MeOH—$NH_4OH$ (10/1, v/v)/$CH_2Cl_2$) to give 10.0 g (96%) of the title compound: mass spectrum (ion spray) m/z=614.1 (M+H).

Example 35

[6-Benzyloxy-2-(2-fluoro-phenyl)-naphthalen-1-yl]-[4-(2-piperidin-1-yl-ethoxy)-phenyl]-methanone

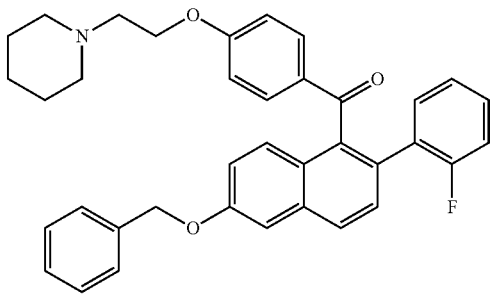

Dissolve trifluoromethanesulfonic acid 6-benzyloxy-1-[4-(2-piperidin-1-yl-ethoxy)-benzoyl]-naphthalen-2-yl ester (1.00 g, 1.63 mmoles) in 20 ml of acetonitrile and add 2-fluorobenzene boronic acid (0.46 g, 3.26 mmoles), trans[dichlorobis(triphenylphosphine)]palladium II (0.23 gm., 0.33 mmoles) and sonicate briefly. Next add cesium fluoride (2.23 g, 14.67 mmol) and heat to 75° C. for one hour. Add Celite and filter. Concentrate the solvent under vacuum, dissolve in methanol and purify on an SCX cartridge, eluting with 2N ammonia/methanol. Further purify on a silica gel column eluting with a 0-10% methanol/methylene chloride gradient to isolate 550 mg of the title compound (60%).

Example 36

[2-(2-Fluoro-phenyl)-6-hydroxy-naphthalen-1-yl]-[4-(2-piperidin-1-yl-ethoxy)-phenyl]-methanone hydrochloride Dissolve [6-benzyloxy-2-(2-fluoro-phenyl)-naphthalen-7-yl]-[4-(2-piperidin-1-yl-ethoxy)-phenyl]-methasone (0.55 g, 0.98 mmoles) in 25 ml of ethanol and after a nitrogen purge add 10% palladium on carbon (60 mg) and hydrogen (1 atm). After 12 hours, filter over celite and concentrate the solvent under vacuum, purify on a silica gel column eluting with a 0-10% methanol/methylene chloride gradient to isolate 350 mg of the title compound (76%). Convert to the hydrochloride salt to give the title compound.

Example 37

[6-Methoxy-2-(2,4,6-trifluoro-phenyl)-naphthalen-1-yl]-[4-(2-piperidin-1-yl-ethoxy)-phenyl]-methanone

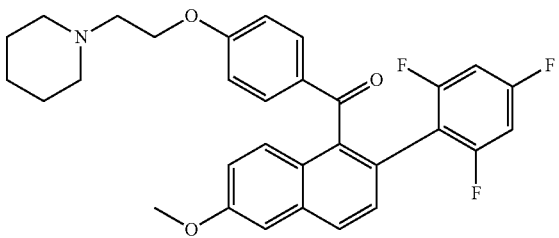

Dissolve trifluoromethanesulfonic acid 6-methoxy-1-[4-(2-piperidin-1-yl-ethoxy benzoyl]-naphthalen-2-yl ester (752 mg, 1.4 mmol), 2,4,6-trifluorophenylboronic acid (493 mg, 2.8 mmol), potassium phosphate (1.8 g, 8.4 mmol)) and tetrakis(triphenylphosphine)palladium (324 mg, 0.3 mmol) in dry DMF (25 mL) and heat at 100° C. for 20 minutes. Purify reaction on an SCX column to yield 674 mg (93%) of the title compound: mass spectrum (ion spray) m/z=520.2 (M+H).

Example 38

[6-Hydroxy-2-(2,4,6-trifluoro-phenyl)-naphthalen-1-yl]-[4-(2-piperidin-1-yl-ethoxy)-phenyl]-methanone Dissolve [6-methoxy-2-(2,4,6-trifluoro-phenyl)-naphthalen-1-yl]-[4-(2-piperidin-1-yl-ethoxy)-phenyl]-methanone (670 mg, 1.3 mmol) in dichloromethane (10 mL). Cool to 0° C., add 2M HCl (1.3 mL, 2.6 mmol) and stir at room temperature for 15 minutes. Concentrate in vacuo. Redissolve the salt in dichloromethane (10 mL) and cool to 0° C. Add boron tribromide (1.1 g, 3.9 mmol) dropwise and bring to room temperature. Stir reaction for 1.5 hours and pour reaction mixture onto ice, saturated sodium bicarbonate (10 mL) and methanol (10 mL). Extract with dichloromethane, combine extracts and wash with water and saturated sodium bicarbonate. Dry with sodium sulfate, filter, and concentrate in vacuo. Purify by silica gel chromatography using a 1-3% gradient of methanol in dichloromethane to yield 454 mg (70%) of the title compound: mass spectrum (ion spray) m/z=506.3 (M+H).

Preparation 7

Trifluoromethanesulfonic acid 6-methanesulfonyloxy-1-[4-(2-piperidin-1-yl-ethoxy)-benzoyl]-naphthalen-2-yl ester

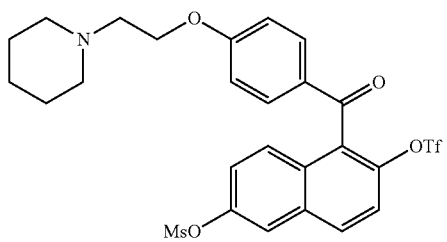

Suspend trifluoromethanesulfonic acid 6-hydroxy-1-[4-(2-piperidin-1-yl-ethoxy)-benzoyl]-naphthalen-2-yl ester (12.5 g, 24 mmol) in dry methylene chloride (100 ml). Add diisopropylethylamine (8.3 mL, 48 mmol). Slowly add methanesulfonyl chloride (2.7 mL, 36 mmol). Pour reaction into saturated aqueous sodium bicarbonate after 20 minutes and extract with methylene chloride. Wash the organic layer with water, dry with sodium sulfate, filter and concentrate in vacuo to yield 14.2 g (99%) of the title compound.

Example 39

[6-Hydroxy-2-(2,3,5-trifluoro-phenyl)-naphthalen-1-yl]-[4-(2-piperidin-4-yl-ethoxy)-phenyl]-methasone

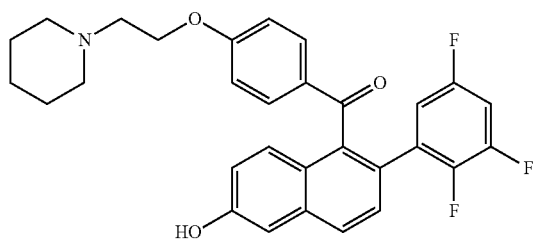

Dissolve trifluoromethanesulfonic acid 6-methanesulfonyloxy-1-[4-(2-piperidin-1-yl-ethoxy)-benzoyl]-naphthalen-2-yl ester (7.0 g, 11.6 mmol) in degassed acetonitrile (100 mL). Add cesium fluoride (9.1 g, 58 mmol) and bis(acetato)bis(triphenylphosphine)palladium (0.87 g, 1.2 mmol) followed by bis(neopentyl glycolato)diboron (3.1 g, 13.9 mmol) and plunge into a 75° C. oil bath under nitrogen. After 15 minutes, add 1-bromo-2,3,5-trifluorobenzene (4.9 g, 23.2 mmol) to the reaction and bis(acetato)bis(triphenylphosphine)palladium (200 mg) and stir at 75° C. for 2.5 hours. Cool the reaction to room temperature and filter through celite. Concentrate the filtrate in vacuo and redissolve the residue in methanol (100 mL). Add KOH (5 g) and stir at room temperature overnight. Pour the reaction into saturated aqueous ammonium chloride and extract with methylene chloride. Dry the organic layer with sodium sulfate, filter and concentrate in vacuo. Purify on silica gel (0% to 6% methanol in methylene chloride) to obtain 3.7 g (64%) of the title compound: mass spectrum (ion spray) m/z=506.3 (M+H).

Example 40

[6-Methoxy-2-(2,3,6-trifluoro-phenyl)-naphthalen-1-yl]-[4-(2-piperidin-1-yl-ethoxy)-phenyl]-methanone

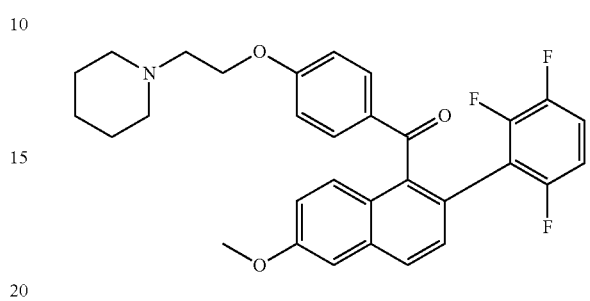

Couple trifluoromethanesulfonic acid 6-methoxy-1-[4-(2-piperidin-1-yl-ethoxy)-benzoyl]-naphthalen-2-yl ester (1.81 g, 3.37 mmol) with 2-bromo-1,3,4-trifluoro-benzene (1.42 g, 6.75 mmol) in a procedure similar to the preparation of 6-hydroxy-2-(2,3,5-trifluoro-phenyl)-naphthalen-1-yl]-[4-(2-piperidin-1-yl-ethoxy)-phenyl]-methanone to give 0.79 g (45%) of the title compound: mass spectrum (ion spray) m/z=520.3 (M+H).

Example 41

[6-Hydroxy-2-(2,3,6-trifluoro-phenyl)-naphthalen-1-yl]-[4-(2-piperidin-1-yl-ethoxy)-phenyl]-methanone Demethylate[6-methoxy-2-(2,3,6-trifluoro-phenyl)-naphthalen-1-yl]-[4-(2-piperidin-1-yl-ethoxy)-phenyl]-methanone (0.79 g, 1.52 mmol) with $BBr_3$ in a procedure similar to the preparation of 2-(2,4-difluoro-phenyl)-6-hydroxy-naphthalen-1-yl]-[4-(2-piperidin-1-yl-ethoxy)-phenyl]-methanone to give 0.67 g (88%) of the title compound: mass spectrum (ion spray) m/z=506.3 (M+H).

Example 42

[6-Methoxy-2-(2,3,4-trifluoro-phenyl)-naphthalen-1-yl]-[4-(2-piperidin-1-yl-ethoxy)-phenyl]-methanone

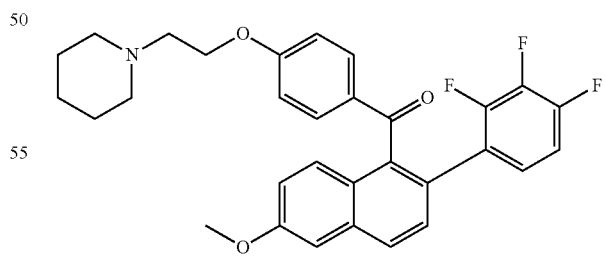

Charge a flask with trifluoromethanesulfonic acid 6-methoxy-1-[4-(2-piperidin-1-yl-ethoxy)-benzoyl]-naphthalen-2-yl ester (2.13 g, 4.0 mmol), 2,3,4-trifluorophenyl boronic acid (1.0 g, 5.7 mmol), trans-dichlorobis(triphenylphosphine)palladium II, (561 mg, 0.8 mmol) and cesium fluoride (5.5 g, 36 mmol) and add 50 mL of acetonitrile. Heat the mixture at 80° C. for 4 hours. Cool and filter the mixture and purify on an SOX column, eluting with 2N ammonia/ethanol. Purify further on a silica column eluting with 2% 2N ammonia/methanol/methylene chloride to give 880 mg (43%) of the title compound: $^1$H-NMR (CD$_3$OD, 400 MHz) δ 7.93 (d, J=8.8 Hz, 1H); 7.50 (d, J=8.4 Hz, 3H); 7.39 (d, J=8.8 Hz, 1H); 7.35 (d, J=2.4 Hz, 1H); 7.07 (dd, J=9.2, 2.8 Hz, 1H); 6.96-6.87 (m, 2H); 6.80 (d, J=9.6 Hz, 2H); 4.10-4.07 (t, 2H); 3.91 (s, 3H); 2.72-2.69 (t, 2H); 2.48-2.48 (m, 4H); 1.61-1.55 (m, 4H); 1.46-1.43 (m, 2H).

Example 43

[6-Hydroxy-2-(2,3,4-trifluoro-phenyl)-naphthalen-1-yl]-[4-(2-piperidin-1-yl-ethoxy)-phenyl]-methanone Dissolve [6-methoxy-2-(2,3,4-trifluoro-phenyl)-naphthalen-1-yl]-[4-(2-piperidin-1-yl-ethoxy)-phenyl]-methanone (880 mg, 1.69 mmol) in 100 mL methylene chloride and chill in ice. Add 4.0 mL of neat boron tribromide with swirling and stir in the ice bath for 30 minutes. Allow the mixture to come to room temp and stir for an additional 1 hour. Carefully pour the mixture into a two-phase system consisting of saturated sodium bicarbonate solution and a 3/1 mixture of chloroform/isopropanol. Separate the organic layer, dry over 3 Å molecular sieves and evaporate to give 800 mg of slightly impure product. Purify on a silica gel column eluting with 3% methanol/methylene chloride to give 635 mg (74%) of the title compound: 1H-NMR (CD$_3$OD, 400 MHz) δ7.89 (d, J=8.8 Hz, 1H); 7.69-7.42 (m, 4H); 7.45-7.42 (m, 1H); 7.31 (d, J=2.4 Hz, 1H); 7.14 (dd, J=9.2, 2.4 Hz, 1H); 7.02-6.87 (m, 3H); 4.20 (t, J=5.6 Hz, 2H); 2.84 (t, J=5.6 Hz, 2H); 2.59-2.59 (m, 4H); 1.71-1.65 (m, 4H); 1.56-1.53 (m, 2H).

Example 44

[2-(2,3-Difluoro-phenyl)-6-hydroxy-naphthalen-1-yl]-[4-(2-piperidin-1-yl-ethoxy)-phenyl]-methanone

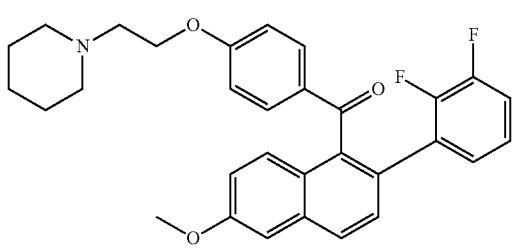

Charge a flask with trifluoromethanesulfonic acid 6-methoxy-1-[4-(2-piperidin-1-yl-ethoxy)-benzoyl]-naphthalen-2-yl ester (2.0 g, 3.7 mmol), 2,3 difluorophenyl boronic acid (1.17 g, 7.4 mmol) palladium dichloride bis(triphenylphosphine) (518 mg, 0.74 mmol) and cesium fluoride (5.06 g, 33.3 mmol) and add 250 mL degassed acetonitrile. Heat the mixture at 85° C. for two hours, cool the reaction and filter off any solids. Purify on an SCX column eluting with 2N ammonia/methanol. Purify further on a silica gel column eluting with a 0-10% methanol/methylene chloride gradient to give 1.3 g (70%) of the title compound: 1H-NMR (CD$_3$OD, 400 MHz) δ7.92 (d, J=8.8 Hz, 1H); 7.54 (dd, J=8.4, 4.0 Hz, 3H); 7.43 (dd, J=8.4, 1.6 Hz, 1H); 7.31 (d, J=2.8 Hz, 1H); 7.09 (dd, J=9.2, 2.4 Hz, 1H); 7.05-6.92 (m, 3H); 6.79 (d, J=8.8 Hz, 2H); 4.10 (t, J=5.6 Hz, 2H); 3.93 (s, 3H); 2.73 (t, J=5.2 Hz, 2H); 2.50-2.50 (m, 4H); 1.62-1.57 (m, 4H); 1.48-1.43 (m, 2H).

Example 45

[2-(2,3-Difluoro-phenyl)-6-hydroxy-naphthalen-1-yl]-[4-(2-piperidin-1-yl-ethoxy)-phenyl]-methanone Charge a flask with [2-(2,3-difluoro-phenyl)-6-hydroxy-naphthalen-1-yl]-(4-(2-piperidin-1-yl-ethoxy)-phenyl]-methanone (1.3 g, 2.6 mmol) and add 200 mL methylene chloride followed by 25 ml of HCl/ether and evaporate to dryness. Dissolve the solid in 200 mL methylene chloride and chill the solution in ice. Add to this solution boron tribromide (4.0 mL, 42.4 mmol) with swirling. Stir the solution at room temperature for 1 hour at which point all the starting material is gone. Pour this into a two phase mixture consisting of saturated sodium bicarbonate aqueous phase and a 3/1 mixture of chloroform/isopropanol organic phase and extract using a separatory funnel. Separate the organic phase and dry over 3 Å molecular sieves. Purify on a silica column eluting with 0-10% methanol/methylene chloride, collecting the fast fraction that contains the product to give 400 mg (32%) of the title compound: 1H-NMR (CD$_3$OD, 400 MHz) δ7.84 (d, J=8.4 Hz, 1H); 7.55 (d, J=9.2 Hz, 2H); 7.50 (d, J=8.8 Hz, 1H); 7.40 (dd, J=9.2, 1.6 Hz, 1H); 7.25 (d, J=2.4 Hz, 1H); 7.10-7.03 (m, 2H); 6.99-6.95 (m, 2H); 6.83 (d, J=9.2 Hz, 2H); 4.12 (t, J=5.2 Hz, 2H); 2.76-2.73 (m, 2H); 2.58-232 (m, 4H); 1.64-1.58 (m, 4H); 1.49-1.45 (m, 2H).

Preparation 8

6-Hydroxy-1-[4-(2-piperidin-1-yl-ethoxy)-benzoyl]-naphthalen-2-yl ester

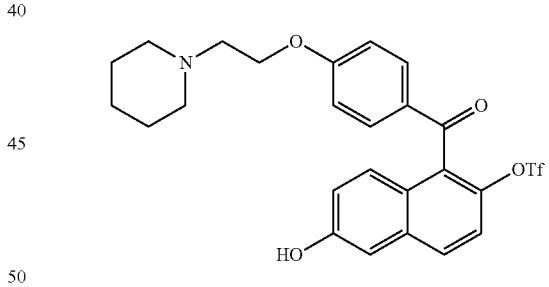

Dissolve trifluoromethanesulfonic acid 6-methoxy-1-[4-(2-piperidin-1-yl-ethoxy)-benzoyl]-naphthalen-2-yl ester (240 g, 430 mmol) in dichloroethane (1.5 L). Cool to 0° C. Bubble hydrogen chloride (36 g, 1 mol) into the reaction. Condense boron trichloride (250 g, 2.1 mol) into a jacketed addition funnel and add dropwise into the reaction. Stir 48-72 h. Carefully add reaction to a mixture of 5 M sodium hydroxide (700 mL), water (500 mL), and dichloromethane (1 L) at 0° C. Adjust pH to 7 with 50% aqueous sodium hydroxide. Dilute with 1 M sodium bicarbonate (1.7 L) and dichloromethane (500 mL). Separate organic. Wash aqueous with dichloromethane (1 L). Combine organics and dry over magnesium sulfate, filter, and concentrate in vacuo. Slurry material in dichloromethane (200 mL) and obtain 196.2 g of the title compound (87%).

Example 46

[2-(3-Fluoro-phenyl)-6-hydroxy-naphthalen-1-yl]-4-(2-piperidin-1-yl-ethoxy)-phenyl]-methanone hydrochloride

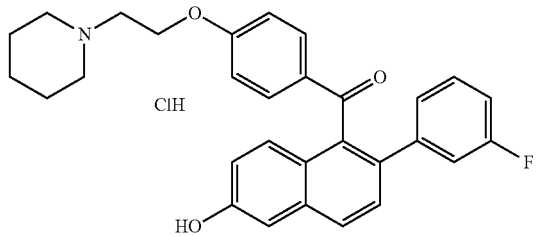

Charge a flask with trifluoromethanesulfonic acid 6-hydroxy-1-[4-(2-piperidin-1-yl-ethoxy)-benzoyl]-naphthalen-2-yl ester (500 mg, 0.96 mmol) and add 10 mL, water along with 2 mL of 1,2 dimethoxyethane. To this add 3-fluorophenylboronic acid (270 mg, 1.91 mmol), transdichlorobis(triphenylphosphine) palladium II (130 mg, 0.19 mmol) and sodium carbonate (920 mg, 8.64 mmol). Heat the mixture to 80° C. and hold for one hour. Cool and filter the mixture and purify on an SCX column, eluting with 2N ammonia/methanol. Concentrate and purify on a silica column eluting with a 0-10% 2N ammonia in methanol/methylene chloride gradient. Concentrate and convert to the HCl salt: 1H-NMR (CDCl$_3$, 300 MHz) δ 7.76 (d, J=8.7 Hz, 1H); 7.52-7.41 (m, 5H); 7.21-6.96 (m, 4H); 6.89-6.86 (m, 1H); 6.52 (d, J=9.0 Hz, 2H); 4.09-4.05 (t, 2H); 2.78-2.78 (m, 2H); 2.56 (s, 4H); 1.67-1.63 (m, 4H); 1.48-1.46 (m, 2H).

Preparation 9

Trifluoromethanesulfonic acid 1-[4-(2-azepan-1-yl-ethoxy)-benzoyl]-6-methoxynaphthalen-2-yl ester

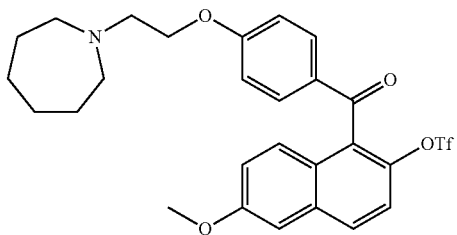

Dissolve 4-(2-azepan-1-yl-ethoxy)-benzoyl chloride (79.4 g, 249 mmol) and 2,6-dimethoxynaphthalene (37.8 g, 201 mmol) in dichloromethane (800 ml). Cool to −5° C. and add aluminum trichloride (134 g, 1 mol). Warm to room temperature and stir overnight. Add chilled water (1.5 L) and stir vigorously for 1 hour. Decant the mixture away from the residue and separate organic. Wash the aqueous layer with dichloromethane (500 mL). Combine with residue from the reaction vessel and wash with saturated aqueous sodium bicarbonate (1 L). Separate the organic after prolonged stirring (2 hours) and wash the aqueous layer with dichloromethane (300 mL). Combine the organic layers and add Darco (30 g), silica gel (30 g), and magnesium sulfate. Filter and concentrate in vacuo to give 72.4 g of [4-(2-azepan-1-yl-ethoxy)-phenyl]-(2-hydroxy-6-methoxy-naphthalen-1-yl)-methanone (73%).

Dissolve [4-(2-azepan-1-yl-ethoxy)-phenyl]-(2-hydroxy-6-methoxy-naphthalen-1-yl)-methanone (41.0 g, 88.0 mmol) and triethylamine (28.8 g, 284 mmol) in dichloromethane (400 mL). Cool to −60° C. and add trifluoromethanesulphonic anhydride (39.8 g, 141 mmol) in dichloromethane (100 mL). Warm to room temperature and stir. Dilute with saturated aqueous sodium bicarbonate (500 mL) and separate the organic. Wash the aqueous with dichloromethane (200 mL). Combine the organics and wash with saturated aqueous sodium chloride. Dry over magnesium sulfate, filter, and concentrate in vacuo. Purify the residue by column chromatography using a silica gel column eluting with a linear gradient beginning with dichloromethane and ending with 30:1 dichloromethane:methanol to give 48.6 g of the title compound (96%).

Alternative Synthesis of Trifluoromethanesulfonic acid 1-[4-(2-azepan-1-yl-ethoxy)-benzoyl]-6-methoxynaphthalen-2-yl ester Add sodium hydride (18 g, 0.45 mol) into a solution of 4-benzyloxyphenol (41 g, 0.20 mol) and 2-(hexamethyleneimino)ethyl chloride hydrochloride (44 g, 0.22 mmol) in THF (600 mL) and DMF (100 mL) at room temperature. Heat to 60° C. for 30 minutes. Pour the solution into ice and water. Dilute with ethyl acetate (500 mL) and separate layers. Dry the organic layer with magnesium sulfate, filter and concentrate under reduced pressure to give brown oil. Dissolve the oil in ethyl acetate (500 mL) and methanol (500 mL). Add ammonium formate (100 g, 1.59 mol) and palladium on carbon (10 g, 9.4 mmol). Heat the mixture to reflux for 30 minutes. Add ammonium formate (100 g, 1.59 mol) and palladium on carbon (10 g, 9.4 mmol). Heat the reaction mixture for 30 minutes. Filter the suspension through a pad of celite and elute with ethyl acetate (500 ml). Evaporate solvent under reduced pressure and add water (100 mL). Dilute the mixture with ethyl acetate (500 mL) and separate layers. Wash the organic layer with saturated sodium bicarbonate solution (2×200 mL), dry with magnesium sulfate, filter and evaporate solvent under reduced pressure to give 31 g (64%) of 4-(2-azepan-1-yl-ethoxy)-phenol.

Combine 2-benzyloxy-1-bromo-6-methoxy-naphthalene (31 g, 90 mmol), 4-(2-azepan-1-yl-ethoxy)-phenol (31 g, 132 mmol), copper bronze (12 g, 189 mmol), potassium carbonate (25 g, 181 mmol) and pyridine (400 mL). Heat the reaction mixture to reflux for 85 hours. Cool and filter the residue with celite and elute with methanol and methylene chloride (500 mL, V/V=1:5). Evaporate solvent under reduced pressure and chromatograph the residue on a silica gel column eluting the material with a step gradient of methanol/dichloromethane (0 to 10%) to get 19 g (43%) of 1-{2-[4-(2-benzyloxy-6-methoxy-naphthalen-1-yloxy)-phenoxy]-ethyl}-azepane. Dissolve 1-{2-[4-(2-benzyloxy-6-methoxy-naphthalen-1-yloxy)-phenoxy]-ethyl}-azepane (19 g, 38 mmol) in ethyl acetate (500 mL) and methanol (600 mL). Heat the mixture to obtain a clear solution. Cool to room temperature. Add ammonium formate (30 g, 476 mmol) and palladium on carbon (2 g, 1.9 mmol). Heat to reflux for 30 minutes. Add ammonium formate (7 g, 111 mmol) and palladium on carbon (0.7 g, 0.7 mmol). Heat to reflux for 30 minutes. Filter the suspension through a pad of celite and elute with ethyl acetate (500 mL). Evaporate solvent under reduced pressure and add water (100 mL). Dilute the mixture with ethyl acetate (500 mL) and separate layers. Wash the organic layer with saturated sodium bicarbonate solution (2×200 mL), dry with magnesium sulfate, filter and evaporate solvent under reduced pressure to give 15.1 g (97%) of 1-[4-(2-azepan-1-yl-ethoxy)-phenoxy]-6-methoxy-naphthalen-2-ol.

Add trifluoromethanesulfonic anhydride (7 mL, 42 mmol) into a solution of 1-[4-(2-azepan-1-yl-ethoxy)-phenoxy]-6-methoxy-naphthalen-2-ol (15 g, 37 mmol), triethylamine (20 mL) and methylene chloride (500 mL) at −50° C. Warm the reaction mixture to room temperature and stir for 1 hour at that temperature. Cool the reaction mixture to −78° C. and add brine (20 mL). Warm the reaction to room temperature. Separate layer and wash the organic layer with saturated sodium bicarbonate solution (100 mL) and brine. Dry the organic layer with magnesium sulfate, filter and evaporate solvent under reduced pressure. Chromatograph the residue on a silica gel column eluting the material with a step gradient of methanol/dichloromethane (0 to 10%) to get 20 g (99%) of trifluoro-methanesulfonic acid 1-[4-(2-azepan-1-yl-ethoxy)-phenoxy]-6-methoxy-naphthalen-2-yl ester.

Example 47

[4-(2-Azepan-1-yl-ethoxy)-phenyl]-[6-methoxy-2-(2,4,6-trifluoro-phenyl)-naphthalen-1-yl]-methanone

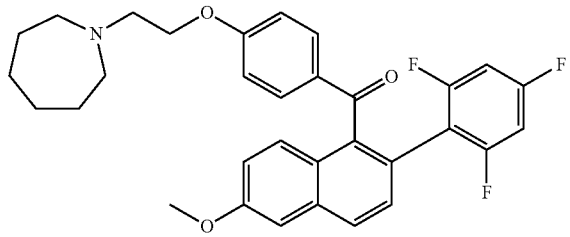

Dissolve trifluoromethanesulfonic acid 1-[4-(2-azepan-1-yl-ethoxy)-benzoyl]-6-methoxy-naphthalen-2-yl ester (990 mg, 1.8 mmol), 2,4,6-trifluorophenylboronic acid (634 mg, 3.6 mmol), potassium phosphate (2.2 g, 10.8 mmol), tetrakis (triphenylphosphine)palladium (416 mg, 0.4 mmol) in dry DMF (25 mL) and heat at 100° C. for 3 hours. Purify reaction by SCX column and by silica gel chromatography using a 1-3% gradient of methanol in dichloromethane to yield 320 mg (35%) of the title compound: mass spectrum (ion spray) m/z=534 (M+H).

Example 48

[4-(2-Azepan-1-yl-ethoxy)-phenyl]-[6-hydroxy-2-(2,4,6-trifluoro-phenyl)-naphthalen-1-yl]-methanone Dissolve [4-(2-azepan-1-yl-ethoxy)-phenyl]-[6-methoxy-2-(2,4,6-trifluoro-phenyl)-naphthalen-1-yl]-methanone (634 mg, 1.2 mmol) in dichloromethane (10 mL). Cool to 0° C., add HCl (2M in ether, 1.2 mL, 2.4 mmol) and stir at room temperature for 15 minutes. Concentrate in vacuo. Redissolve the salt in dichloromethane (10 mL) and cool to 0° C. Add boron tribromide (949 mg, 3.6 mmol) dropwise and bring to room temperature. Stir reaction for 1.5 hour and pour reaction mixture onto ice, saturated sodium bicarbonate (20 mL) and methanol (20 mL). Extract with dichloromethane, combine extracts and wash with water and saturated sodium bicarbonate. Dry with sodium sulfate, filter, and concentrate in vacuo. Purify by silica gel chromatography using a 1-3% gradient of methanol in dichloromethane to yield 350 mg (57%) of the title compound: mass spectrum (ion spray) m/z=520 (M+H).

Example 49

[4-(2-Azepan-1-yl-ethoxy)-phenyl]-[2-(2-fluoro-phenyl)-6-methoxy-naphthalen-1-yl]methanone

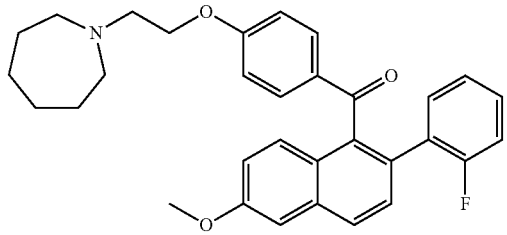

Dissolve trifluoromethanesulfonic acid 1-[4-(2-azepan-1-yl-ethoxy)-benzoyl]-6-methoxynaphthalen-2-yl ester (1.68 g, 3.05 mmol) in 30 mL of acetonitrile and add 2-fluorobenzene boronic acid (0.85 g, 6.10 mmol), trans[dichlorobis (triphenylphosphine)]palladium II (0.43 g, 0.61 mmol) and sonicate briefly. Next add cesium fluoride (4.17 g, 27.45 mmol) and heat to 75° C. for 1 hour. Add Celite and filter. Concentrate the solvent under vacuum, dissolve in methanol and purify on an SCX cartridge, eluting with 2 N ammonia/methanol. Purify further on a silica gel column eluting with a 0-10% methanol/methylene chloride gradient to isolate 1.10 g of the title compound (72%).

Example 50

[4-(2-Azepan-1-yl-ethoxy)-phenyl]-[2-(2-fluoro-phenyl)-6-hydroxy-naphthalen-1-yl]-methanone hydrochloride Dissolve [4-(2-azepan-1-yl-ethoxy)-phenyl]-[2-(2-fluoro-phenyl)-6-methoxy-naphthalen-1-yl]-methanone (550 mg, 1.11 mmol) in 20 mL methylene chloride and cool in an ice bath. Boron tribromide is added (1.5 mL) and allow to come to room temperature. Pour into a two phase solution of saturated sodium bicarbonate and 3/1 chloroform/isopropanol. Separate the organic layer, wash with water and dry over 3 Å sieves. Evaporate the solvent and purify on a silica gel column eluting with a 0-10% methanol/methylene chloride gradient to isolate 268 mg of the free base of the title compound (50%). Dissolve the free base in a 1:1 mixture of acetonitrile:water. Add an appropriate amount of 5 M hydrochloric acid and lyophilize the mixture to afford the title compound.

Example 51

5-[4-(2-Azepan-1-yl-ethoxy)-benzyl]-6-(2-fluoro-phenyl)-naphthalen-2-ol Hydrochloride

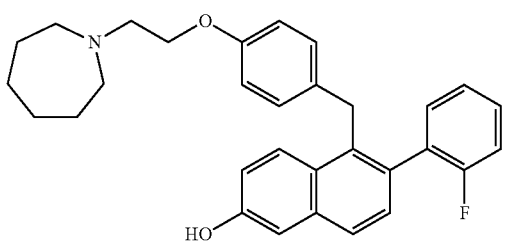

Dissolve [4-(2-azepan-1-yl-ethoxy)-phenyl]-[2-(2-fluoro-phenyl)-6-hydroxy-naphthalen-1-yl]-methanone (223 mg, 0.48 mmol) in 15 mL tetrahydrofuran. To this solution add 5 ml lithium triethylborohydride (1M solution in tetrahydrofuran). Dilute reaction with water and extract with ethyl acetate and concentrate. Dissolve the residue (the alcohol product) in 20 mL methylene chloride and add triethylsilane (0.06 mL, 0.40 mmol) and 15 mL trifluoroacetic acid. Concentrate this reaction and purify on a silica gel column eluting with a 0-10% methanol/methylene chloride gradient to give 70 mg (31%) of the free base of the title compound. Dissolve the free base in a 1:1 mixture of acetonitrile:water. Add an appropriate amount of 5 M hydrochloric acid and lyophilize the mixture to afford the title compound.

Example 52

[4-(2-Azepan-1-yl-ethoxy)-phenyl]-[6-methoxy-2-(2,3,6-trifluoro-phenyl)-naphthalen-1-yl]-methanone

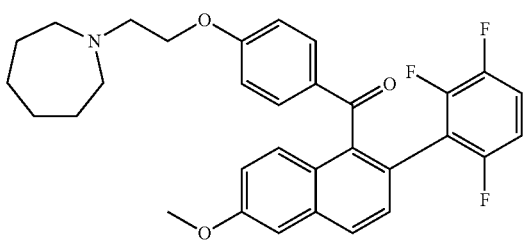

Couple trifluoromethanesulfonic acid 1-[4-(2-azepan-1-yl-ethoxy)-benzoyl]-6-methoxynaphthalen-2-yl ester (1.48 g, 2.67 mmol) with 2-bromo-1,3,4-trifluoro-benzene (1.13 g, 5.35 mmol) in a procedure similar to the preparation of [6-hydroxy-2-(2,3,5-trifluoro-phenyl)-naphthalen-1-yl]-[4-(2-piperidin-1-yl-ethoxy)-phenyl]-methanone to give 0.66 g (46%) of the title compound: mass spectrum (ion spray) m/z=534.4 (M+H).

Example 53

[4-(2-Azepan-1-yl-ethoxy)-phenyl]-[6-hydroxy-2-(2,3,6-trifluoro-phenyl)-naphthalen-1-yl]-methanone Demethylate[4-(2-azepan-1-yl-ethoxy)-phenyl]-[6-methoxy-2-(2,3,6-trifluoro-phenyl)-naphthalen-1-yl]-methasone (0.66 g, 1.24 mmol) with BBr₃ in a procedure similar to the preparation of [4-(2-azepan-1-yl-ethoxy)-phenyl]-[6-hydroxy-2-(2,4,6-trifluoro-phenyl)-naphthalen-1-yl]-methanone to give 0.53 g (82%) of the title compound. Analytical data obtained for the corresponding HCl salt: mass spectrum (ion spray) m/z 520.3 (M−Cl).

Example 54

[4-(2-Azepan-1-yl-ethoxy)-phenyl]-[2-(2,4-difluoro-phenyl)-6-methoxy-naphthalen-1-yl]-methanone

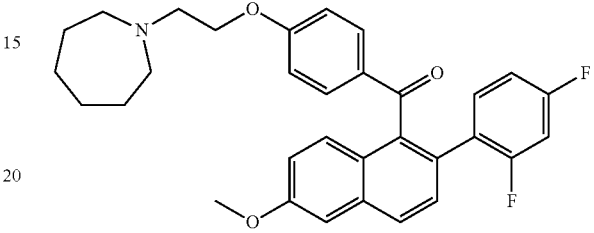

Couple trifluoromethanesulfonic acid 1-[4-(2-azepan-1-yl-ethoxy)-benzoyl]-6-methoxynaphthalen-2-yl ester (1.4 g, 2.5 mmol) and 2,4-difluorophenyl boronic acid (1.2 g, 7.6 mmol) by the procedure described for the preparation of 2-(2,4-difluoro-phenyl)-6-methoxy-naphthalen-1-yl]-[4-(2-piperidin-1-yl-ethoxy)-phenyl]-methanone to give 1.1 g (85%) of the title compound: mass spectrum (ion spray) m/z=516.3 (M+H).

Example 55

[4-(2-Azepan-1-yl-ethoxy)-phenyl]-[2-(2,4-difluoro-phenyl)-6-hydroxy-naphthalen-1-yl]methanone hydrochloride Demethylate[4-(2-azepan-1-yl-ethoxy)-phenyl]-[2-(2,4-difluoro-phenyl)-6-methoxy-naphthalen-1-yl]-methanone (1.1 g, 2.1 mmol) with BBr₃ (1.0 mL, 10.5 mmol) by the procedure described for the preparation of [2-(2,4-difluoro-phenyl)-6-hydroxy-naphthalen-1-yl]-[4-(2-piperidin-1-yl-ethoxy)-phenyl]-methanone. Purify on silica gel (0% to 5% methanol in methylene chloride) to yield 790 mg (75%) of the free base of the title compound: mass spectrum (ion spray) m/z=502.3 (M+H). Convert to the hydrochloride salt.

Example 56

[4-(2-Azepan-1-yl-ethoxy)-phenyl]-[2-(2,6-difluoro-phenyl)-6-methoxy-naphthalen-1-yl]-methanone

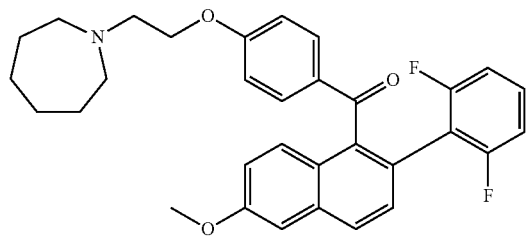

Charge a flask with trifluoromethanesulfonic acid 1-[4-(2-azepan-1-yl-ethoxy)-benzoyl]-6-methoxynaphthalen-2-yl ester (3.9 g, 7.06 mmol), 2,6-difluorophenyl boronic acid (2.23 g, 14.12 mmol), potassium phosphate (9.0 g, 42.20 mmol) and tetrakis(triphenylphosphine)palladium (0) (1.63 g, 1.40 mmol) followed by 125 mL dry DMF. Heat the mixture under nitrogen at 100° C. for 90 minutes. Cool, filter, evaporate the solvent and purify on an SCX cartridge, eluting with 2N ammonia/methanol. Purify further on a silica gel column eluting with 0-10% methanol/methylene chloride. The yield is 2.5 g (70%): 1H-NMR (CDCl$_3$, 400 MHz) δ 7.90 (d, J=8.4 Hz, 1H); 7.66-7.61 (m, 3H); 7.39 (d, J=8.4 Hz, 1H); 7.23-7.22 (m, 1H); 7.18-7.08 (m, 2H); 6.79-6.74 (m, 4H); 4.08-4.05 (t, 2H); 3.95 (s, 3H); 2.96-2.89 (t, 2H); 2.78-2.75 (m, 4H); 1.66-1.59 (m, 8H).

Example 57

[4-(2-Azepan-1-yl-ethoxy)-phenyl]-[2-(2,6-difluoro-phenyl)-6-hydroxy-naphthalen-1-yl]-methanone Convert [4-(2-azepan-1-yl-ethoxy)-phenyl]-[2-(2,6-difluoro-phenyl)-6-methoxy-naphthalen-1-yl]-methanone (2.5 g, 4.8 mmol) into the hydrochloride salt and charge a flask with the solid salt. Dissolve the material in 200 mL methylene chloride and chill in ice. Add to this mixture boron tribromide (5.0 mL, 53.0 mmol) while swirling. Stir the reaction at room temperature for one hour and pour into a two phase system of saturated sodium bicarbonate and an organic layer consisting of a 3/1 mixture of chloroform/isopropanol. Shake to extract the product, separate the organic layer, dry over 3 Å molecular sieves and evaporate the solvent under vacuum. Purify on a silica gel column eluting with a 0-10% methanol/methylene chloride gradient to give 1.3 g (54%) of the title compound: $^1$H-NMR (CDCl$_3$, 400 MHz) δ 7.79-7.74 (d, 1H); 7.58 (d, J=8.4 Hz, 2H); 7.50 (d, J=8.8 Hz, 1H); 7.33-7.30 (d, 1H); 7.17 (d, J=2.4 Hz, 1H); 7.16-7.08 (m, 1H); 6.99-6.95 (dd, 1H); 6.77-6.73 (m, 2H); 6.68 (d, J=9.2 Hz, 2H); 4.11 (t, J=6.0 Hz, 2H); 3.05-2.99 (t, 2H); 2.90-2.84 (m, 4H); 1.71-1.71 (m, 4H); 1.63-1.60 (m, 4H).

Example 58

[4-(2-Azepan-1-yl-ethoxy)-phenyl]-[2-(2,5-difluoro-phenyl)-6-methoxy-naphthalen-1-yl]-methanone

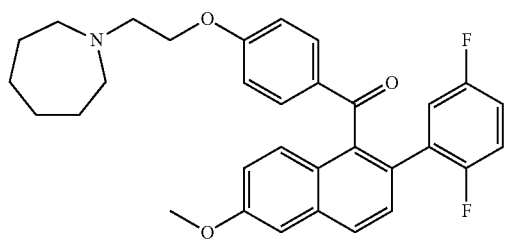

Dissolve trifluoromethanesulfonic acid 1-[4-(2-azepan-1-yl-ethoxy)-benzoyl]-6-methoxynaphthalen-2-yl ester (2.00 g, 3.63 mmol) in 5 mL of degassed acetonitrile and add 2,5-difluorophenyl boronic acid (1.15 g, 7.26 mmol), trans [dichlorobis(triphenylphosphine)]palladium II (0.51 g, 0.73 mmol) and sonicate briefly. Next add cesium fluoride (4.96 g, 32.76 mmol) and heat to 75° C. for one hour. Add Celite and filter. Concentrate the solvent under vacuum, dissolve in methanol and purify on an SCX cartridge, eluting with 2N ammonia/methanol to give 1.74 g (93%) of the title compound.

Example 59

[4-(2-Azepan-1-yl-ethoxy)-phenyl]-[2-(2,5-difluoro-phenyl)-6-hydroxy-naphthalen-1-yl]-methanone Dissolve [4-(2-azepan-1-yl-ethoxy)-phenyl]-[2-(2,5-difluoro-phenyl)-6-methoxy-naphthalen-1-yl]-methanone (1.74 g, 3.37 mmol) in 20 mL methylene chloride and chill in ice. Add to this solution 2.0 mL of boron tribromide (5.3 g, 21.2 mmol) and allow to come to room temperature. Pour into a two phase solution of saturated sodium bicarbonate and 3/1 chloroform/isopropanol. Separate the organic layer, wash with water and dry over 3A sieves. Evaporate the solvent and purify on a silica gel column eluting with a 0-10% methanol/methylene chloride gradient. Evaporate the solvent to give 780 mg (46%) of the title compound: $^1$H-NMR (CDCl$_3$, 300 MHz) δ 7.79 (d, J=8.7 Hz, 1H); 7.60-7.55 (m, 3H); 7.41 (dd, J=8.7, 1.8 Hz, 1H); 726-7.21 (m, 1H); 7.04-6.82 (m, 4H); 6.71-6.68 (m, 2H); 4.14-4.14 (m, 2H); 3.03-2.97 (m, 2H); 2.95-2.88 (m, 4H); 1.73-1.58 (m, 8H).

Example 60

[4-(2-Azepan-1-yl-ethoxy)-phenyl]-[6-methoxy-2-(2,3,5-trifluoro-phenyl)-naphthalen-1-yl]-methanone

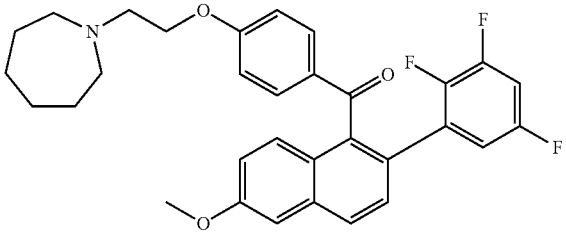

Dissolve trifluoromethanesulfonic acid 1-[4-(2-azepan-1-yl-ethoxy)-benzoyl]-6-methoxynaphthalen-2-yl ester (2.60 g, 6.53 mmol) in 200 ml. acetonitrile and add to this bis (pinacoloato)diboron (1.5 g, 7.96 mmol), bis(tricyclohexylphosphine)palladium (0) (0.72 g, 1.50 mmol) and cesium fluoride (7.33 g, 67.0 mmol). Heat the reaction to 100° C. until LC/MS indicates all starting material is consumed. Add to this mixture 1-bromo-2,3,5-trifluorobenzene (2.00 g, 13.06 mmol) and another 720 mg of palladium catalyst and heat at 80° C. for 24 hours. Filter the reaction, concentrate and purify on a silica gel column eluting with a 0-10% methanol/methylene chloride gradient to give 1.85 g (53%) of the title compound.

Example 61

[4-(2-Azepan-1-yl-ethoxy)-phenyl]-[6-hydroxy-2-(2,3,5-trifluoro-phenyl)-naphthalen-1-yl]-methanone Dissolve [4-(2-azepan-1-yl-ethoxy)-phenyl]-[6-methoxy-2-(2,3,5-trifluorophenyl)-naphthalen-1-yl]-methanone (2.85 g, 5.34 mmol) in 50 mL methylene chloride and cool to 0° C. Add boron tribromide (3.0 mL, 31.7 mmol) and allow to come to room temperature. Pour into a two phase system of saturated sodium bicarbonate and 3/1 chloroform/isopropanol.

Wash the organic layer with brine and dry over 3 Å molecular sieves. Concentrate to give 2.63 g (95%) of the title compound.

Preparation 10

Trifluoromethanesulfonic acid 6-methoxy-1-[4-(2-piperidin-1-yl-ethoxy)-benzyl]-naphthalen-2-yl ester

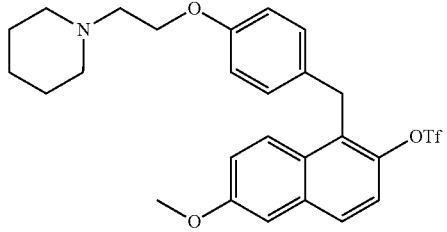

Dissolve (2,6-dimethoxy-naphthalen-1-yl)-[4-(2-piperidin-1-yl-ethoxy)-phenyl]-methanone (56.0 g, 123 mmol) in chloroform (500 mL). Cool to 0° C. Add boron trichloride (150 mL, 150 mmol, 1 M solution in dichloromethane) and stir 2 hours. Warm to room temperature and stir 1.5 hours. Add additional boron trichloride (50 mL, 50 mmol) after cooling to 0° C. Warm to room temperature and stir overnight. Carefully add ice and saturated aqueous sodium bicarbonate. Separate organic and wash aqueous three times with a 3:1 dichloromethane:isopropanol mixture. Concentrate in vacuo and dissolve in dichloromethane. Dry over sodium sulfate, decant, and concentrate in vacuo. Slurry in ether and filter, rinsing with hexanes to give 49.4 g of (2-hydroxy-6-methoxy-naphthalen-1-yl)-[4-(2-piperidin-1-yl-ethoxy)-phenyl]-methanone (99%).

Dissolve (2-hydroxy-6-methoxy-naphthalen-1-yl)-[4-(2-piperidin-1-yl-ethoxy)-phenyl]-methanone (12 g, 29.6 mmol) in tetrahydrofuran (200 Add lithium aluminum hydride (3.0 g, 78.0 mmol) and heat the reaction to reflux. Allow to cool to room temperature and add ice. Adjust the pH of the mixture to 7 with 5 M hydrochloric acid. Dilute with water (500 mL). Wash the mixture four times with dichloromethane (500 mL each wash). Combine the organics, dry over sodium sulfate, decant, and concentrate in vacuo to give 1-{hydroxy-[4-(2-piperidin-1-yl-ethoxy)-phenyl]-methyl}-6-methoxy-naphthalen-2-ol.

Redissolve in chloroform and add trifluoroacetic acid (5.0 mL, 64.9 mmol) and triethylsilane (10.0 mL, 62.6 mmol). Heat the reaction to reflux for 1 hour. Cool to room temperature and dilute with saturated aqueous sodium bicarbonate (300 mL). Extract the organic and wash the aqueous twice with dichloromethane (300 mL each wash). Combine the organics, dry over sodium sulfate, decant, and concentrate in vacuo. Isolate a residue containing 6-methoxy-1-[4-(2-piperidin-1-yl-ethoxy)-benzyl]-naphthalen-2-ol. Purify the residue on an SCX column, eluting the impurities with methanol, then eluting the product with 2N ammonia/methanol.

Dissolve 6-methoxy-1-[4-(2-piperidin-1-yl-ethoxy)-benzyl]-naphthalen-2-ol in dichloroethane (300 mL) and add N-phenylbis(trifluoromethanesulfonimide (15.0 g, 42.0 mmol). Add triethylamine (20 mL, 143.5 mmol) and heat to reflux for 6 hours. Concentrate in vacuo and purify the residue by column chromatography using a silica gel column eluting with a linear gradient beginning with dichloromethane and ending with 20:1 dichloromethane:methanol to give 13.6 g of the title compound (88%).

Example 62

1-(2-{4-[2-(2,5-Difluoro-phenyl)-6-methoxy-naphthalen-1-ylmethyl]-phenoxy}-ethyl)-piperidine

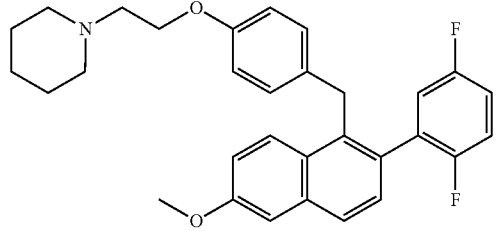

Charge a flask with trifluoromethanesulfonic acid 6-methoxy-1-[4-(2-piperidin-yl-ethoxy)-benzyl]-naphthalen-2-yl ester (1.0 g, 1.91 mmol) and add 20 mL degassed acetonitrile. To this solution add 2,5-difluorophenyl boronic acid (0.6 g, 3.82 mmol), transdichlorobis(triphenylphosphine) palladium II, (270 mg, 0.38 mmol) and cesium fluoride (2.61 g, 17.2 mmol). Sonicate the mixture briefly and heat to 75° C. After 3 hours add an additional small amount of the acid, the catalyst and the cesium fluoride and heat overnight. In the morning filter the mixture and run through and SCX column eluting with 2N ammonia in methanol. Purify further on a silica gel column eluting with a 0-10% methanol/methylene chloride gradient. Concentrate to give 430 mg (46%) of the title compound: $^1$H-NMR (CDCl$_3$, 300 MHz) δ 7.85 (d, J=9.3 Hz, 1H); 7.73 (d, J=8.7 Hz, 1H); 7.33 (d, J=8.4 Hz, 1H); 7.18 (d, J=2.7 Hz, 1H); 7.11-6.89 (m, 4H); 6.86-6.82 (m, 2H); 6.73-6.69 (m, 2H); 4.34-4.19 (d, H); 4.04-3.99 (t, 2H); 3.93 (s, 3H); 2.72 (t, J=6.3 Hz, 2H); 2.47 (t, J=5.1 Hz, 4H); 1.58 (qui, J=5.4 Hz, 4H); 1.46-1.41 (m, 2H).

Example 63

6-(2,5-Difluoro-phenyl)-5-[4-(2-piperidin-1-yl-ethoxy)-benzyl]-naphthalen-2-ol hydrochloride Dissolve 1-(2-{4-[2-(2,5-difluoro-phenyl)-6-methoxy-naphthalen-1-ylmethyl]-phenoxy}-ethyl)-piperidine in 20 mL acetonitrile and chill in an ice bath. Add 1.5 mL of boron tribromide with swirling and allow to warm to room temperature. Pour this mixture into a two-phase mixture of saturated sodium bicarbonate solution and a 3/1 mixture of chloroform/isopropanol. Wash the organic layer with water and dry over 3 Å molecular sieves. Concentrate the organic layer and purify on a silica gel column, eluting with a 0-10% methanol/methylene chloride gradient. Evaporate the solvent and convert the compound to the salt with HCl to give 369 mg (82%) of the title compound: 1H-NMR (CDCl$_3$, 300 MHz) δ 7.77 (d, J=8.7 Hz, 1H); 7.61 (d, J=8.1 Hz, 1H); 7.28-7.25 (m, 1H); 7.11-6.94 (m, 4H); 6.89-6.83 (m, 1H); 6.74 (d, J=8.7 Hz, 2H); 6.57-6.54 (m, 2H); 4.31-4.10 (d, 2H); 4.04 (t, J=6.0 Hz, 2H); 2.80-2.80 (m, 2H); 2.59-2.59 (m, 4H); 1.68-1.65 (m, 4H); 1.48-1.46 (m, 2H).

Example 64

1-(2-{4-[2-(2,4-Difluoro-phenyl)-6-methoxy-naphthalen-1-ylmethyl]-phenoxy}-ethyl)-piperidine

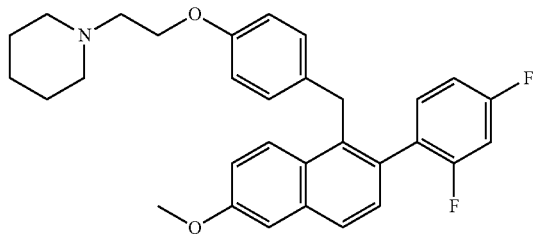

Dissolve trifluoromethanesulfonic acid 6-methoxy-1-[4-(2-piperidin-1-yl-ethoxy)-benzyl]-naphthalen-2-yl ester (1.00 g, 1.91 mmol) in 20 mL of degassed acetonitrile and add 2,4-difluorophenyl boronic acid (0.60 g, 3.82 mmol), trans[dichlorobis(triphenylphosphine)]palladium II (0.27 g, 0.38 mmol) and sonicate briefly. Next add cesium fluoride (2.61 g, 17.19 mmol) and heat to 75° C. for one hour. Add Celite and filter. Concentrate the solvent under vacuum, dissolve in methanol and purify on an SCX cartridge, eluting with 2N ammonia/methanol to isolate the title compound.

Example 65

6-(2,4-Difluoro-phenyl)-5-[4-(2-piperidin-1-yl-ethoxy)-benzyl]-naphthalen-2-ol hydrochloride Dissolve 1-(2-{4-[2-(2,4-difluoro-phenyl)-6-methoxy-naphthalen-1-ylmethyl]-phenoxy}-ethyl)-piperidine (0.72 g, 1.48 mmol) in 30 mL methylene chloride and chill in ice. Add to this solution 2.0 mL of boron tribromide (21.2 mmol) and allow to come to room temperature. Pour into a two phase solution of saturated sodium bicarbonate and 3/1 chloroform/isopropanol. Separate the organic layer, wash with water and dry over 3 Å sieves. Evaporate the solvent and purify on a silica gel column eluting with a 0-10% methanol/methylene chloride gradient. Evaporate the solvent to yield 300 mg (43%) of the free base of the title compound. Dissolve the free base in a 1:1 mixture of acetonitrile:water. Add an appropriate amount of 5 M hydrochloric acid and lyophilize the mixture to afford the title compound.

Example 66

1-(2-{4-[2-(4-Fluoro-phenyl)-6-methoxy-naphthalen-1-ylmethyl]-phenoxy}-ethyl)-piperidine

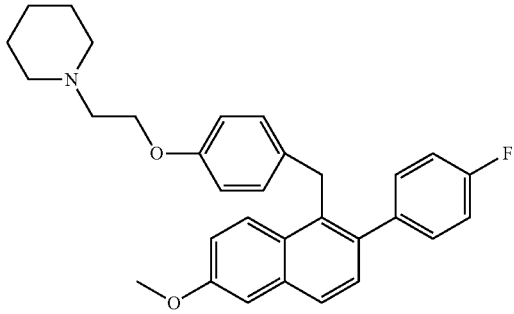

Dissolve trifluoromethanesulfonic acid 6-methoxy-1-[4-(2-piperidin-1-yl-ethoxy)-benzyl]-naphthalen-2-yl ester (1.0 g, 1.91 mmol), 4-fluorophenyl boronic acid (3.8 g., 3.8 mmol), trans[dichlorobis(triphenylphosphine)]palladium II (266 mg, 0.38 mmol) and cesium fluoride (2.6 g, 17.1 mmol) in 125 mL degassed acetonitrile and heat at 85° C. for 8 hours. Cool and filter and purify on an SCX column and elute with 2 N ammonia/methanol. Evaporate to an oil and purify on a silica gel column eluting with a gradient of 0-10% methanol/methylene chloride: mass spectrum (ion spray) m/z=470 (M+H).

Example 67

6-(4-Fluoro-phenyl)-5-[4-(2-piperidin-1-yl-ethoxy)-benzyl]-naphthalen-2-ol hydrochloride Dissolve 1-(2-{4-[2-(4-fluoro-phenyl)-6-methoxy-naphthalen-1-ylmethyl]-phenoxy}-ethyl)-piperidine (500 mg, 1.06 mmol) in 250 mL methylene chloride and chill in ice. To this add 1.0 ad, boron tribromide with swirling and allow the mixture to come to room temperature. After one hour add another 1.0 mL of the boron tribromide, then after 30 minutes add another 0.5 mL of the bromide and stir for another 30 minutes. Pour the reaction into a two-phase system of saturated sodium bicarbonate and an organic layer consisting of a 3/1 mixture of chloroform/isopropanol. Shake in a separatory funnel, separate the organic layer and dry over 3 Å molecular sieves. Evaporate the solvent and purify on a silica column eluting with a gradient of 0-10% methanol/methylene chloride to give 300 mg of the free base of the title compound (62%). Convert the free base to the salt by dissolving in acetonitrile and adding hydrochloric acid and lyophilizing the resulting solution.

Example 68

1-(2-{4-[2-(2-Fluoro-phenyl)-6-methoxy-naphthalen-1-ylmethyl]-phenoxy}-ethyl)-piperidine

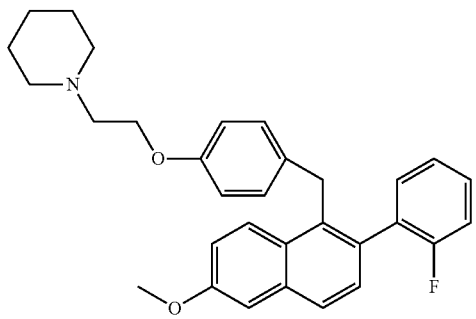

Dissolve trifluoromethanesulfonic acid 6-methoxy-1-[4-(2-piperidin-1-yl-ethoxy)-benzyl]-naphthalen-2-yl ester (1.0 g, 1.9 mmol), 2-fluorophenyl boronic acid (532 mg, 3.8 mmol), trans[dichlorobis(triphenylphosphine)]palladium II (266 mg, 0.38 mmol) and cesium fluoride (2.6 g, 17.1 mmol) in 150 mL degassed acetonitrile and heat at 85° C. for 2 hours. Cool the reaction, filter and purify on an SCX column, eluting with 2N ammonia/methanol. Concentrate and purify on a silica column eluting with 1 0-10% gradient of methanol/methylene chloride to give 560 mg (63%) of the title compound: mass spectrum (ion spray) m/z=470 (M+H).

Example 69

6-(2-Fluoro-phenyl)-5-[4-(2-piperidin-1-yl-ethoxy)-benzyl]-naphthalen-2-ol hydrochloride Dissolve 1-(2-{4-[2-(2-fluoro-phenyl)-6-methoxy-naphthalen-1-ylmethyl]-phenoxy}-ethyl)-piperidine (560 mg, 1.2 wool) in 250 mL acetonitrile and chill in ice. Add 2.0 mL of boron tribromide with swirling, stir one hour and allow to come to room temp. Pour the reaction into a two-phase system consisting of saturated sodium bicarbonate and an organic layer of a 3/1 mixture of chloroform/methanol. Shake in a reparatory funnel, separate the organic layer and dry over molecular sieves. Evaporate the solvent and purify on an SCX column, eluting with 2N ammonia/methanol. Evaporate the solvent to an oil and purify on a silica column eluting with a 0-10% methanol/methylene chloride gradient to give 220 mg of the free base of the title compound (48%). Convert to the HCl salt by dissolving in acetonitrile and adding hydrochloric acid and lyophilizing.

Example 70

1-(2-{4-[2-(3-Fluorophenyl)-6-methoxy-naphthalen-1-ylmethyl]-phenoxy}-ethyl)-piperidine

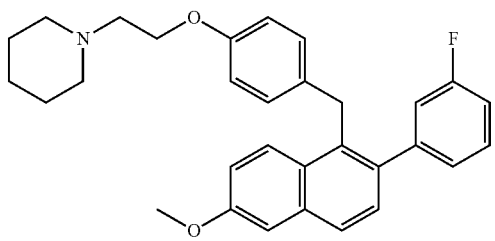

Charge a flask with trifluoromethanesulfonic acid 6-methoxy-1-[4-(2-piperidin-1-yl-ethoxy)-benzyl]-naphthalen-2-yl ester (2.0 g, 3.82 mmol), 3-fluorophenyl boronic acid (1.07 g, 7.64 mmol), trans-dichlorobis(triphenylphosphine)palladium II (536 mg, 0.76 mmol) and cesium fluoride (5.2 g, 34.4 mmol) along with 100 mL degassed acetonitrile and heat at 85° C. for 4 hours or until all the starting triflate is consumed. Cool the reaction, filter and purify on an SCX column eluting with 2N ammonia/methanol. The crude yield is 1.5 g (83%). Further purify the crude material on a silica column, eluting with 3% methanol/methylene chloride to give 1.1 g of the title compound (63%): 1H-NMR (CDCl$_3$, 400 MHz) δ 7.81 (d, J=9.6 Hz, 1H); 7.73 (d, J=8.4 Hz, 1H); 7.39 (d, J=8.4 Hz, 1H); 7.28-7.25 (m, 1H); 7.19 (d, J=2.4 Hz, 1H); 7.11-7.06 (m, 2H); 7.04-7.01 (m, 2H); 6.88 (d, J=9.2 Hz, 2H); 6.75 (dd, J=6.4, 2.4 Hz, 2H); 4.34 (s, 2H); 4.07 (t, J=6.0 Hz, 2H); 3.93 (s, 3H); 2.81 (t, J=6.0 Hz, 2H); 2.57-2.57 (m, 4H); 1.67-1.61 (m, 4H); 1.48-1.46 (m, 2H).

Example 71

6-(3-Fluoro-phenyl)-5-[4-(2-piperidin-1-yl-ethoxy)-benzyl]-naphthalen-2-ol hydrochloride Charge a flask with 1-(2-{4-[2-(3-fluorophenyl)-6-methoxy-naphthalen-1-ylmethyl]-phenoxy}-ethyl)-piperidine (1.1 g, 2.3 mmol) dissolved in 250 mL methylene chloride and chill in ice. Add 6.0 mL of neat boron tribromide in portions with stirring and stir the reaction in ice for one hour then at room temperature for 2 hours. Pour the reaction into a two-phase mixture consisting of saturated sodium bicarbonate and an organic phase of 3/1 chloroform/isopropanol. Extract the compound into the organic phase using a separatory funnel, separate the phases and dry the organic layer over 3 Å molecular sieves. Evaporate and purify on a silica column eluting with 3% methanol/methylene chloride. Convert to the hydrochloride salt and lyophilize to yield 650 mg (57%) of the title compound: 1H-NMR (data reported for the free base) (CDCl$_3$, 400 MHz) δ 7.73 (d, J=9.6 Hz, 1H); 7.61 (d, J=8.0 Hz, 1H); 7.32-7.30 (m, 1H); 7.28-7.24 (m, H); 7.15 (d, J=2.0 Hz, 1H); 7.04-6.94 (m, 4H); 6.79 (d, J=8.4 Hz, 2H); 6.62-6.59 (m, 2H); 4.28 (s, 2H); 4.13 (t, J=5.6 Hz, 2H); 2.92-2.92 (m, 2H); 2.72-2.64 (m, 4H); 1.74 (d, J=4.8 Hz, 4H); 1.51-1.51 (m, 2H).

Example 72

1-(2-{4-[6-Methoxy-2-(2,3,4,5-tetrafluoro-phenyl)-naphthalen-1-ylmethyl]-phenoxy}-ethyl)-piperidine

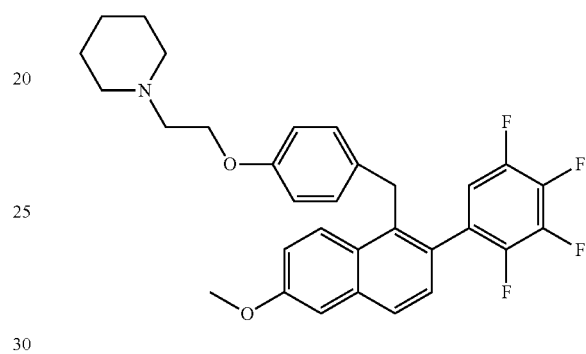

Dissolve trifluoromethanesulfonic acid 6-methoxy-1-[4-(2-piperidin-1-yl-ethoxy)-benzyl]-naphthalen-2-yl ester (259 mg, 0.49 mmol), bis(pinacolato)diboron (151 mg, 0.59 mmol), bis(tricyclohexylphosphine)palladium (0) (75 mg, 0.11 mmol) and cesium fluoride (764 mg, 5.03 mmol) in 20 mL degassed acetonitrile and heat at 100° C. under nitrogen in a sealed vial. The reaction is complete in 10 minutes. Cool and add 1-bromo-2,3,4,5-tetrafluorobenzene (224 mg, 0.99 mmol) along with 10 mL acetonitrile, seal the vial, purge with nitrogen and heat at 80° C. for 2 hours. Cool, filter and purify on an SCX column eluting with 2N ammonia/methanol. Evaporate the solvent and purify the resulting oil on a silica column eluting with 3% methanol/methylene chloride to give 188 mg of the title compound (73%).

Example 73

5-[4-(2-Piperidin-1-yl-ethoxy)-benzyl]-6-(2,3,4,5-tetrafluoro-phenyl)-naphthalen-2-ol hydrochloride Dissolve 1-(2-{4-[6-methoxy-2-(2,3,4,5-tetrafluoro-phenyl)-naphthalen-1-ylmethyl]-phenoxy}-ethyl)-piperidine (180 mg, 0.34 mmol) in 50 mL methylene chloride and chill in ice. Add 2.0 mL boron tribromide and stir in ice for 1 hour. Pour this mixture into a 2-phase mixture consisting of saturated sodium bicarbonate and an organic layer of 3/1 chloroform/isopropanol. Shake in a separatory funnel, separate the organic layer, wash it with brine and dry over molecular sieves. Evaporate the solvent and purify on a silica column eluting first with pure methylene chloride, then with 3% methanol/methylene chloride. Repeat the purification to give 45 mg of the free base of the title compound (26%). The free base is converted to the hydrochloride salt by dissolving in acetonitrile, adding HCl and lyophilizing: mass spectrum (ion spray) m/z=510 (M−Cl).

Preparation 11

(4-Bromo-phenyl)-(2-piperidin-1-yl-ethyl)-carbamic acid tert-butyl ester

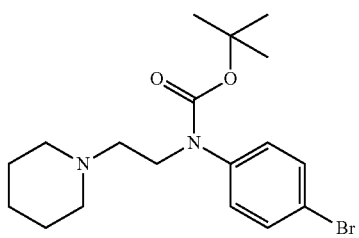

Dissolve (4-bromo-phenyl)-carbamic acid tert-butyl ester (3.0 g, 11.0 mmol) in N,N-dimethylformamide (30 mL). Add sodium hydride (1.1 g, 27.6 mmol) and stir at room temperature. Add 1-(2-chloroethylpiperidine)monohydrochloride (3.0 g, 16.5 mmol). Stir overnight at room temperature and then overnight at 60° C. Cool to room temperature and dilute with ethyl acetate and water. Separate the organic layer and wash the aqueous with ethyl acetate. Combine the organics and wash with saturated aqueous sodium chloride. Dry over magnesium sulfate, filter, and concentrate in vacuo. Purify the residue by column chromatography using a silica gel column eluting with a linear gradient beginning with dichloromethane and ending with 9:1 dichloromethane:methanol to give 1.2 g of the title compound.

Example 74

1-(2-{4-[2-(2,6-Difluoro-phenyl)-6-methoxy-naphthalen-1-ylmethyl]-phenoxy}-ethyl)-piperidine

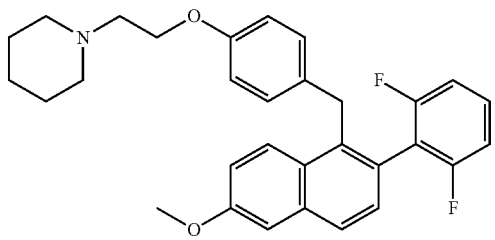

Dissolve trifluoromethanesulfonic acid 6-methoxy-1-[4-(2-piperidin-1-yl-ethoxy)-benzyl]-naphthalen-2-yl ester (1.50 g, 2.86 mmol) in 50 mL of acetonitrile and add 2,6-difluorophenyl boronic acid (0.90 g, 5.73 mmol), tetrakis(triphenylphosphine)palladium(0) (0.66 g, 0.57 mmol). Next add potassium phosphate (3.64 g, 17.16 mmol) and heat to 80° C. for one hour. Add Celite and filter. Concentrate the solvent under vacuum to a dark oil, dissolve in methanol and purify on an SCX cartridge, eluting with 2N ammonia/methanol. Purify further on a silica gel column eluting with a 0-10% methanol/methylene chloride gradient. Evaporate the solvent to yield 800 mg (58%) of the title compound.

Example 75

6-(2,6-Difluoro-phenyl)-5-[4-(2-piperidin-1-yl-ethoxy)-benzyl]-naphthalen-2-ol hydrochloride Dissolve 1-(2-{4-[2-(2,6-difluoro-phenyl)-6-methoxy-naphthalen-1-ylmethyl]-phenoxy}-ethyl)-piperidine (800 mg, 1.64 mmol) in 20 mL methylene chloride and cool in an ice bath. To this solution add 2.0 mL boron tribromide (21.2 mmol) and allow to come to room temperature. Pour into a two phase solution of saturated sodium bicarbonate and 3/1 chloroform/isopropanol. Separate the organic layer, wash with water and dry over 3 Å sieves. Evaporate the solvent and purify on a silica gel column eluting with a 0-10% methanol/methylene chloride gradient to give 670 mg (86%) of the free base of the title compound. Dissolve the free base in a 1:1 mixture of acetonitrile:water. Add an appropriate amount of 5M hydrochloric acid and lyophilize the mixture to afford the title compound.

Example 76

1-(2-{4-[2-(2,3-Difluoro-phenyl)-6-methoxy-naphthalen-1-ylmethyl]-phenoxy}-ethyl)-piperidine

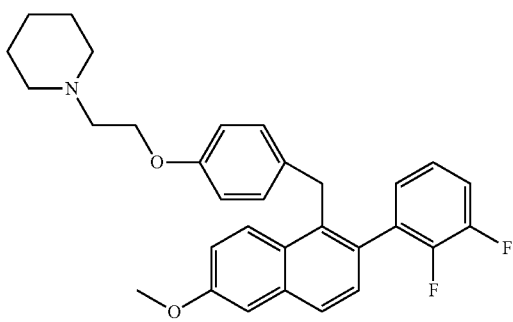

Using the method described in the preparation of 1-(2-{4-[6-methoxy-2-(2,3,4,5-tetrafluoro-phenyl)-naphthalen-1-ylmethyl]-phenoxy}-ethyl)-piperidine, prepare the title compound in 49% yield: mass spectrum (ion spray) m/z=488 (M+H).

Example 77

6-(2,3-Difluoro-phenyl)-5-[4-(2-piperidin-1-yl-ethoxy)-benzyl]-naphthalen-2-ol hydrochloride Using the method described in the preparation of 5-[4-(2-piperidin-1-yl-ethoxy)-benzyl]-6-(2,3,4,5-tetrafluoro-phenyl)-naphthalen-2-ol hydrochloride, obtain the title compound in 39% yield: mass spectrum (ion spray) m/z=474 (M+H).

Example 78

[6-hydroxy-2-(2,3,5-trifluoro-phenyl)-naphthalen-1-yl]-[4-(2-piperidin-1-yl-ethoxy)-phenyl]-methanone

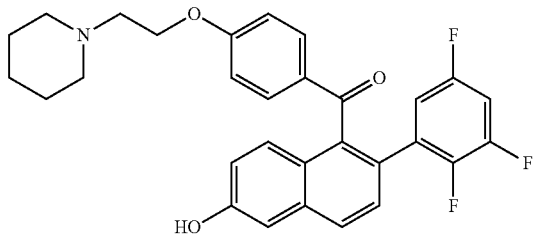

Dissolve trifluoromethanesulfonic acid 6-methanesulfonyloxy-1-[4-(2-piperidin-1-yl-ethoxy)-benzoyl]-naphthalen-2-yl ester (10.0 g, 16.6 mmol) in degassed acetonitrile (100 mL). Add cesium fluoride (13.0 g, 83 mmol) and bis (acetato)bis(triphenylphosphine)palladium (1.2 g, 1.7 mmol) followed by bis(neopentyl glycolato)diboron (4.5, 19.9 mmol) and plunge into a 75° C. oil bath under nitrogen. After 15 minutes, add 1-bromo-2,3,5-trifluorobenzene (7.0 g, 33.2 mmol) to the reaction and bis(acetato)bis(triphenylphosphine)palladium (500 mg) and stir at 75° C. for 2.5 hours. Cool the reaction to room temperature and filter through celite. Concentrate the filtrate in vacuo and redissolve the residue in methanol (100 mL). Add KOH (4 g) and stir at room temperature overnight. Pour the reaction into saturated aqueous ammonium chloride and extract with methylene chloride. Dry the organic layer with sodium sulfate, filter and concentrate in vacuo. Purify on 5 SCX columns (loading with methanol and eluting with 2M NH$_3$ in methanol) to obtain 8.4 g (100%) of the title compound. Mass spectrum (ion spray): m/z=506.4 (M+H).

Example 79

5-{Hydroxy-[4-(2-piperidin-1-yl-ethoxy)-phenyl]-methyl}-6-(2,3,5-trifluoro-phenyl)-naphthalen-2-ol Charge a nitrogen-purged flask with (R)-(+)-α,α-diphenyl-2-pyrrolidinemethanol (630 mg, 2.49 mmol), dissolve in 1M BH$_3$-tetrahydrofuran (THF) (66 mL, 66 mmol) and heat to 45° C. under nitrogen. Dissolve [6-hydroxy-2-(2,3,5-trifluoro-phenyl)-naphthalen-1-yl]-[4-(2-piperidin-1-yl-ethoxy)-phenyl]-methanone (8.3 g, 16.6 mmol) in THF (75 mL) and add dropwise via syringe pump to the borane solution over 2.5 hours. Add ethanolamine (20 mL, 332 mmol) slowly and heat at 45° C. for 2 hours. Pour the reaction into saturated aqueous ammonium chloride and extract twice with methylene chloride. Wash the combined organic layers with water, dry over sodium sulfate, filter and concentrate. Dissolve the residue in methylene chloride (20 mL) and allow to slowly precipitate. Collect the precipitate to yield 4.3 g (51%) of the title compound in >99% ee. Purify the mother liquor over silica gel (eluting with 1 to 6% methanol in methylene chloride) to yield 2.0 g (75% total yield) of the title compound in 91% ee. Mass spectrum (ion spray): m/z=508.3 (M+H).

Example 80

7,9-Difluoro-5-[4-(2-piperidin-1-yl-ethoxy)-phenyl]-5H-6-oxa-chrysen-2-ol

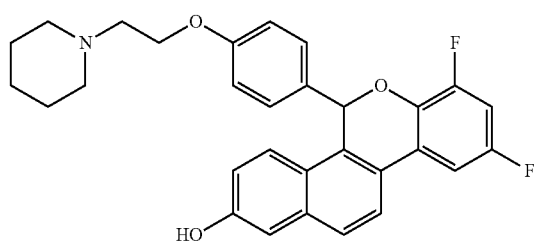

Dissolve 5-{hydroxy-[4-(2-piperidin-1-yl-ethoxy)-phenyl]-methyl}-6-(2,3,5-trifluoro-phenyl)-naphthalen-2-ol (4.3 g, 3.0 mmol) in dry THF (85 mL). Add KOtBu (2.4 g, 21.3 mmol) and stir at room temperature for 3 hours. Pour into saturated aqueous ammonium chloride and extract twice with methylene chloride. Dry the organic layer with sodium sulfate, filter and concentrate in vacuo to yield 3.7 g (90%) of the title compound: mass spectrum (ion spray) m/z=488.2 (M+H). The mixture is purified by chiral chromatography (conditions P). The two isomers eluted with retention times of 6.9 and 8.6 minutes.

Example 81

7,9-Difluoro-5-[4-(2-piperidin-1-yl-ethoxy)-phenyl]-5H-6-oxa-chrysen-2-ol hydrochloride salt Dissolve 7,9-difluoro-5-[4-(2-piperidin-1-yl-ethoxy)-phenyl]-5H-6-oxa-chrysen-2-ol (1.6 g, 3.3 mmol) in methylene chloride (20 mL). Add 2M HCl in ether (3.3 mL, 6.6 mmol) and concentrate in vacuo. Dissolve the residue in methylene chloride (5 mL) and add dropwise to vigorously stirred ether (30 mL). Filter the precipitate and dry in a 50° C. vacuum oven overnight to obtain 1.5 g (87%) of the title compound. Mass spectrum (ion spray): m/z=488.3 (M+H−HCl).

Example 82

[6-Methoxy-2-(2,4,6-trifluoro-phenyl)-naphthalen-1-yl]-[4-(2-piperidin-1-yl-ethoxy)-phenyl]-methanone

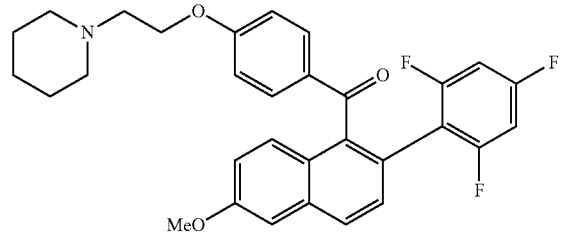

Dissolve trifluoromethanesulfonic acid 6-methoxy-1-[4-(2-piperidin-1-yl-ethoxy)-benzoyl]-naphthalen-2-yl ester (752 mg, 1.4 mmol), 2,4,6-trifluorophenylboronic acid (493 mg, 2.8 mmol), potassium phosphate (1.8 g, 8.4 mmol)) and tetrakis(triphenylphosphine)palladium (324 mg, 0.3 mmol) in dry dimethylformamide (DMF, 25 mL) and heat at 100° C. for 20 minutes. Purify reaction on an SCX column to yield 674 mg (93%) of the title compound. Mass spectrum (ion spray): m/z=520.2 (M+H).

Alternatively, combine trifluoromethanesulfonic acid 6-methoxy-1-[4-(2-piperidin-1-yl-ethoxy)-benzoyl]-naphthalen-2-yl ester (1.93 g, 3.60 mmol), cesium fluoride (5.0 g, 33 mmol), bis(neopentyl glycolato)diboron (1.0 g, 4.4 mmol), bis(tricyclohexylphosphine)palladium (0.50 g, 0.75 mmol) and acetonitrile (50 mL). Heat the mixture to 90° C. for 20 minutes to obtain a dark-colored solution. Add 2-bromo-1,3,5-trifluoro-benzene (5 g, 23.7 mmol) and heat at 90° C. for 2 hours. Add bis(tricyclohexylphosphine)palladium (0.50 g, 0.75 mmol) and 2-bromo-1,3,5-trifluoro-benzene (5.0 g, 23 mmol) and heat at 90° C. for 4 hours. Cool to room temperature and filter through a pad of celite and evaporate the solvent. Purify the residue over silica gel, eluting the material with methanol in dichloromethane (0 to 5%), to give 1.30 g (67%) of title compound: mass spectrum (ion spray) m/z=520.2 (M+H).

Example 83

[6-Hydroxy-2-(2,4,6-trifluoro-phenyl)-naphthalen-1-yl]-[4-(2-piperidin-1-yl-ethoxy)-phenyl]-methanone Dissolve [6-methoxy-2-(2,4,6-trifluoro-phenyl)-naphthalen-1-yl]-[4-(2-piperidin-1-3/1-ethoxy)-phenyl]-methanone (670 mg, 1.3 mmol) in dichloromethane (10 mL). Cool to 0° C., add 2M HCl (1.3 mL, 2.6 mmol) and stir at room temperature for 15 minutes. Concentrate in vacuo. Redissolve the salt in dichloromethane (10 mL) and cool to 0° C. Add borontribromide (1.1 g, 3.9 mmol) dropwise and bring to room temperature. Stir reaction for 1.5 hours and pour reaction mixture onto ice, saturated sodium bicarbonate (10 mL) and methanol (10 mL). Extract with dichloromethane, combine extracts and wash with water and saturated sodium bicarbonate. Dry with sodium sulfate, filter, and concentrate in vacuo. Purify by silica gel chromatography using a 1-3% gradient of methanol in dichloromethane to yield 454 mg (70%) of the title compound. Mass spectrum (ion spray): m/z=506.3 (M+H).

Alternatively, dissolve [6-methoxy-2-(2,4,6-trifluoro-phenyl)-naphthalen-1-yl]-[4-(2-piperidin-1-yl-ethoxy)-phenyl]-methanone (1.90 g, 3.67 mmol) in dichloromethane (10 ml). Add 2 M HCl in diethyl ether (4.0 mL, 80 mmol). Concentrate the slurry and dry in vacuo. Dilute the residue in dichloromethane (30 ml) and blanket with nitrogen. Cool the solution to 0° C. with an external ice bath. Add boron tribromide (1 mL, 11 mmol). After 60 minutes, pour the reaction mixture into a mixture of ice (20 g), methanol (10 mL) and saturated sodium bicarbonate solution (20 mL). Extract with dichloromethane (100 mL). Separate the layers, wash the organic layer with brine (20 mL), dry with magnesium sulfate, filter, and concentrate in vacuo. Purify the residue over silica gel, eluting the material with a step gradient of methanol/dichloromethane (0 to 10%), to give 1.6 g (87%) of the title compound: mass spectrum (ion spray) m/z=506.2 (M+H).

Example 84

5-{Hydroxy-[4-(2-piperidin-1-yl-ethoxy)-phenyl]-methyl}-6-(2,4,6-trifluoro-phenyl)-naphthalen-2-ol Hydrochloride Dissolve [6-hydroxy-2-(2,4,6-trifluoro-phenyl)-naphthalen 1-yl]-[4-(2-piperidin-1-yl-ethoxy)-phenyl]-methanone (728 mg, 1.4 mmol) in THF (85 mL) and cool to 0° C. Add 1M lithium aluminum hydride in THF (5.8 mL, 5.8 mmol) and bring to room temperature. Heat the reaction to reflux for 30 minutes. Cool reaction and pour onto ice/chloroform to form a suspension. Add 6N HCl dropwise to obtain a pH of 1. Extract with 20% isopropyl alcohol in chloroform. Wash organic layer with brine, dry, filter, and concentrate in vacuo to yield 730 mg (100%) of the title compound. HPLC R$_t$ (0.01% heptafluorobutyric acid:1.0% isopropylalcohol:water is mobile phase A and 0.01% heptafluorobutyric acid:1.0% isopropylalcohol:acetonitrile is mobile phase B; gradient: 5 to 95% B, Purity@254 nm)=2.41 (100%); mass spectrum (ion spray): m/z=508.3 (M+H).

Alternatively, add (R)-(+)-α,α-diphenylprolinol (83 mg, 0.33 mmol) to a mixture of 1M borane in THF (8 mL, 8 mmol) and THF (8 mL) at 45° C. Dissolve [6-hydroxy-2-(2,4,6-trifluoro-phenyl)-naphthalen-1-yl]-[4-(2-piperidin-1-yl-ethoxy)-phenyl]-methanone (0.83 g, 1.6 mmol) in THF (5 mL) and add to the reaction mixture over 3 hours via a syringe pump at 45° C. Cool to 0° C. and add 2-amino-ethanol (1.0 mL, 16 mmol) dropwise. Heat at 45° C. for 30 minutes. Wash the mixture with water (10 mL) and extract aqueous phase with ethyl acetate (20 mL). Combine the organic layers and wash with brine. Dry with magnesium sulfate and concentrate in vacuo. Purify the residue over silica gel, eluting the material with a step gradient of methanol/dichloromethane (0 to 10%), to give 804 mg (97%) of enantiomerically enriched title compound: mass spectrum (ion spray) m/z=508.2 (M+H).

Example 85

8,10-Difluoro-5-[4-(2-piperidin-1-yl-ethoxy)-phenyl]-5H-6-oxa-chrysen-2-ol

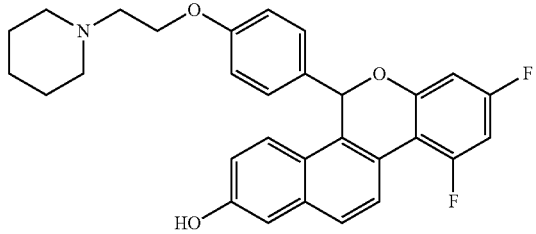

Dissolve 5-{hydroxy-[4-(2-piperidin-1-yl-ethoxy)-phenyl]-methyl}-6-(2,4,6-trifluoro-phenyl)-naphthalen-2-ol hydrochloride (730 mg, 1.4 mmol) and potassium tert-butoxide (5.36 mg, 4.8 mmol) in dry DMF (25 mL) and heat at 50° C. for 10 minutes. Cool reaction and pour onto ice/ethyl acetate. Separate organic layer and wash with 10% aqueous lithium chloride. Dry, filter, and concentrate in vacuo. Purify by silica gel chromatography using a 1-6% gradient of methanol in dichloromethane to yield 532 mg (76%) of the title compound.

Alternatively, dissolve enantiomerically enriched 5-{hydroxy-[4-(2-piperidin-1-yl-ethoxy)-phenyl]-methyl}-6-(2,4,6-trifluoro-phenyl)-naphthalen-2-ol (804 mg, 1.59 mmol) in DMF (10 mL). Add potassium tert-butoxide (532 mg, 4.75 mmol). Heat at 50° C. for 2 minutes. Pour the reaction mixture into ice (5 g). Extract with ethyl acetate (100 mL). Separate the layers and wash the organic layer with 10% aqueous lithium chloride solution (20 mL×2). Dry with magnesium sulfate and concentrate in vacuo. Purify the residue over silica gel, eluting the material with a step gradient of methanol/dichloromethane (0 to 10%), to give the enantiomerically enriched title compound.

Example 86

8,10-Difluoro-5-[4-(2-piperidin-1-yl-ethoxy)-phenyl]-5H-6-oxa-chrysen-2-ol hydrochloride salt Dissolve 8,10-difluoro-5-[4-(2-piperidin-1-yl-ethoxy)-phenyl]-5H-6-oxa-chrysen-2-ol (532 mg, 1.1 mmol) in dichloromethane (10 mL) and add 2M HCl (1.1 mL, 2.2 mmol) and stir for 10 minutes. Concentrate in vacuo to yield 536 mg (100%) of the title compound. Mass spectrum (ion spray): m/z=488 (M+H−HCl). Separate the racemate into its constituent enantiomers by chiral chromatography. Conditions: Column: Chiralcel OD 4.6×150 mm; Eluent: 0.2% DMEA, 5% MeOH, 10% 3A Alcohol in Heptane.

Alternatively, dissolve enantiomerically enriched free base in diethyl ether (4 mL), ethyl acetate (1 mL) and methanol (0.5 mL) and cool to 0° C. Add 2M HCl in diethyl ether (2 mL, 20 mmol). Concentrate the slurry and dry in vacuo to give

Example 87

[4-(2-Azepan-1-yl-ethoxy)-phenyl]-[6-methoxy-2-(2,3,6-trifluoro-phenyl)-naphthalen-1-yl]-methanone

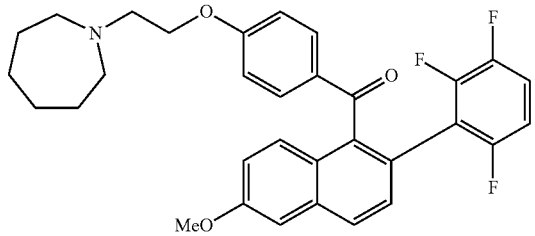

Couple trifluoromethanesulfonic acid 1-[4-(2-azepan-1-yl-ethoxy)-benzoyl]-6-methoxynaphthalen-2-yl ester (1.48 g, 2.67 mmol) with 2-bromo-1,3,4-trifluoro-benzene (1.13 g, 5.35 mmol) in a procedure similar to the preparation of [6-hydroxy-2-(2,3,5-trifluoro-phenyl)-naphthalen-1-yl]-[4-(2-piperidin-1-yl-ethoxy)-phenyl]-methanone to give 660 mg (46%) of the title compound: mass spectrum (ion spray): m/z=534.4 (M+H).

Example 88

[4-(2-Azepan-1-yl-ethoxy)-phenyl]-[6-hydroxy-2-(2,3,6-trifluoro-phenyl)-naphthalen-1-yl]-methanone Demethylate[4-(2-azepan-1-yl-ethoxy)-phenyl]-[6-methoxy-2-(2,3,6-trifluoro-phenyl)-naphthalen-1-yl]-methanone (0.66 g, 1.24 mmol) with $BBr_3$ in a procedure similar to the preparation of [6-hydroxy-2-(2,4,6-trifluoro-phenyl)-naphthalen-1-yl]-[4-(2-piperidin-1-yl-ethoxy)-phenyl]-methanone to give 530 mg (82%) of the title compound. Mass spectrum (ion spray): m/z=520.3 (M+H−HCl).

Example 89

5-[4-(2-Azepan-1-yl-ethoxy)-phenyl]-7,10-difluoro-5H-6-oxa-chrysen-2-ol hydrochloride salt

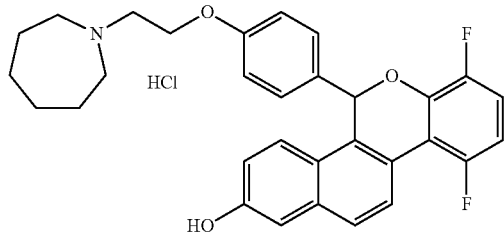

Dissolve [4-(2-azepan-1-yl-ethoxy)-phenyl]-[6-hydroxy-2-(2,3,6-trifluoro-phenyl)-naphthalen-1-yl]-methanone (529 mg, 1.02 mmol) in dioxane (205 mL). Flush the flask with $N_2$, then add $LiBHEt_3$ (4.1 mL, 4.1 mmol, 1.0 M in THF). Stir the reaction at room temperature for one hour then heat the reaction to 100° C. Continue to heat the reaction for 4 hours then cool it to room temperature. Add saturated $NH_4Cl$ solution (200 mL) and extract the aqueous layer with $CH_2Cl_2$ (3×200 mL). Combine the organic layers and dry with $Na_2SO_4$, filter, concentrate and purify by flash column chromatography (silica gel, 2-8% methanol (MeOH)—$NH_4OH$ (10/1, v/v)/$CH_2Cl_2$) to give 401 mg (79%) of product. Dissolve the above product (401 mg, 0.80 mmol) in $CH_2Cl_2$ (8 mL), and cool it to −78° C. Add HCl (0.8 mL, 2.0 M in $Et_2O$), and stir the solution for 10 minutes. Remove the solvent under reduced pressure. Dry the resulting solid at 40° C., overnight, in vacuo to give 432 mg (100%) of the title compound. Mass spectrum (ion spray): m/z=502.3 (M+H−HCl).

Example 90

[6-Methoxy-2-(2,3,6-trifluoro-phenyl)-naphthalen-1-yl]-[4-(2-piperidin-1-yl-ethoxy)-phenyl]-methanone

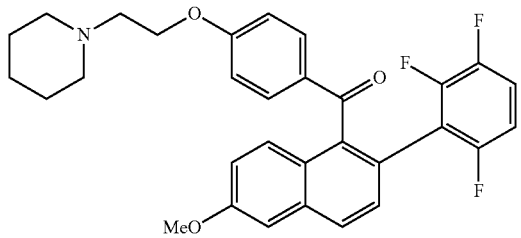

Couple trifluoromethanesulfonic acid 6-methoxy-1-[4-(2-piperidin-1-yl-ethoxy)-benzoyl]-naphthalen-2-yl ester (1.81 g, 3.37 mmol) with 2-bromo-1,3,4-trifluoro-benzene (1.42 g, 6.75 mmol) in a procedure similar to the preparation of [6-hydroxy-2-(2,3,5-trifluoro-phenyl)-naphthalen-1-yl]-[4-(2-piperidin-1-yl-ethoxy)-phenyl]-methanone to give 0.79 g (45%) of the title compound: mass spectrum (ion spray): m/z=520.3 (M+1).

Example 91

[6-Hydroxy-2-(2,3,6-trifluoro-phenyl)-naphthalen-1-yl]-[4-(2-piperidin-1-yl-ethoxy)-phenyl]-methanone Demethylate[6-methoxy-2-(2,3,6-trifluoro-phenyl)-naphthalen-1-yl]-[4-(2-piperidin-1-yl-ethoxy)-phenyl]-methanone (0.79 g, 1.52 mmol) with $BBr_3$ in a procedure similar to the preparation of [6-hydroxy-2-(2,4,6-trifluoro-phenyl)-naphthalen-1-yl]-[4-(2-piperidin-1-yl-ethoxy)-phenyl]-methanone to give 0.67 g (88%) of the title compound: mass spectrum (ion spray): m/z=506.3 (M+H).

Example 92

5-{Hydroxy-[4-(2-piperidin-1-yl-ethoxy)-phenyl]-methyl}-6-(2,3,5-trifluoro-phenyl)-naphthalen-2-ol Add (R)-(+)-α,α-diphenyl-2-pyrrolidinemethanol (0.06 g, 0.24 mmol) to a solution of $BH_3$.THF (6.0 mL, 6.0 mmol, 1.0 M in THF) in THF (10 mL) under a slow $N_2$ purge with stirring. Heat the solution to 45° C. Add dropwise a solution of [6-hydroxy-2-(2,3,6-trifluoro-phenyl)-naphthalen-1-yl]-[4-(2-piperidin-1-yl-ethoxy)-phenyl]-methanone (0.60 g, 1.20 mmol) in dry THF (25 mL) with syringe pump over 1.5 hours at 45° C. Continue to heat the reaction for another hour at 45° C. then cool it to room temperature. Add ethanolamine (0.66 g, 10.8 mmol), and continue to stir the mixture overnight. Add water (200 mL) and extract the aqueous layer with $CH_2Cl_2$ (3×200 mL). Combine the organic layers and dry (Previous page continuation:) enantiomerically enriched title compound (480 mg, 58% yield): mass spectrum (ion spray) m/z=488.3 (M−Cl).

with Na$_2$SO$_4$, filter, concentrate and purify by flash column chromatography (silica gel, 2-8% MeOH—NH$_4$OH (10/1, v/v)/CH$_2$Cl$_2$) to give 0.58 g (96%) of the title compound.

Example 93

7,10-Difluoro-5-[4-(2-piperidin-1-yl-ethoxy)-phenyl]-5H-6-oxa-chrysen-2-ol hydrochloride

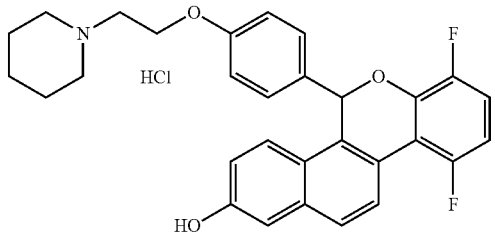

Dissolve 5-{hydroxy-[4-(2-piperidin-1-yl-ethoxy)-phenyl]-methyl}-6-(2,3,5-trifluoro-phenyl)-naphthalen-2-ol (0.58 g, 1.14 mmol) in dry DMF (20 mL). Add t-BuOK (0.39 g, 3.43 mmol) with stirring. Flush the flask with N$_2$, then heat the reaction mixture to 50° C. Continue to heat the reaction mixture for 20 minutes then cool it to room temperature. Add saturated NH$_4$Cl solution (100 mL), and extract the aqueous layer with CH$_2$Cl$_2$ (3×100 mL). Combine the organic layers and dry with Na$_2$SO$_4$, filter, concentrate and purify by flash column chromatography (silica gel, 2-8% MeOH—NH$_4$OH (10/1, v/v)/CH$_2$Cl$_2$) to give 0.56 g (99%) of the free base of title compound. Dissolve the free base (0.56 g, 1.14 mmol) in CH$_2$Cl$_2$ (10 mL), and cool it to −78° C. Add HCl (1.20 mL, 2.0 M in Et$_2$O), and stir the solution for 10 minutes. Remove the solvent under reduced pressure. Dry the solid at 40° C., overnight, in vacuo to give 0.60 g (100%) of the title compound: mass spectrum (ion spray) m/z=488.2 (M−Cl).

Preparation 12

3,5-Difluoro-2-methylsulfanyl-benzene boronic acid

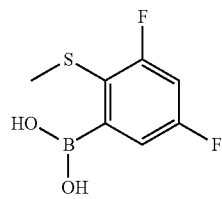

Dissolve 2-bromo-4,6-difluoroaniline (40 g, 192 mmol) in methyldisulfide (250 mL) and heat to 75° C. under nitrogen. Add isoamyl nitrite (67 mL, 500 mmol) dropwise via an addition funnel trough a reflux condenser (~1 drop/sec). Large exotherm may occur if addition is too fast. After addition is complete, heat the reaction to 95° C. for 1 hour and cool to room temperature and concentrate in vacuo. Purify dark brown residue via silica gel chromatography eluting with hexanes to yield 30.3 g of 1-bromo-3,5-difluoro-2-methylsulfanyl-benzene (66%).

Charge a flask with isopropyl magnesium chloride (145 mL, 2M in THF, 290 mmol) and dilute with tetrahydrofuran (150 mL) and heat to 40° C. under nitrogen. Add 1-bromo-3,5-difluoro-2-methylsulfanyl-benzene (28 g, 117 mmol) slowly over 5 minutes. After 30 minutes, cool the reaction to 0° C. and add trimethylborate (46 mL, 410 mmol) diluted with tetrahydrofuran (100 mL) via an addition funnel over 5 minutes. Partition the resulting gelatinous mixture between methylene chloride and 1N HCl. Acidify the aqueous layer to pH~1 (if needed) and vigorously stir the biphasic mixture until all solids are dissolved. Separate the organic layer. Dry over sodium sulfate, filter and concentrate. Triturate with hexanes and filter to yield 14.7 g (61%) of the title compound.

Example 94

Methanesulfonic acid 6-(3,5-difluoro-2-methylsulfanyl-phenyl)-5-[4-(2-piperidin-1-yl-ethoxy)-benzoyl]-naphthalen-2-yl ester

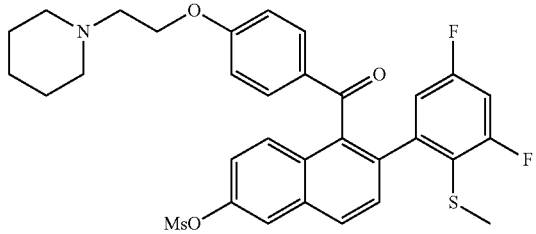

Charge a flask with trifluoromethanesulfonic acid 6-methanesulfonyloxy-1-[4-(2-piperidin-1-yl-ethoxy)-benzoyl]-naphthalen-2-yl ester (8.8 g, 14.6 mmol) and 3,5-difluoro-2-methylsulfanyl-benzene boronic acid (9.0 g, 42 mmol) and flush with nitrogen. Dissolve solids in degassed dioxane (240 mL). Add 2M sodium carbonate (120 mL) and Pd(PPh$_3$)$_4$ (6.7 g, 5.9 mmol). Plunge into 110° C. oil bath and stir vigorously. After 30 minutes, cool the reaction to room temperature and filter off solids. Partition the filtrate between water and methylene chloride. Wash the organic layer with water twice, dry over sodium sulfate, filter and concentrate. Purify the residue over silica gel, eluting with 1 to 2% methanol in methylene chloride, to yield 8.0 g (90%) of the title compound. LCMS R$_t$ (0.01% heptafluorobutyric acid:1.0% isopropylalcohol:water is mobile phase A and 0.01% heptafluorobutyric acid:1.0% isopropylalcohol:acetonitrile is mobile phase B; gradient method 25 to 95% B, Purity@254 nm)=3.18 mm (99%); mass spectrum (ion spray): m/z=612.3 (M+H).

Example 95

Methanesulfonic acid 6-(3,5-difluoro-2-methylsulfanyl-phenyl)-5-{hydroxy-[4-(2-piperidin-1-yl-ethoxy)-phenyl]-methyl}-naphthalen-2-yl ester Charge a flask with (S)-α,α-diphenyl-2-pyrrolidinemethanol (253 mg, 1.0 mmol) and purge flask with nitrogen. Dilute with 1M borane in THF (43 mL, 43 mmol) and heat to 45° C. under nitrogen. Dissolve methanesulfonic acid 6-(3,5-difluoro-2-methylsulfanyl-phenyl)-5-[4-(2-piperidin-1-yl-ethoxy)-benzoyl]-naphthalen-2-yl ester (6.5 g, 10.6 mmol) in THF (40 mL) and add to the catalyst solution via syringe pump over 2 hours. After complete addition, add ethanolamine (12.8 mL, 212 mmol) slowly and heat at 45° C. for 3 hours. Cool the reaction to room temperature and pour into saturated aqueous ammonium chloride. Extract with methylene chloride, dry over sodium sulfate, filter and concentrate. Purify over silica gel eluting with 3% methanol in methylene chloride to yield 7.4 g (93%) of the title compound (60:40 mixture of diastereomers). LCMS R$_t$ (0.01% heptafluorobutyric acid:1.0% isopropylalcohol:water is mobile phase A and 0.01% heptafluorobutyric acid:1.0% isopropylalcohol:acetonitrile is mobile phase B; gradient method 25 to 95% B, Purity@254 nm)=2.91 and 2.94 mm (100%); mass spectrum (ion spray): m/z=614.2 (M+H).

Example 96

Methanesulfonic acid 7,9-difluoro-5-[4-(2-piperidin-1-yl-ethoxy)-phenyl]-5H-6-thia-chrysen-2-yl ester

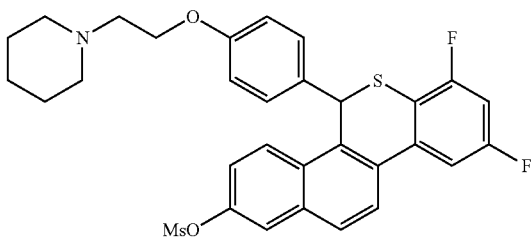

Dissolve methanesulfonic acid 6-(3,5-difluoro-2-methylsulfanyl-phenyl)-5-{hydroxy-[4-(2-piperidin-1-yl-ethoxy)-phenyl]-methyl}-naphthalen-2-yl ester (7.4 g, 12 mmol) in dry methylene chloride (200 mL) and purge with nitrogen. Add triethylamine (8.3 mL, 60 mmol) followed by methanesulfonyl chloride (4.6 mL, 60 mmol). After 30 minutes, pour reaction into water and extract with methylene chloride. Wash organic layer with water, dry over sodium sulfate, filter and concentrate. Purify over silica gel, eluting with 0 to 3% methanol in methylene chloride, to yield 5.2 g (74%) of the title compound. LCMS R$_t$ (0.01% heptafluorobutyric acid: 1.0% isopropylalcohol:water is mobile phase A and 0.01% heptafluorobutyric acid:1.0% isopropylalcohol:acetonitrile is mobile phase B; gradient method 25 to 95% B, Purity@254 nm)=3.34 min (100%); mass spectrum (ion spray): m/z=582.2 (M+H).

Example 97

7,9-Difluoro-5-[4-(2-piperidin-1-yl-ethoxy)-phenyl]-5H-6-thia-chrysen-2-ol hydrochloride salt Dissolve methanesulfonic acid 7,9-difluoro-5-[4-(2-piperidin-1-yl-ethoxy)-phenyl]-5H-6-thia-chrysen-2-yl ester (5.2 g, 9.0 mmol) in methanol (150 mL). Add potassium hydroxide (5.0 g, 90 mmol) and stir at room temperature. After 4 hours pour into saturated aqueous ammonium chloride and extract with methylene chloride. Dry over sodium sulfate, filter and concentrate. Dissolve residue in methylene chloride (90 mL) and add 2M HCl in ether (9 mL, 18 mmol). Concentrate in vacuo to yield 4.8 g (99%) of the title compound. LCMS R$_t$ (0.01% heptafluorobutyric acid:1.0% isopropylalcohol:water is mobile phase A and 0.01% heptafluorobutyric acid:1.0% isopropylalcohol:acetonitrile is mobile phase B; gradient method 15 to 95% B, Purity@254 nm)=3.21 min (100%); mass spectrum (ion spray): m/z=504.3 (M+H). Chiral HPLC: 87%.

Preparation 13

2-Methylsulfanyl-4-fluoro-benzene boronic acid

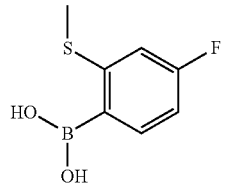

Dissolve 2-bromo-5-fluoroaniline (25 g, 131 mmol) in methyldisulfide (220 mL) and heat to 75° C. under nitrogen. Add isoamyl nitrite (46 mL, 342 mmol) dropwise via an addition funnel trough a reflux condenser (~1 drop/sec). Large exotherm may occur if addition is too fast. After addition is complete heat the reaction to 95° C. for 1 hour and cool to room temperature and concentrate in vacuo. Purify residue twice via silica gel chromatography eluting with hexanes to yield 22 g of 1-bromo-4-fluoro-2-methylsulfanyl-benzene (76%).

Dissolve 1-bromo-4-fluoro-2-methylsulfanyl-benzene (22 g, 99.6 mmol) in dry THF (500 mL) and cool to −78° C. under nitrogen. Add butyl lithium (2.5M in hexanes, 48 mL, 120 mmol) slowly and stir for 10 minutes after complete addition. Add trimethyl borate (22 mL, 200 mmol) and warm to room temperature. Pour into 0.1 M NaOH and extract with ether. Acidify the aqueous layer to pH 2 with concentrated HCl. Extract with ether, rry the organic layer with sodium sulfate, filter and concentrate in vacuo to yield 15.4 g (83%) of the title compound.

Example 98

Methanesulfonic acid 6-(4-fluoro-2-methylsulfanyl-phenyl)-5-[4-(2-piperidin-1-yl-ethoxy)-benzoyl]-naphthalen-2-yl ester

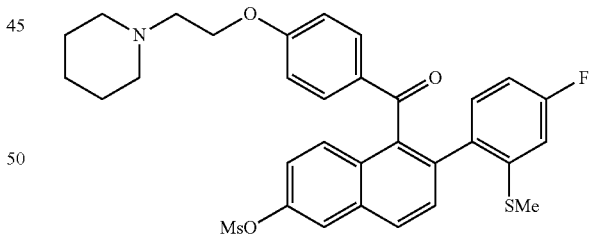

Charge a flask with trifluoromethanesulfonic acid 6-methanesulfonyloxy-1-[4-(2-piperidin-1-yl-ethoxy)-benzoyl]-naphthalen-2-yl ester (10.0 g, 16.6 mmol), 2-methylsulfanyl-4-fluoro-benzene boronic acid (7.7 g, 41.6 mmol), palladium acetate (371 mg, 1.66 mmol, tricyclohexylphosphine (700 mg, 2.5 mmol) and cesium fluoride (13 g, 83 mmol) and purge with nitrogen. Dilute with degassed acetonitrile (150 mL) and plunge into an 80° C. oil bath. Cool to room temperature after 1.5 hours and filter through celite and concentrate in vacuo. Partition the residue between methylene chloride and saturated aqueous sodium bicarbonate. Dry the organic layer with sodium sulfate, filter and concentrate. Purify the residue over a silica gel column, eluting with 2% methanol in methylene chloride, to yield 9.0 g (92%) of the title compound. LCMS R$_t$ (0.01% heptafluorobutyric acid:1.0% isopropylalcohol:water is mobile phase A and 0.01% heptafluorobutyric acid:1.0% isopropylalcohol:acetonitrile is mobile phase B; gradient method 25 to 95% B, Purity@254 nm)=2.92 min (95%); mass spectrum (ion spray): m/z=594.3 (M+H).

Example 99

Methanesulfonic acid 8-fluoro-5-[4-(2-piperidin-1-yl-ethoxy)-phenyl]-5H-6-thia-chrysen-2-yl ester

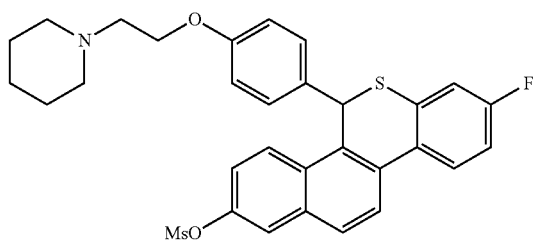

Charge a flask with (s)-(−)-α,α-diphenyl-2-pyrrolidinemethanol (380 mg, 1.5 mmol), dissolve with 1M borane in THF (60 mL, 60 mmol), purge with nitrogen and heat to 45° C. Dissolve methanesulfonic acid 6-(4-fluoro-2-methylsulfanyl-phenyl)-5-[4-(2-piperidin-1-yl-ethoxy)-benzoyl]-naphthalen-2-yl ester (9.0 g, 15.1 mmol) in dry THF (80 mL) and add to the borane solution via syringe pump over 2 hours. After the addition is complete, add ethanolamine (18.2 mL, 300 mmol) and stir at 45° C. for 3 hours. Pour the reaction into saturated aqueous ammonium chloride and extract with methylene chloride. Dry over sodium sulfate, filter and concentrate to a beige foam. Dissolve the crude foam in dry THF (150 mL). Add triethylamine (12.4 mL, 90 mmol) and methanesulfonyl chloride (7.0 mL, 90 mmol) and heat to reflux under nitrogen. Add more methanesulfonyl chloride (0.45 mL, 5.8 mmol) after 2 hours to drive the reaction to completion. Pour the reaction into saturated aqueous sodium bicarbonate and extract twice with methylene chloride. Dry the combined organic layers with sodium sulfate, filter and concentrate. Purify the residue on silica gel (0% to 4% methanol in methylene chloride) to yield 7.5 g (88%) of the title compound. HPLC R$_t$ (0.01% heptafluorobutyric acid:1.0% isopropylalcohol:water is mobile phase A and 0.01% heptafluorobutyric acid:1.0% isopropylalcohol:acetonitrile is mobile phase B; gradient method 25 to 95% B, Purity@254 nm)=2.96 min (100%); mass spectrum (ion spray): m/z=564.3 (M+H).

Example 100

8-Fluoro-5-[4-(2-piperidin-1-yl-ethoxy)-phenyl]-5H-6-thia-chrysen-2-ol hydrochloride Dissolve methanesulfonic acid 8-fluoro-5-[4-(2-piperidin-1-yl-ethoxy)-phenyl]-5H-6-thia-chrysen-2-yl ester (7.5 g, 13.3 mmol) in methanol (130 mL), add potassium hydroxide (7.5 g, 133 mmol) and stir at room temperature over night. Pour the reaction into saturated aqueous ammonium chloride and extract with methylene chloride. Dry organic layer with sodium sulfate, filter and concentrate in mow. Dissolve the resultant residue in methylene chloride (50 mL) and add 2M HCl in ether (10 mL). Remove the solvent in vacuo and redissolve in methylene chloride (10 mL). Add slowly to vigorously stirred ether. Collect the resulting precipitate and place in a 50° C. vacuum oven overnight to yield 5.7 g (82%) of the title compound. HPLC R$_t$ (0.01% heptafluorobutyric acid:1.0% isopropylalcohol:water is mobile phase A and 0.01% heptafluorobutyric acid:1.0% isopropylalcohol:acetonitrile is mobile phase B; gradient method 30 to 95% B, Purity@254 nm)=2.06 min (100%); mass spectrum (ion spray): m/z=486.3 (M−Cl). Chiral HPLC: 84% ee.

Example 101

[6-Benzyloxy-2-(2,4-difluoro-phenyl)-naphthalen-1-yl]-[4-(2-piperidin-1-yl-ethoxy)-phenyl]-methanone

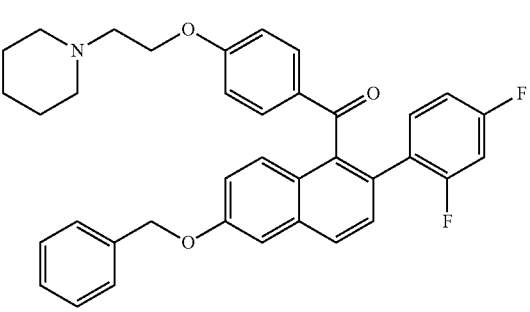

Add trifluoromethanesulfonic acid 6-benzyloxy-1-[4-(2-piperidin-1-yl-ethoxy)-benzoyl]-naphthalen-2-yl ester (0.45 g, 0.73 mmol), bis(neopentyl glycolato)diboron (0.18 g, 0.81 mmol), bis(tricyclohexylphosphine)palladium(0) (0.098 g, 0.15 mmol) and acetonitrile (7.5 mL) to a round bottom flask. Stir at ambient temperature for approximately 5 minutes to dissolve most of the reagents. Add cesium fluoride (1.00 g, 6.61 mmol), place the flask in a 90° C. oil bath, and stir under nitrogen for 2-3 minutes. Now add 1-bromo-2,4-difluorobenzene (0.174 mL, 1.54 mmol) and stir for 20 minutes. At this time add more 1-bromo-2,4-difluorobenzene (0.06 mL, 0.53 mmol) and continue stirring the reaction for 2 hours at 90° C. At this time add more 1-bromo-2,4-difluorobenzene (0.05 mL, 0.44 mmol) and continue stirring for another 2 hours. Cool the reaction to ambient temperature and then filter it through a pad of Celite. Rinse the pad with ample, hot ethyl acetate. Wash the filtrate in a separatory funnel with 50% aqueous sodium carbonate, saturated aqueous ammonium chloride, H$_2$O and brine; then dry (sodium sulfate) and evaporate it in vacuo. Load resulting material onto an SCX column, wash with dichloromethane, 50% dichloromethane/methanol, elute with ammonia solution (2N NH$_3$ in methanol) and remove solvent under vacuum. Purify the resulting residue by flash chromatography (silica gel; 1.5%-3% methanol gradient in dichloromethane) to provide 0.245 g (58%) of the title compound: mass spectrum (ion spray) m/z=578 (M+H).

Example 102

[2-(2,4-Difluoro-phenyl)-6-methoxy-naphthalen-1-yl]-[4-(2-piperidin-1-yl-ethoxy)-phenyl]-methanone Dissolve trifluoromethanesulfonic acid 6-methoxy-1-[4-(2-piperidin-1-yl-ethoxy)-benzoyl]-naphthalen-2-yl ester (12.4 g, 23.0 mmol) and 2,4-difluorophenylboronic acid (7.0 g, 46.0 mmol) in degassed dimethoxyethane (620 mL). Add 2M aqueous sodium carbonate (73 mL, 145 mmol) and stir at room temperature under nitrogen for 5 minutes. Add palladium(II) acetate (520 mg, 2.3 mmol) and triphenylphosphine (1.2 g, 4.6 mmol) and plunge into a 85° C. oil bath. Stir for 40 minutes and cool to room temperature. Pour into saturated aqueous sodium bicarbonate and extract twice with methylene chloride. Dry the combined organic layers with sodium sulfate, filter and concentrate in vacuo. Purify the resultant oil with SCX columns (load in methanol, elute with 2M NH$_3$/MeOH) to yield 10.8 g (93%) of the title compound: mass spectrum (ion spray) m/z=502.3 (M+H).

Example 103

[2-(2,4-difluoro-phenyl)-6-hydroxy-naphthalen-1-yl]-[4-(2-piperidin-1-yl-ethoxy)-phenyl]-methanone Dissolve [2-(2,4-difluoro-phenyl)-6-methoxynaphthalen-1-yl]-[4-(2-piperidin-1-yl-ethoxy)-phenyl]-methanone (10.8 g, 21.5 mmol) in methylene chloride (200 mL). Add 2M HCl in ether (21.5 mL, 43 mmol) and concentrate in vacuo. Redissolve the foam in methylene chloride (200 mL) and cool to 0° C. under nitrogen. Slowly add boron tribromide (10.1 mL, 107 mmol) and stir at 0° C. for 30 minutes. Slowly pour into saturated aqueous sodium bicarbonate and extract with 20% WA in chloroform. Dry the organic layer with sodium sulfate, filter and concentrate in vacuo to yield 10.5 g (100%) of the title compound.

Example 104

6-(2,4-difluoro-phenyl)-5-{hydroxy-[4-(2-piperidin-1-yl-ethoxy)-phenyl]-methyl}-naphthalen-2-ol Dissolve [2-(2,4-difluoro-phenyl)-6-hydroxy-naphthalen-1-yl]-[4-(2-piperidin-1-yl-ethoxy)-phenyl]-methanone (3.3 g, 6.8 mmol) in dry THF (100 mL) and stir under nitrogen. Slowly add lithium aluminum hydride (0.9 g, 24 mmol) and heat to reflux. Cool to room temperature after 30 minutes and quench excess LiAlH$_4$ with slow addition of ice. Dilute with water and adjust the pH to 7 with 1M HCl. Extract five times with 20% IPA in chloroform. Dry the combined organic layers with sodium sulfate, filter and concentrate in vacuo to yield 3.4 g (100%) of the title compound.

Example 105

8-Fluoro-5-[4-(2-piperidin-1-yl-ethoxy)-phenyl]-5H-6-oxa-chrysen-2-ol

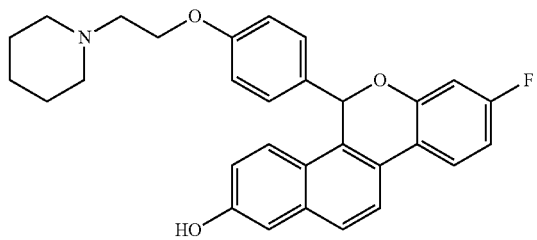

Dissolve 6-(2,4-difluoro-phenyl)-5-{hydroxy-[4-(2-piperidin-1-yl-ethoxy)-phenyl]-methyl}-naphthalen-2-ol (3.4 g, 7.0 mmol) in dry DMF (70 mL). Slowly add sodium hydride (440 mg, 18 mmol) and plunge into a 140° C. oil bath for 30 minutes. Cool to room temperature and pour into water. Adjust the pH to 7 and extract three times with methylene chloride. Wash combined organic layers with water, dry with sodium sulfate, filter and concentrate. Triturate with ether to yield 2.2 g (69%) of the title compound: mass spectrum (ion spray) m/z=470.3 (M+H).

Example 106

[2-(2,6-Difluoro-phenyl)-6-methoxy-naphthalen-1-yl]-[4-(2-piperidin-1-yl-ethoxy)-phenyl]-methanone

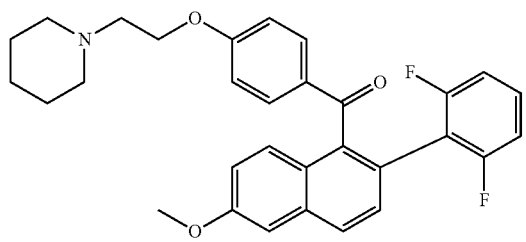

Charge a flask with trifluoromethanesulfonic acid 6-methoxy-1-[4-(2-piperidin-1-yl-ethoxy)-benzoyl]-naphthalen-2-yl ester (2.0 g, 3.7 mmol), 2,6-difluorophenyl boronic acid (1.17 g, 7.4 mmol), tetrakis(triphenylphosphine)palladium (0) (855 mg, 0.74 mmol) and potassium phosphate (4.7 g, 22.2 mmol) add 100 mL of dry DMF and heat under nitrogen at 100° C. for two hours. Cool the reaction and filter. Purify on an SCX column eluting with 2N ammonia/methanol. Purify further on a silica gel column eluting with a gradient of 0-10% methanol/methylene chloride. The yield is 1.5 g (81%). 1H-NMR (CDCl$_3$, 400 MHz) δ7.90 (d, J=8.4 Hz, 1H); 7.63 (d, J=8.4 Hz, 1H); 7.62 (d, J=9.2 Hz, 2H); 7.39 (d, J=8.4 Hz, 1H); 7.23 (d, J=2.8 Hz, 1H); 7.18-7.08 (m, 2H); 6.78 (d, J=10.4 Hz, 2H); 6.74 (s, 2H); 4.11-4.08 (m, 2H); 3.95 (s, 3H); 2.75 (t, J=6.4 Hz, 2H); 2.49-2.49 (m, 4H); 1.63-1.58 (m, 4H); 1.47-1.44 (m, 2H).

Example 107

[2-(2,6-Difluoro-phenyl)-6-hydroxy-naphthalen-1-yl]-[4-(2-piperidin-1-yl-ethoxy)-phenyl]-methanone Dissolve [2-(2,6-difluorophenyl)-6-methoxy-naphthalen-1-yl]-[4-(2-piperidin-1-ylethoxy)-phenyl]-methanone (1.5 g, 3.0 mmol) in 500 mL methylene chloride and chill in ice. To this solution add boron tribromide (6.0 mL, 63 mmol) in portions with swirling between additions. Allow to come to room temperature and stir for one hour. Pour into a two-phase system consisting of an organic layer of 3/1 chloroform/isopropanol and an aqueous layer of saturated sodium bicarbonate. Separate the phases and dry the organic layer using 3 Å molecular sieves. Purify on a silica column eluting with a 0-10% methanol/methylene chloride gradient to give 600 mg (44%) of the title compound.

Example 108

10-Fluoro-5-[4-(2-piperidin-1-yl-ethoxy)-phenyl]-5H-6-oxa-chrysen-2-ol hydrochloride

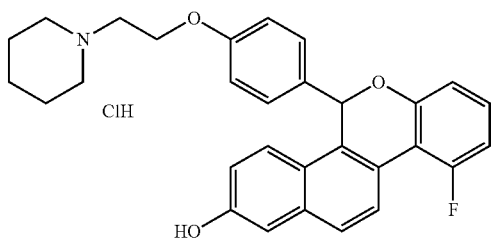

Charge a flask with 100 mL of dioxane and add 1 M borane-THF (5.0 mL, 5.0 mmol) under nitrogen followed by R-Methyl CBS reagent (51 mg, 0.18 mmol) and heat the mixture to 45° C. Prepare a solution of [2-(2,6-difluoro-phenyl)-6-hydroxy-naphthalen-1-yl]-[4-(2-piperidin-1-yl-ethoxy)-phenyl]-methanone (580 mg, 1.19 mmol) in 200 mL dioxane and add this to the reaction mixture dropwise over one hour. Monitor the reaction by LC/MS and continue heating until complete (about two hours). Add to this reaction 20 mL of 1.0 M lithium triethylborohydride and heat at 95° C. for 24 hours or until reaction is complete by LC/MS. Cool the reaction and quench with isopropanol. Evaporate the solvent and partition between a 3/1 mixture of chloroform/isopropanol and saturated sodium bicarbonate. Separate the organic layer and dry over 3 Å molecular sieves. Purify on a silica gel column eluting with a 0-10% methanol/methylene chloride gradient. The yield is 460 mg (82%). Convert to HCl salt: $^1$H-NMR (Free base CD$_3$OD, 400 MHz) δ8.11 (d, J=8.8 Hz, 1H); 7.71 (d, J=8.8 Hz, 1H); 7.57 (d, J=9.2 Hz, 1H); 717 (d, J=2.8 Hz, 1H); 7.02-6.89 (m, 5H); 6.67-6.57 (m, 4H); 3.84-3.79 (t, 2H); 2.56 (t, J=6.0 Hz, 2H); 2.36-2.36 (m, 4H); 1.52-1.46 (m, 4H); 1.37-1.35 (m, 2H).

Example 109

[2-(2,3-Difluoro-phenyl)-6-methoxy-naphthalen-1-yl]-[4-(2-piperidin-1-yl-ethoxy)-phenyl]-methanone

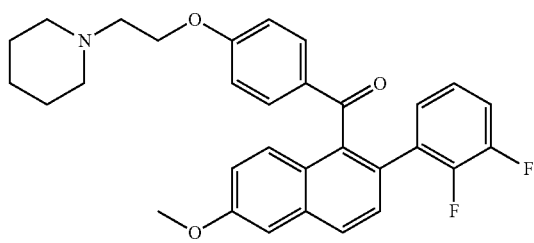

Charge a flask with trifluoromethanesulfonic acid 6-methoxy-1-[4-(2-piperidin-1-yl-ethoxy)-benzoyl]-naphthalen-2-yl ester (2.0 g, 3.7 mmol), 2,3 difluorophenyl boronic acid (1.17 g, 7.4 mmol) palladium dichloride bis(triphenylphosphine) (518 mg, 0.74 mmol) and cesium fluoride (5.06 g, 33.3 mmol) and add 250 mL degassed acetonitrile. Heat the mixture at 85° C. for two hours, cool the reaction and filter off any solids. Purify on an SCX column eluting with 2N ammonia/methanol. Purify further on a silica gel column eluting with a 0-10% methanol/methylene chloride gradient to give 1.3 g (70%) of the title compound: 1H-NMR (CD$_3$OD, 400 MHz) δ7.92 (d, J=8.8 Hz, 1H); 7.54 (dd, J=8.4, 4.0 Hz, 3H); 7.43 (dd, J=8.4, 1.6 Hz, 1H); 7.31 (d, J=2.8 Hz, 1H); 7.09 (dd, J=9.2, 2.4 Hz, 1H); 7.05-6.92 (m, 3H); 6.79 (d, J=8.8 Hz, 2H); 4.10 (t, J=5.6 Hz, 2H); 3.93 (s, 3H); 2.73 (t, J=5.2 Hz, 2H); 2.50-2.50 (m, 4H); 1.62-1.57 (m, 4H); 1.48-1.43 (m, 2H).

Example 110

[2-(2,3-Difluoro-phenyl)-6-hydroxy-naphthalen-1-yl]-[4-(2-piperidin-1-yl-ethoxy)-phenyl]-methanone Charge a flask with [2-(2,3-difluoro-phenyl)-6-methoxy-naphthalen-1-yl]-[4-(2-piperidin-1-yl-ethoxy)-phenyl]-methanone (1.3 g, 2.6 mmol) and add 200 mL methylene chloride followed by 25 mL of HCl in ether (1 M) and evaporate to dryness. Dissolve the solid in 200 mL methylene chloride and chill the solution in ice. Add to this solution boron tribromide (4.0 mL, 42.4 mmol) with swirling. Stir the dark solution at room temperature for 1 hour at which point all the starting material is gone. Pour this into a two phase mixture consisting of saturated sodium bicarbonate aqueous phase and a 3/1 mixture of chloroform/isopropanol organic phase and extract using a separatory funnel. Separate the organic phase and dry over 3 Å molecular sieves. Purify on a silica column eluting with 0-10% methanol/methylene chloride, collecting the first fraction that contains the product to give 400 mg of the title compound (32%).

Example 111

7-Fluoro-5-[4-(2-piperidin-1-yl-ethoxy)-phenyl]-5H-6-oxa-chrysen-2-ol hydrochloride

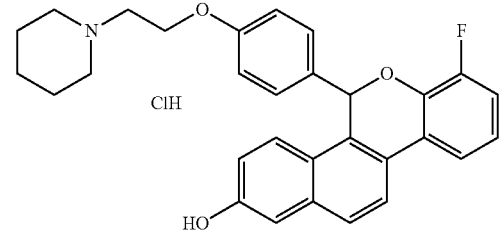

Charge a flask with R-methyl CBS reagent (50 m, 0.18 mmol) dissolved in 100 mL dioxane and warm to 45° C. Dissolve [2-(2,3-difluoro-phenyl)-6-hydroxy-naphthalen-1-yl]-[4-(2-piperidin-1-yl-ethoxy)-phenyl]-methanone (400 mg, 0.82 mmol) in 100 mL of dioxane and add dropwise to the reaction mixture over a two hour period. Continue heating at 45° C. under nitrogen overnight and add lithium triethylborohydride (15 mL of 1.0 M solution in THF, 15 mmol) and heat reaction to 100° C. for 24 hours. Cool the reaction mixture and add 25 mL of isopropanol to quench the reaction. Evaporate the reaction to an oil and add saturated sodium bicarbonate and a 3/1 mixture of chloroform/isopropanol. Extract in a separatory funnel and remove the organic layer. Dry the organic layer over 3 Å molecular sieves, evaporate to a paste and purify on a silica column eluting with 0-10% methanol/methylene chloride. Convert the isolated product to the HCl salt using HCl in ether to give 145 mg (35%) of the title compound. The two enantiomers are separated using chiral chromatography (Conditions D). The preferred isomer eluted second with a retention time of 16.5 minutes (98 mgs).

Example 112

[2-(2,5-Difluoro-phenyl)-6-methoxy-naphthalen-1-yl]-[4-(2-piperidin-1-yl-ethoxy)-phenyl]-methanone

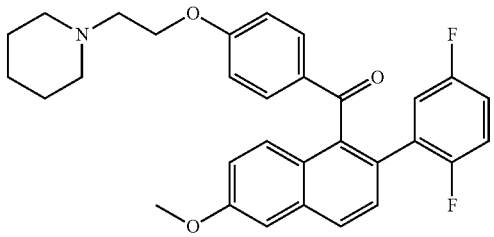

Add trifluoromethanesulfonic acid 6-methoxy-1-[4-(2-piperidin-1-yl-ethoxy)-benzoyl]-naphthalen-2-yl ester (552 mg, 1.0 mmol), 2,6-difluorophenyl boronic acid (320 mg, 2.0 mmol), trans dichlorobis(triphenylphosphine)palladium II (70 mg, 0.1 mmol) and cesium fluoride (1.3 g, 8.6 mmol) to a 20 mL vial along with 8.0 mL degassed acetonitrile. Seal the vial with a septum and purge with nitrogen gas. Heat the mixture with stirring at 80° C. for three hours. Cool, filter and purify on an SCX column, eluting with 2N ammonia/methanol. The compound is further purified on a silica gel column, eluting with a 0-5% 2N ammonia in methanol/methylene chloride gradient. The yield is 260 mg (50%).

Example 113

[2-(2,5-Difluorophenyl)-6-hydroxynaphthalen-1-yl]-[4-(2-piperidin-1-yl-ethoxy)-phenyl]-methanone Convert [2-(2,5-difluoro-phenyl)-6-methoxy-naphthalen-1-yl]-[4-(2-piperidin-1-yl-ethoxy)-phenyl]-methanone (1.8 g, 3.5 mmol) to the hydrochloride salt and dissolve it in 300 mL methylene chloride. Chill the mixture in ice and slowly add boron tribromide (5.0 mL, 53.0 mmol) with swirling. Allow the mixture to come to room temperature and stir for two hours. Add to this mixture acetonitrile (15 mL) slowly and with stirring which produces an orange precipitate. Pour the mixture into saturated sodium bicarbonate with stirring, separate the organic layer and dry with molecular sieves to give 1.5 g of the title compound (86%).

Example 114

9-Fluoro-5-[4-(2-piperidin-1-yl-ethoxy)-phenyl]-5H-6-oxa-chrysen-2-ol hydrochloride

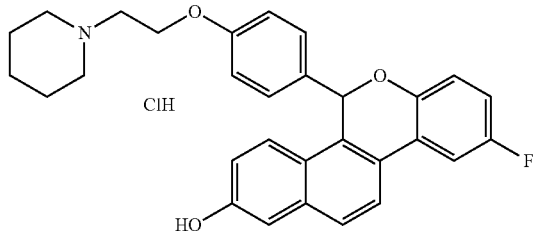

Charge a flask with (R)-(+)-α,α, diphenylprolinol (76.2 mg, 0.3 mmol) dissolved in a mixture of 24 mL of a 1.0 M solution of borane/THF and 500 mL THF and heat to 45° C. Add to this, via syringe pump over 8 hours, a solution of [2-(2,5-difluorophenyl)-6-hydroxynaphthalen-1-yl]-[4-(2-piperidin-1-yl-ethoxy)-phenyl]-methanone (1.5 g, 3.0 mmol) dissolved in 100 mL THF. Continue heating for two hours after complete addition and add 6.0 grams of potassium t-butoxide, and continue heating for two hours, then raise the temperature to 60° C. and heat for another five hours. Quench the reaction by cautiously adding saturated sodium bicarbonate solution. Evaporate most of the organic layer under vacuum and add a 3/1 mixture of chloroform/isopropanol and extract in a separatory funnel. Separate the layers and dry the organic layer over 3 Å molecular sieves. Evaporate the solvent to yield 1.0 g of impure product. Purify on a silica gel column eluting with 1.5% 2N ammonia/methanol/methylene chloride to give 620 mg (43%) of a product mixture that contained both enantiomers. The enantiomers are further purified and separated on a chiral column using a ChiralPak AD column, 4.6×250 mm using an eluent of 100% ethanol containing 0.2% dimethylethylamine and a flow rate of 1.0 ml/min. The preferred isomer (the $2^{nd}$ to elute) is converted to the HCl salt yielding 330 mg of final product (23%).

Example 115

[6-Methoxy-2-(2,3,4-trifluoro-phenyl)-naphthalen-1-yl]-[4-(2-piperidin-1-yl-ethoxy)-phenyl]-methanone

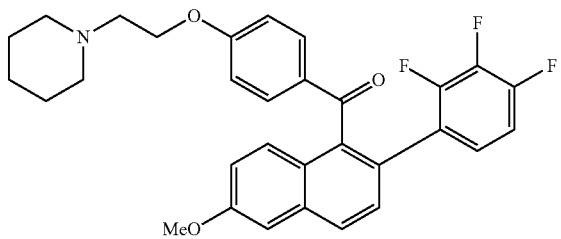

Charge a round bottom flask with trifluoromethanesulfonic acid 6-methoxy-1-[4-(2-piperidin-1-yl-ethoxy)-benzoyl]-naphthalen-2-yl ester (2.13 g, 4.0 mmol), 2,3,4-trifluorophenyl boronic acid (1.0 g, 5.7 mmol), trans-dichlorobis(triphenylphosphine)palladium II, (561 mg, 0.8 mmol) and cesium fluoride (5.5 g, 36 mmol) and add 50 mL of acetonitrile. Heat the mixture at 80° C. for 4 hours. Cool and filter the mixture and purify on an SCX column, eluting with 2N ammonia/methanol. Purify further on a silica column eluting with 2% 2N ammonia/methanol/methylene chloride. The yield is 880 mg (43%): 1H-NMR (CD3OD, 400 MHz) δ 7.93 (d, J=8.8 Hz, 1H); 7.50 (d, J=8.4 Hz, 3H); 7.39 (d, J=8.8 Hz, 1H); 7.35 (d, J=2.4 Hz, 1H); 7.07 (dd, J=9.2, 2.8 Hz, 1H); 6.96-6.87 (m, 2H); 6.80 (d, J=9.6 Hz, 2H); 4.10-4.07 (t, 2H); 3.91 (s, 3H); 2.72-2.69 (t, 2H); 2.48-2.48 (m, 4H); 1.61-1.55 (m, 4H); 1.46-1.43 (m, 2H).

Example 116

[6-hydroxy-2-(2,3,4-trifluoro-phenyl)-naphthalen-1-yl]-[4-(2-piperidin-1-yl-ethoxy)-phenyl]-methanone Dissolve [6-methoxy-2-(2,3,4-trifluoro-phenyl)-naphthalen-1-yl]-[4-(2-piperidin-1-yl-ethoxy)-phenyl]-methanone (880 mg, 1.69 mmol) in 100 mL methylene chloride and chill in ice. Add 4.0 mL of neat boron tribromide with swirling and stir in the ice bath for 30 minutes. Allow the mixture to come to room temperature and stir for an additional 1 hour. Carefully pour the mixture into a two-phase system consisting of saturated sodium bicarbonate solution and a 3/1 mixture of chloroform/isopropanol. Separate the organic layer, dry over 3 Å molecular sieves and evaporate to give 800 mg of slightly impure product. Purify on a silica gel column eluting with 3% methanol/methylene chloride to give 635 mg (74%) of the title compound.

Example 117

7,8-Difluoro-5-[4-(2-piperidin-1-yl-ethoxy)-phenyl]-5H-6-oxa-chrysen-2-ol hydrochloride

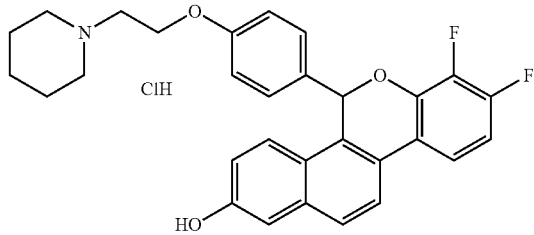

Charge a flask with [6-hydroxy-2-(2,3,4-trifluoro-phenyl)-naphthalen-1-yl]-[4-(2-piperidin-1-yl-ethoxy)-phenyl]-methanone (620 mg, 1.23 mmol) and add 250 mL dioxane. Start stirring and add to this 20 mL of a 1.0 M solution of lithium triethylborohydride in UV at room temperature. Stopper flask and stir for one hour. Heat the flask to 90° C. under nitrogen and follow reaction by LC/MS. Heat the reaction for a total of 18 hours. Pour the reaction into 300 mL of a mixture of 3/1 chloroform/isopropanol and 300 mL of saturated sodium bicarbonate solution. Separate the organic layer and dry over 3 Å molecular sieves. Evaporate to dryness and purify on a silica gel column eluting with 3% methanol/methylene chloride. Evaporate and convert to the hydrochloride salt using acetonitrile/water with 1N HCl and lyophilize. The yield is 295 mg (46%). 1H-NMR (CD$_3$OD, 400 MHz) δ7.90-7.87 (m, 1H); 7.79 (d, J=8.8 Hz, 1H); 7.65 (d, J=8.8 Hz, 1H); 7.59-7.55 (m, 1H); 7.19 (d, J=2.4 Hz, 1H); 7.11-7.05 (m, 3H); 6.88-6.83 (m, 1H); 6.81-6.75 (m, 2H); 4.10-4.07 (m, 2H); 2.93-2.91 (m, 2H); 2.71-2.71 (m, 4H); 1.67-1.63 (m, 4H); 1.51-1.50 (m, 2H). The racemic compound is purified using chiral chromatography using chiral chromatography (conditions O). The two isomers eluted with retention times of 5.2 and 7.4 minutes.

Example 118

[4-(2-Azepan-1-yl-ethoxy)-phenyl]-[2-(2,4-difluoro-phenyl)-6-methoxy-naphthalen-1-yl]-methanone

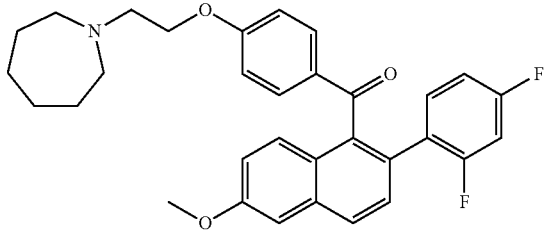

Couple trifluoromethanesulfonic acid 1-[4-(2-azepan-1-yl-ethoxy)-benzoyl]-6-methoxynaphthalen-2-yl ester (1.4 g, 2.5 mmol) and 2,4-difluorophenyl boronic acid (1.2 g, 7.6 mmol) by the procedure used to prepare [2-(2,4-difluoro-phenyl)-6-methoxy-naphthalen-1-yl]-[4-(2-piperidin-1-yl-ethoxy)-phenyl]-methanone to give yields 1.1 g (85%) of the title compound: mass spectrum (ion spray) m/z=516.3 (M+H).

Example 119

[4-(2-azepan-1-yl-ethoxy)-phenyl]-[2-(2,4-difluoro-phenyl)-6-hydroxy-naphthalen-1-yl]-methanone By the standard demethylation procedure found in the preparation of [2-(2,4-difluoro-phenyl)-6-hydroxy-naphthalen-1-yl]-[4-(2-piperidin-1-yl-ethoxy)-phenyl]-methanone, [4-(2-azepan-1-yl-ethoxy)-phenyl]-[2-(2,4-difluoro-phenyl)-6-methoxy-naphthalen-1-yl]-methanone (1.1 g, 2.1 mmol) is demethylated with BBr$_3$ (1.0 mL, 10.5 mmol) to afford crude product. Purify on silica gel (0% to 5% methanol in methylene chloride) to yield 790 mg (75%) of the title compound: mass spectrum (ion spray) m/z=502.3 (M+H).

Example 120

5-[4-(2-Azepan-1-yl-ethoxy)-phenyl]-8-fluoro-5H-6-oxa-chrysen-2-ol hydrochloride

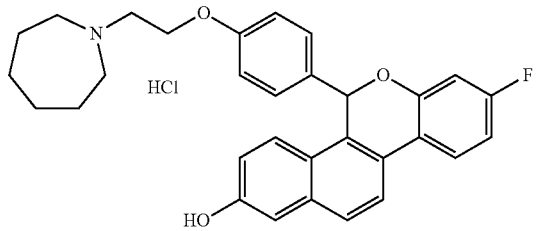

Dissolve [4-(2-azepan-1-yl-ethoxy)-phenyl]-[2-(2,4-difluoro-phenyl)-6-hydroxy-naphthalen-1-yl]-methanone (760 mg, 1.5 mmol) in dioxane (30 mL) and add LiBEt$_3$H (1M in THF, 4.5 mL, 4.5 mmol) dropwise. Stir at room temperature for 30 minutes then plunge into a 100° C. oil bath for 5 hours. Cool to room temperature overnight. Slowly add methanol (5 mL) and concentrate in vacuo. Dissolve the residue in methylene chloride and wash with saturated aqueous ammonium chloride and brine. Dry with sodium sulfate, filter and concentrate in vacuo. Purify the residue on silica gel (0% to 3% methanol in methylene chloride), concentrate, and suspend in methanol/chloroform. Add 2M HCl in ether (1 mL) and remove the solvent. Dry the residue in a vacuum oven overnight at 50° C. to yield 499 mg (64%) of the title compound: mass spectrum (ion spray) m/z=484.3 (M−Cl).

Example 121

[4-(2-Azepan-1-yl-ethoxy)-phenyl]-[2-(2,5-difluoro-phenyl)-6-methoxy-naphthalen-1-yl]-methanone

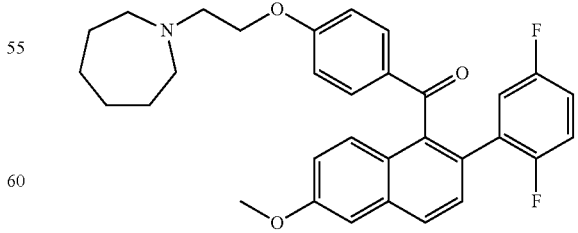

Dissolve trifluoromethanesulfonic acid 1-[4-(2-azepan-1-yl-ethoxy)-benzoyl]-6-methoxynaphthalen-2-yl ester (2.00 g, 3.63 mmol) in 5 mL of degassed acetonitrile and add 2,5-difluorophenyl boronic acid (1.15 g, 7.26 mmol), trans

[dichlorobis(triphenylphosphine)]palladium II (0.51 g, 0.73 mmol) and sonicate briefly. Next add cesium fluoride (4.96 g, 32.76 mmol) and heat to 75° C. for one hour. Add Celite and filter. Concentrate the solvent under vacuum, dissolve in methanol and purify on an SCX cartridge, eluting with 2N ammonia/methanol to give 1.74 g (93%) of the title compound.

Example 122

[4-(2-azepan-1-yl-ethoxy)-phenyl]-[2-(2,5-difluorophenyl)-6-hydroxynaphthalen-1-yl]-methanone Dissolve [4-(2-azepan-1-yl-ethoxy)-phenyl]-[2-(2,5-difluoro-phenyl)-6-methoxy-naphthalen-1-yl]-methanone (1.74 g, 3.37 mmol) in 20 mL methylene chloride and chill in ice. Add to this solution 2.0 mL of boron tribromide (5.3 g, 21.2 mmol) and allow to come to room temperature. Pour into a two phase solution of saturated sodium bicarbonate and 3/1 chloroform/isopropanol. Separate the organic layer, wash with water and dry over 3 Å sieves. Evaporate the solvent and purify on a silica gel column eluting with a 0-10% methanol/methylene chloride gradient. Evaporate the solvent to yield 780 mg (46%) of the title compound.

Example 123

5-{[4-(2-azepan-1-yl-ethoxy)-phenyl]-hydroxymethyl}-6-(2,5-difluorophenyl)-naphthalen-2-ol Dissolve [4-(2-azepan-1-yl-ethoxy)-phenyl]-[2-(2,5-difluorophenyl)-6-hydroxynaphthalen-1-yl]-methanone (770 mg, 1.54 mmol) in 10 mL THF and add 5.0 mL (5.0 mmol) of lithium triethylborohydride (1.0 M solution in THF). After one hour at room temp, add another 4.0 mL of the lithium triethylborohydride gently warm the solution with a heat gun. After ½ hour the reaction is complete. Quench the reaction with water and pour into a two phase system of saturated sodium bicarbonate and a 3/1 mixture of chloroform/isopropanol. Separate the phases, dry the organic layer with 3 Å sieves and evaporate to give the title compound to be taken on to the next step without purification.

Example 124

5-[4-(2-Azepan-1-yl-ethoxy)-phenyl]-9-fluoro-5H-6-oxa-chrysen-2-ol

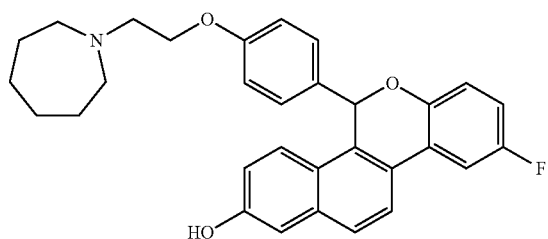

Dissolve 5-{[4-(2-azepan-1-yl-ethoxy)-phenyl]-hydroxymethyl}-6-(2,5-difluorophenyl)-naphthalen-2-ol (770 mg, 1.54 mmol) in 20 mL dry DMF and add sodium t-butoxide (1.18 g, 12.32 mmol). Heat the mixture to 50° C. for two hours. Dilute with water and extract multiple times with methylene chloride. Dry the organic layer and purify on a silica gel column eluting with a 0-10% methanol/methylene chloride gradient. The yield is 370 mg (50%): 1H-NMR (CDCl$_3$, 300 MHz) δ7.76 (dd, J=12.6, 8.4 Hz, 2H); 7.58 (d, J=9.0 Hz, 1H); 7.43-7.40 (m, 1H); 7.15 (d, J=2.4 Hz, 1H); 7.05-7.01 (m, 3H); 6.89 (s, 1H); 6.83-6.80 (m, 2H); 6.66-6.63 (m, 2H); 4.00-3.98 (m, 2H); 2.92-2.92 (m, 2H); 2.78-2.78 (m, 4H); 1.66-1.59 (m, 8H). The racemic compound is purified using chiral chromatography (conditions P). The two isomers eluted with retention times of 9.9 and 13.5 minutes.

Example 125

[4-(2-azepan-1-yl-ethoxy)-phenyl]-[2-(2,6-difluorophenyl)-6-methoxy-naphthalen-1-yl]-methanone

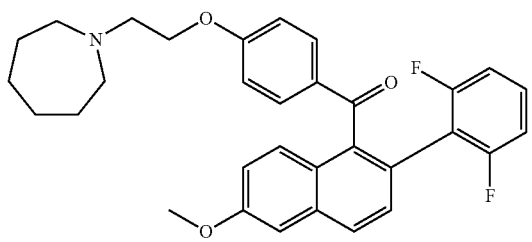

Charge a flask with trifluoromethanesulfonic acid 1-[4-(2-azepan-1-yl-ethoxy)-benzoyl]-6-methoxynaphthalen-2-yl ester (3.9 g, 7.06 mmol), 2,6-difluorophenyl boronic acid (2.23 g, 14.12 mmol), potassium phosphate (9.0 g, 42.20 mmol) and tetrakis(triphenylphosphine)palladium (0) (1.63 g, 1.40 mmol) followed by 125 mL dry DMF. Heat the mixture under nitrogen at 100° C. for 90 minutes. Cool, filter, evaporate the solvent and purify on an SCX cartridge, eluting with 2N ammonia/methanol. Purify further on a silica gel column eluting with 0-10% methanol/methylene chloride. The yield is 2.5 g (70%): $^1$H-NMR (CDCl$_3$, 400 MHz) δ7.90 (d, J=8.4 Hz, 1H); 7.66-7.61 (m, 3H); 7.39 (d, J=8.4 Hz, 1H); 7.23-722 (m, 1H); 7.18-7.08 (m, 2H); 6.79-6.74 (m, 4H); 4.08-4.05 (t, 2H); 3.95 (s, 3H); 2.96-2.89 (t, 2H); 2.78-2.75 (m, 4H); 1.66-1.59 (m, 8H).

Example 126

[4-(2-Azepan-1-yl-ethoxy)-phenyl]-[2-(2,6-difluorophenyl)-6-hydroxy-naphthalen-1-yl]-methanone Convert [4-(2-azepan-1-yl-ethoxy)-phenyl]-[2-(2,6-difluoro-phenyl)-6-methoxy-naphthalen-1-yl]-methanone (2.5 g, 4.8 mmol) into the hydrochloride salt and charge a flask with the solid salt. Dissolve the material in 200 mL methylene chloride and chill in ice. Add to this mixture boron tribromide (5.0 mL, 53.0 mmol) while swirling. Stir the reaction at room temperature for one hour and pour into a two phase system of saturated sodium bicarbonate and an organic layer consisting of a 3/1 mixture of chloroform/isopropanol. Shake to extract the product, separate the organic layer, dry over 3 Å molecular sieves and evaporate the solvent under vacuum. Purify on a silica gel column eluting with a 0-10% methanol/methylene chloride gradient to give 1.3 g (54%) of the title compound.

Example 127

5-[4-(2-Azepan-1-yl-ethoxy)-phenyl]-10-fluoro-5H-6-oxa-chrysen-2-ol

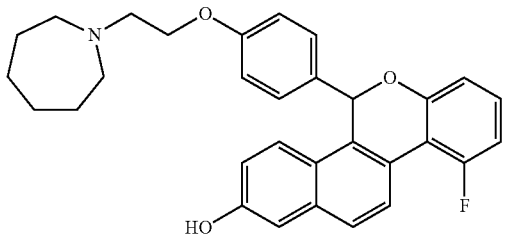

Dissolve [4-(2-azepan-1-yl-ethoxy)-phenyl]-[2-(2,6-difluoro-phenyl)-6-hydroxy-naphthalen-1-yl]-methanone (1.3 g, 2.6 mmol) in 125 mL dioxane and add 20 mL (20 mmol) of a 1.0 M solution of lithium triethylborohydride in THF. Stir at room temperature for one hour, then heat at 100° C. for three hours. Pour the reaction into a two phase system consisting of saturated sodium bicarbonate and an organic phase of a 3/1 mixture of chloroform/isopropanol. Extract in a reparatory funnel, separate the organic layer and dry over 3 Å molecular sieves. Evaporate to give 1.5 g of slightly impure product. Purify on a silica column eluting with 0-10% methanol/methylene chloride gradient to give 850 mg (68%) of racemic product: 1H-NMR (CDCl$_3$, 400 MHz) δ8.18 (d, J=8.4 Hz, 1H); 7.73 (d, J=8.8 Hz, 1H); 7.52 (d, J=9.2 Hz, 1H); 7.21 (d, J=2.4 Hz, 1H); 7.08-6.99 (m, 5H); 6.88 (s, 1H); 6.72-6.61 (m, 4H); 4.24-4.23 (m, 2H); 3.26-3.26 (m, 6H); 1.87-1.87 (m, 4H); 1.66-1.66 (m, 4H). The racemic mixture is purified using chiral chromatography (conditions F). The two isomers eluted with retention times of 7.9 and 9.0 minutes.

Example 128

[4-(2-Azepan-1-yl-ethoxy)-phenyl]-[6-methoxy-2-(2,3,5-trifluoro-phenyl)-naphthalen-1-yl]-methanone

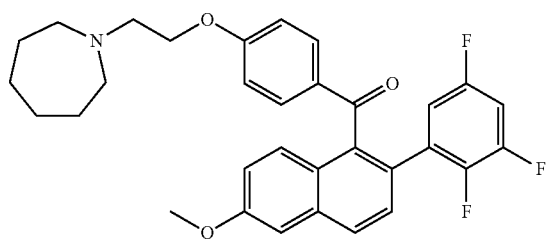

Dissolve trifluoromethanesulfonic acid 1-[4-(2-azepan-1-yl-ethoxy)-benzoyl]-6-methoxynaphthalen-2-yl ester (2.60 g, 6.53 mmol) in 200 mL acetonitrile and add to this bis(pinacoloato)diboron (1.5 g, 7.96 mmol), bis(tricyclohexylphosphine)palladium (0) (0.72 g, 1.50 mmol) and cesium fluoride (7.33 g, 67.0 mmol). Heat the reaction to 100° C. until LC/MS indicates all starting material is consumed. Add to this mixture 1-bromo-2,3,5-trifluorobenzene (2.00 g, 13.06 mmol) and another 720 mg of palladium catalyst and heat at 80° C. for 24 hours. Filter the reaction, concentrate filtrate and purify on a silica gel column eluting with a 0-10% methanol/methylene chloride gradient. The yield is 1.85 g (53%)

Example 129

[4-(2-azepan-1-yl-ethoxy)-phenyl]-[6-hydroxy-2-(2,3,5-trifluoro-phenyl)-naphthalen-1-yl]-methasone Dissolve [4-(2-azepan-1-yl-ethoxy)-phenyl]-[6-methoxy-2-(2,3,5-trifluorophenyl)-naphthalen-1-yl]-methanone (2.85 g, 5.34 mmol) in 50 mL methylene chloride and cool to 0° C. Add boron tribromide (3.0 mL, 31.7 mmol) and allow to come to room temperature. Pour into a two phase system of saturated sodium bicarbonate and 3/1 chloroform/isopropanol. Wash the organic layer with brine and dry over 3 Å molecular sieves. Concentrate to give 2.63 g (95%) of the title compound

Example 130

5-[4-(2-Azepan-1-yl-ethoxy)-phenyl]-7,9-difluoro-5H-6-oxa-chrysen-2-ol

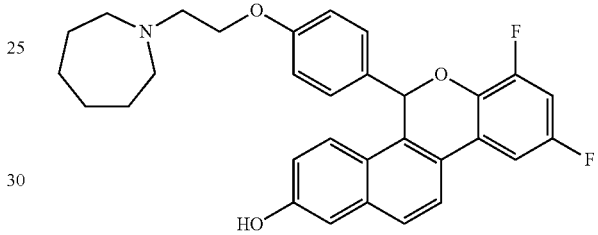

Dissolve [4-(2-azepan-1-yl-ethoxy)-phenyl]-[6-hydroxy-2-(2,3,5-trifluoro-phenyl)-naphthalen-1-yl]-methanone (2.63 g, 5.1 mmol) in 60 mL dioxane and add 10 mL of a 1.0 M solution of lithium triethylborohydride in THF. At the end of one hour, add another 10 mL of the lithium reagent mixture is added and gently warm the reaction. After a further one hour, add an additional 25 ml of lithium triethylborohydride and heat the reaction to reflux and hold for 8 hours. Cool the reaction and quench with water. Extract the water with methylene chloride, dry the organic layer with molecular sieves and concentrate. Purify on a silica gel column eluting with a 0-10% methanol/methylene chloride gradient.

Example 131

[4-(2-azepan-1-yl-ethoxy)-phenyl]-[6-methoxy-2-(2,4,6-trifluoro-phenyl)-naphthalen-1-yl]-methanone

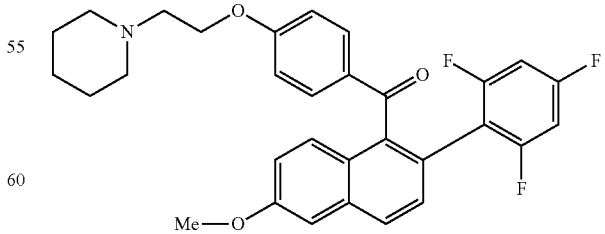

Dissolve trifluoromethanesulfonic acid 1-[4-(2-azepan-1-yl-ethoxy)-benzoyl]-6-methoxynaphthalen-2-yl ester (990 mg, 1.8 mmol), 2,4,6-trifluorophenylboronic acid (634 mg, 3.6 mmol), potassium phosphate (2.2 g, 10.8 mmol), tetrakis (triphenylphosphine)palladium (416 rag, 0.4 mmol) in dry DMF (25 mL) and heat at 100° C. for 3 hours. Purify reaction by SCX column. Additional purification is done by silica get chromatography using a 1-3% gradient of methanol in dichloromethane to yield 320 mg (35%) of the title compound: mass spectrum (ion spray) m/z=534 (M+H).

Example 132

[4-(2-azepan-1-yl-ethoxy)-phenyl]-[6-hydroxy-2-(2,4,6-trifluoro-phenyl)-naphthalen-1-yl]-methanone Dissolve [4-(2-azepan-1-yl-ethoxy)-phenyl]-[6-methoxy-2-(2,4,6-trifluoro-phenyl)-naphthalen-1-yl]-methanone (634 mg, 1.2 mmol) in dichloromethane (10 mL). Cool to 0° C., add HCl (2M in ether, 1.2 mL, 2.4 mmol) and stir at room temperature for 15 minutes. Concentrate in vacuo. Redissolve the salt in dichloromethane (10 mL) and cool to 0° C. Add boron tribromide (949 mg, 3.6 mmol) dropwise and bring to room temperature. Stir reaction for 1.5 hours and pour reaction mixture onto ice, saturated sodium bicarbonate (20 mL) and methanol (20 mL). Extract with dichloromethane, combine extracts and wash with water and saturated sodium bicarbonate. Dry with sodium sulfate, filter, and concentrate in vacuo. Purify by silica gel chromatography using a 1-3% gradient of methanol in dichloromethane to yield 350 mg (57%) of the title compound: mass spectrum (ion spray) m/z=520 (M+H).

Example 133

5-{[4-(2-azepan-1-yl-ethoxy)-phenyl]-hydroxy-methyl}-6-(2,4,6-trifluoro-phenyl)-naphthalen-2-ol Charge a flask with 1M borane in THF (4 mL) and (R)-(+) α,α-diphenylprolinol (26 mg, 0.1 mmol). Dissolve [4-(2-azepan-1-yl-ethoxy)-phenyl]-[6-hydroxy-2-(2,4,6-trifluoro-phenyl)-naphthalen-1-yl]-methanone (348 mg, 0.7 mmol) in THF (3 mL) and add to the catalyst solution via syringe pump over 1.5 hours at 45° C. Upon completion of the reaction add ethanolamine (0.8 mL, 13.4 mmol) and heat at 45° C. for 2 hours. Cool the reaction to room temperature and add brine (5 mL) and stir for 1 hour. Filter the reaction and separate layers. Dry the organic layer with sodium sulfate, filter and concentrate in vacuo. Purify by silica gel chromatography using a 1.5-5% gradient of methanol in dichloromethane to yield 306 mg (88%) of the title compound: mass spectrum (ion spray) m/z=522 (M+H).

Example 134

5-[4-(2-Azepan-1-yl-ethoxy)-phenyl]-8,10-difluoro-5H-6-oxa-chrysen-2-ol hydrochloride

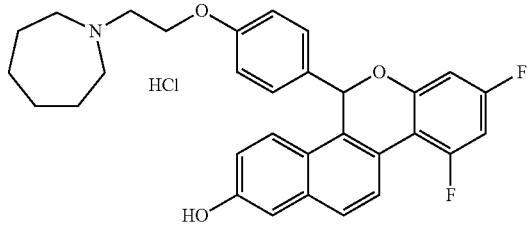

Dissolve 5-{[4-(2-azepan-1-yl-ethoxy)-phenyl]-hydroxy-methyl}-6-(2,4,6-trifluoro-phenyl)-naphthalen-2-ol (305 mg, 0.6 mmol) and potassium t-butoxide (197 mg, 1.8 mmol) in dry DMF (10 mL) and heat at 50° C. for 10 minutes. Cool reaction and pour onto ice/ethyl acetate. Separate organic layer and wash with 10% aqueous lithium chloride. Dry, filter and concentrate in vacuo. Purify by silica gel chromatography using a 1-6% gradient of methanol in dichloromethane to yield 285 mg (95%) of the free base of the title compound. Dissolve the free base (285 mg, 0.6 mmol) in dichloromethane (10 mL) and add HCl (2M in ether, 0.6 mL, 1.2 mmol) and stir for 10 minutes. Concentrate in vacuo to yield 234 mg (77%) of the title compound: mass spectrum (ion spray) m/z 502 (M−Cl).

Preparation 14

2-(2,4-Difluoro-phenyl)-6-methoxy-naphthalene-1-carbaldehyde

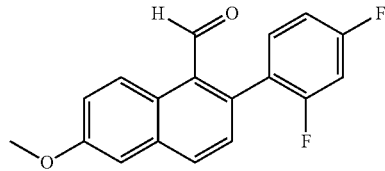

Cool a solution of 2-hydroxy-6-methoxy-naphthalene-1-carbaldehyde (18 g, 88.7 mmol, see Wrobel, et. al. *J. Med. Chem.* 1991, 34, 2504.) in dichloromethane (90 mL) to −78° C. Add pyridine (35.1 g, 443.6 mmol) and 4-dimethylaminopyridine (0.54 g, 4.4 mmol). Add trifluoromethanesulfonic anhydride (27.5 g, 97.6 mmol) and stir for 1 hour. Dilute with 2 M aqueous hydrochloric acid. Separate the organic layer and dry over magnesium sulfate. Filter, add silica gel, and concentrate in vacuo. Purify the residue by column chromatography using an eluent of 2:1 hexanes:dichloromethane. Isolate 9.0 g of trifluoromethanesulfonic acid 1-formyl-6-methoxy-naphthalen-2-yl ester (30%).

Combine trifluoromethanesulfonic acid 1-formyl-6-methoxy-naphthalen-2-yl ester (2.53 g, 7.6 mmol) with dichlorobis(triphenylphosphine)palladium (II) (0.53 g, 0.8 mmol), cesium fluoride (5.75 g, 37.8 mmol), and 2,4-difluorophenyl-boronic acid (2.39 g, 15.1 mmol) in acetonitrile (25 mL). Heat to reflux for 1 hour. Cool to room temperature, add DARCO, and filter. Concentrate in vacuo, dilute with dichloromethane and wash with saturated aqueous sodium carbonate. Dry the organic layer over magnesium sulfate, filter, add silica gel, and concentrate in vacuo. Purify the residue by column chromatography using an eluent of 1.5:1 hexanes:dichloromethane to give 1.4 g of the title compound (62%).

Example 135

[4-(8-Fluoro-2-methoxy-5H-6-oxa-chrysen-5-yl)-phenyl]-(2-piperidin-1-yl-ethyl)-carbamic acid tert-butyl ester

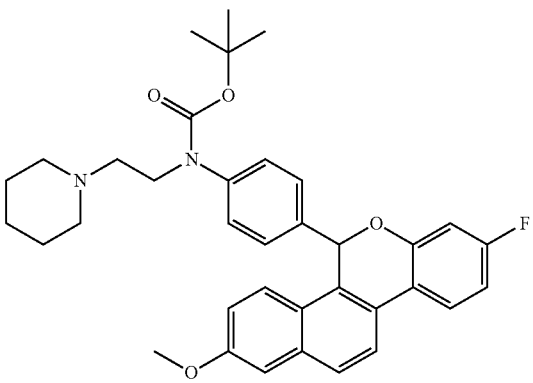

Dissolve (4-bromo-phenyl)-(2-piperidin-1-yl-ethyl)-carbamic acid tert-butyl ester in dry tetrahydrofuran (20 mL). Cool to −78° C. and add 1.6 M n-butyl lithium in hexanes (0.79 mL). After 30 minutes, add 2-(2,4-difluoro-phenyl)-6-methoxy-naphthalene-1-carbaldehyde (0.25 g, 0.839 mmol) and stir 45 minutes cold. Warm to room temperature over 1 hour. Reflux 2 hrs. Cool to room temperature and dilute with dichloromethane (20 mL) and saturated aqueous ammonium chloride (20 mL). Separate the organic layer and wash the aqueous layer twice with dichloromethane. Combine the organics and dry over magnesium sulfate. Filter and concentrate in vacuo. Purify the residue by column chromatography using a silica gel column eluting with a linear gradient beginning with dichloromethane and ending with 4:1 dichloromethane methanol to give 0.45 g (92%) of the title compound: mass spectrum (ion spray) m/z=583.3 (M+H).

Example 136

8-Fluoro-5-[4-(2-piperidin-1-yl-ethylamino)-phenyl]-5H-6-oxa-chrysen-2-ol dihydrochloride Dissolve [4-(8-fluoro-2-methoxy-5H-6-oxa-chrysen-5-yl)-phenyl]-(2-piperidin-1-yl-ethyl)-carbamic acid tert-butyl ester in dichloromethane (25 mL). Add a 1.0 M solution of hydrogen chloride in ether (5 mL). Concentrate in vacuo. Redissolve in dichloromethane (20 mL). Cool to 0° C. Add boron tribromide (0.238 mL, 2.52 mmol). After 3 hrs dilute with saturated aqueous sodium bicarbonate (10 mL) and methanol (10 mL). Separate the organic layer and wash the aqueous layer twice with dichloromethane. Combine the organics and dry over magnesium sulfate. Filter and concentrate in vacuo. Purify the residue by column chromatography using a silica gel column eluting with a linear gradient beginning with dichloromethane and ending with 4:1 dichloromethane:methanol. Combine the product containing fractions and add 1.0 M hydrogen chloride in ether (2 mL). Concentrate in vacuo to isolate the title compound: mass spectrum (ion spray) m/z=469.2 (M+H). Purify the mixture by chiral chromatography (conditions A). The two isomers eluted with retention times of 4.02 and 5.46 minutes.

Example 137

7,9-Difluoro-6-oxo-5-[4-(2-piperidin-1-yl-ethoxy)-phenyl]-5,6-dihydro-6λ4-thia-chrysen-2-ol hydrochloride Dissolve 7,9-difluoro-5-[4-(2-piperidin-1-yl-ethoxy)-phenyl]-5H-6-thia-chrysen-2-ol (130 mg, 0.26 mmol) in acetic acid (3 mL). Add sodium perborate (29 mg, 0.29 mmol) and stir at room temperature for 3 days. Slowly pour the reaction into saturated aqueous sodium bicarbonate and extract with 20% methanol/methylene chloride. Dry the organic layer with sodium sulfate, filter and concentrate. Purify on silica gel (5% to 10% methanol in methylene chloride) to yield 28 mg of impure product. The material is dissolved in methylene chloride and 2M HCl in ether (0.2 mL) is added and the solvent removed in vacuo to yield 28 mg (20%) of the title compound: mass spectrum (ion spray) m/z=542.2 (M−Cl+Na).

Example 138

[2-(4-Fluoro-2-methylsulfanyl-phenyl)-6-methoxy-naphthalen-1-yl]-[4-(2-piperidin-1-yl-ethoxy)-phenyl]-methanone

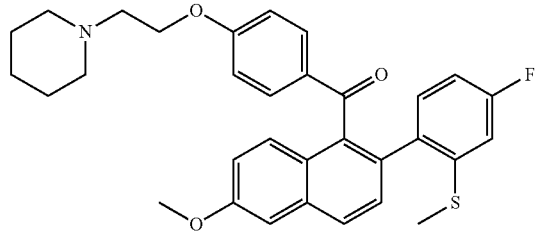

Charge a flask with trifluoromethanesulfonic acid 6-methoxy-1-[4-(2-piperidin-1-yl-ethoxy)-benzoyl]-naphthalen-2-yl ester (580 mg, 1.1 mmol), 2-methylsulfanyl-4-fluoro-benzene boronic acid (400 mg, 2.2 mmol) and cesium fluoride (830 mg, 5.4 mmol) and flush with nitrogen. In a separate flask, add palladium acetate (24 mg, 0.11 mmol) and tricyclohexylphosphine (62 mg, 0.22 mmol) and suspend in dry degassed acetonitrile (10 mL). Socinate under nitrogen for 10 minutes and add the catalyst solution to the solids and plunge into an 80° C. oil bath for 30 minutes. Cool to room temperature, filter through celite and concentrate in vacuo. Purify the residue by silica gel chromatography (0 to 3% methanol in methylene chloride) to yield 476 mg (83%) of the title compound: mass spectrum (ion spray) m/z=530.2 (M+H).

Example 139

1-{2-[4-(8-Fluoro-2-methoxy-5H-6-thia-chrysen-5-yl)-phenoxy]-ethyl}-piperidine

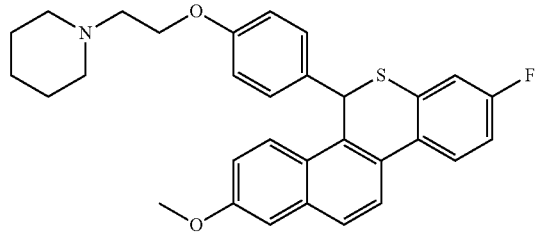

Dissolve [2-(4-fluoro-2-methylsulfanyl-phenyl)-6-methoxy-naphthalen-1-yl]-[4-(2-piperidin-1-yl-ethoxy)-phenyl]-methanone (1.2 g, 2.2 mmol) in dry THF (20 mL). Add lithium aluminum hydride (1M in THF, 2.3 mL, 2.3 mmol) dropwise. After 10 minutes slowly pour the black solution into saturated aqueous ammonium chloride and extract with methylene chloride twice. Dry the combined organic layers with sodium sulfate, filter and concentrate to yield a 2:1 mixture of rotational diastereomers. Dissolve the crude foam in dry THF (15 mL). Add diisopropylethylamine (2.5 mL, 14.4 mmol) and methanesulfonyl chloride (0.45 mL, 5.8 mmol) and heat to reflux under nitrogen. Add more methanesulfonyl chloride (0.45 mL, 5.8 mmol) after 2 hours to drive the reaction to completion. Pour the reaction into saturated aqueous sodium bicarbonate and extract twice with methylene chloride. Dry the combined organic layers with sodium sulfate, filter and concentrate. Purify the residue on silica gel (0% to 3% methanol in methylene chloride) to yield 440 mg (44%) of the title compound: mass spectrum (ion spray) m/z=500.3 (M+H).

Alternative Preparation of the Compound of Example 100

8-Fluoro-5-[4-(2-piperidin-1-yl-ethoxy)-phenyl]-5H-6-thia-chrysen-2-ol hydrochloride Dissolve 1-{2-[4-(8-fluoro-2-methoxy-5H-6-thia-chrysen-5-yl)-phenoxy]-ethyl}-piperidine (330 mg, 0.67 mmol) in methylene chloride (6.0 mL) and add 2M HCl in ether (0.67 mL). Concentrate in vacuo and dissolve in dry methylene chloride (6.0 mL). Add 2-methyl-2-butene (0.71 mL, 6.7 mmol) and cool to 0° C. under nitrogen. Add boron tribromide (0.25 mL, 2.7 mmol) slowly and stir at 0° C. for 20 minutes. Pour the reaction into saturated aqueous sodium bicarbonate and extract with methylene chloride/methanol (4:1). Dry organic layer with sodium sulfate, filter and concentrate in vacuo. Purify the resultant oil over silica gel (0% to 3% methanol in methylene chloride). Dissolve the resultant oil in methylene chloride (3 mL) and add 2M HCl in ether (0.5 mL). Remove the solvent in vacuo and place in a 50° C. vacuum oven overnight to yield 225 mg (65%) of the title compound: mass spectrum (ion spray) m/z=486.3 (M−Cl).

Preparation 15

(2-Bromo-5-fluoro-phenyl)-carbamic acid tert-butyl ester

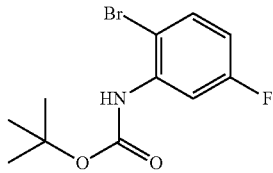

Place 2-bromo-5-fluoroaniline (2.50 g, 13.16 mmol) and dichloromethane (50 mL) in a round bottom flask. Add sodium hydride (60% dispersion in mineral oil) (0.58 g, 14.47 mmol) and stir this suspension at ambient temperature for 20 minutes. Now add di-t-butyl dicarbonate (3.02 g, 13.82 mmol) and stir for 30 minutes at ambient temperature followed by 2 hours at reflux. Cool this solution to ambient temperature and add more sodium hydride (60% dispersion in mineral oil) (0.58 g, 14.47 mmol) and di-t-butyl dicarbonate (0.30 g, 1.38 mmol). Heat this mixture at reflux overnight. Cool the reaction to ambient temperature and quench with H₂O and saturated aqueous ammonium chloride. Extract the resulting mixture into ethyl acetate. Combine the extracts and wash with saturated aqueous sodium bicarbonate, H₂O and brine; then dry (sodium sulfate) and concentrate in vacuo. Purify the resulting oil by flash chromatography (silica gel; 5% Et₃O/hexanes) to provide the desired product, 3.61 g (95%).

Example 140

(2-{6-Benzyloxy-1-[4-(2-piperidin-1-yl-ethoxy)-benzoyl]-naphthalen-2-yl}-5-fluoro-phenyl)-carbamic acid tert-butyl ester

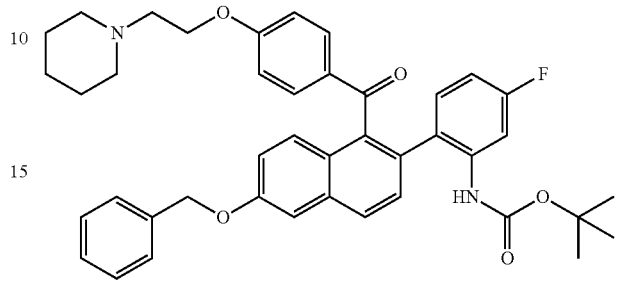

Add (2-bromo-5-fluoro-phenyl)-carbamic acid tert-butyl ester (1.06 g, 3.67 mmol), bis(pinacolato)diboron (1.03 g, 4.04 mmol), palladium(II) acetate (0.062 g, 0.28 mmol), tricyclohexylphosphine (0.103 g, 0.37 mmol) and acetonitrile (40 mL) to a round bottom flask. Stir at ambient temperature for approximately 5 minutes to dissolve most of the reagents. Add cesium fluoride (2.10 g, 13.82 mmol), place the flask in a 90° C. oil bath, and stir for 30-45 minutes. Remove the oil bath and allow the reaction mixture to cool to ambient temperature. To this mixture, add trifluoromethanesulfonic acid 6-benzyloxy-1-[4-(2-piperidin-1-yl-ethoxy)-benzoyl]-naphthalen-2-yl ester (0.75 g, 1.22 mmol), palladium(II) acetate (0.062 g, 0.28 mmol), tricyclohexylphosphine (0.103 g, 0.37 mmol) and place the reaction in a 90° C. oil bath. Stir the reaction for 4 hours at 90° C. Cool the reaction to ambient temperature, filter it through a pad of Celite and rinse the pad with ample, hot ethyl acetate. Wash the filtrate with 50% aqueous sodium carbonate, saturated aqueous ammonium chloride, H₂O and brine; then dry (sodium sulfate) and evaporate it in vacuo. Load the resulting material onto an SCX column. Wash with dichloromethane, 50% dichloro-methane/methanol, elute with ammonia solution (2N NH₃ in methanol) and remove solvent under vacuum. Purify the resulting residue by flash chromatography (silica gel; 1%-5% methanol gradient in dichloromethane: followed by a second chromatography 2% of 2N NH₃ in methanol/25% THF/hexanes: followed by purification on a Chromatotron; 2% MeOH/dichloromethane) to provide 0.300 g (36%) of the title compound: mass spectrum (ion spray) m/z=675 (M+H).

Example 141

(5-Fluoro-2-{6-hydroxy-1-[4-(2-piperidin-1-yl-ethoxy)-benzoyl]-naphthalen-2-yl}-phenyl)-carbamic acid tert-butyl ester To a round bottom flask add (2-{6-benzyloxy-1-[4-(2-piperidin-1-yl-ethoxy)-benzoyl]-naphthalen-2-yl}-5-fluoro-phenyl)-carbamic acid tert-butyl ester (0.075 g, 0.11 mmol), ammonium formate (0.056 g, 0.89 mmol), methanol (5 mL) and a slurry of 10% Pd/C (0.012 g, ~15% by weight) and ethanol (2 mL). Heat the mixture, with stirring, at reflux for 30 minutes. Cool the reaction to ambient temperature and filter it through a pad of Celite, then rinse the Celite with hot methanol. Evaporate the filtrate in vacuo and purify the resulting residue by radial chromatography over silica (4-9% MeOH gradient in CH$_2$Cl$_2$) to provide the product 61 mg (94%): mass spectrum (ion spray) m/z=585 (M+H).

Example 142

8-Fluoro-5-[4-(2-piperidin-1-yl-ethoxy)-phenyl]-5,6-dihydro-benzo[i]phenanthridin-2-ol

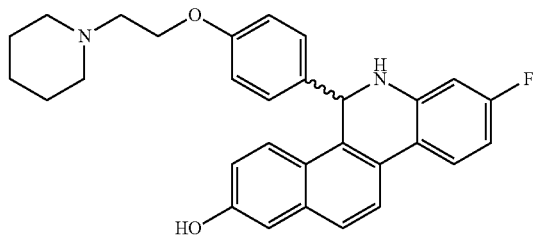

To a round bottom flask add (5-fluoro-2-{6-hydroxy-1-[4-(2-piperidin-1-yl-ethoxy)-benzoyl]-naphthalen-2-yl}-phenyl)-carbamic acid tert-butyl ester (0.060 g, 0.103 mmol), dichloromethane (1.25 mL), anisole (0.15 mL, 1.39 mmol) and trifluoroacetic acid (0.25 mL). Stir the reaction for 1.5 hour at ambient temperature. Add trifluoroacetic acid (2.0 mL) and sodium borohydride (0.024 g, 0.62 mmol) and stir the reaction at ambient temperature for 1.5 hours. Add more sodium borohydride (0.024 g, 0.62 mmol) and stir the reaction at ambient temperature an additional 2 hours. After aqueous work-up and purification LC/MS showed significant amounts of the (M-2) intermediate, so take this material up in acetic acid (3.0 mL) and to it add sodium cyanoborohydride (0.032 g, 0.51 mmol). Stir this mixture for 1.5 hours at ambient temperature. Add more sodium cyanoborohydride (0.032 g, 0.51 mmol) and stir an additional 1.5 hours at ambient temperature. Quench the reaction with saturated aqueous sodium bicarbonate. Extract the resulting aqueous mixture into ethyl acetate. Wash the combined extracts with saturated aqueous sodium bicarbonate, H$_2$O and brine; then dry (sodium sulfate) and evaporate the filtrate in vacuo. Purify the resulting residue by radial chromatography over silica (5%-10% methanol gradient in dichloromethane) to provide 17 mg (35%) of the title compound: mass spectrum (ion spray) m/z=469 (M+H).

Preparation 16

(2-Bromo-5-fluoro-phenyl)-methyl-carbamic acid tert-butyl ester

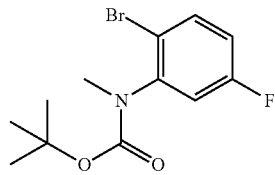

Place (2-bromo-5-fluoro-phenyl)-carbamic acid tert-butyl ester (2.00 g, 6.90 mmol) and dimethylformamide (40 mL) in a round bottom flask. Cool the solution to 0° C., add sodium hydride (60% dispersion in mineral oil) (0.303 g, 7.59 mmol), remove the ice bath and stir this suspension for 25 minutes allowing it to warm slowly towards ambient temperature. Cool the resulting mixture to 0° C. once again, and add iodomethane (0.56 mL, 8.96 mmol). Stir the resulting mixture overnight, allowing it to warm to ambient temperature. Quench the reaction with brine and extract the resulting mixture into ethyl acetate. Combine the extracts and wash with brine; then dry (sodium sulfate) and concentrate in vacuo. Purify the resulting material by flash chromatography (silica gel; 35%-50% dichloromethane gradient in hexanes) to provide the desired product.

Example 143

(2-{6-Benzyloxy-1-[4-(2-piperidin-1-yl-ethoxy)-benzoyl]-naphthalen-2-yl}-5-fluoro-phenyl)-methyl-carbamic acid tert-butyl ester

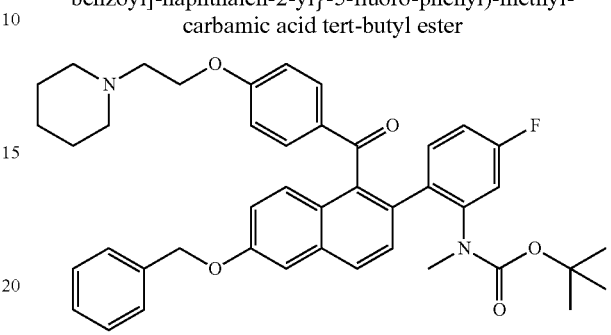

Add trifluoromethanesulfonic acid 6-benzyloxy-1-[4-(2-piperidin-1-yl-ethoxy)-benzoyl]-naphthalen-2-yl ester (0.73 g, 1.18 mmol), bis(neopentyl glycolato)diboron (0.29 g, 1.30 mmol), bis(tricyclohexylphosphine)palladium(0) (0.16 g, 0.24 mmol) and acetonitrile (14 mL) to a round bottom flask. Stir at ambient temperature for approximately 5 minutes to dissolve most of the reagents. Add cesium fluoride (1.62 g, 10.64 mmol), place the flask in a 90° C. oil bath, and stir under nitrogen for 2-3 minutes. Now add a solution of (2-bromo-5-fluoro-phenyl)-methyl-carbamic acid text-butyl ester (0.86 g, 2.84 mmol) and acetonitrile (3 mL). Continue stirring the reaction for 2 hours at 90° C. Cool the reaction to ambient temperature and then filter it through a pad of Celite. Rinse the pad with ample, hot ethyl acetate. Wash the filtrate in a reparatory funnel with 50% aqueous sodium carbonate, saturated aqueous ammonium chloride, H$_2$O and brine; then dry (sodium sulfate) and evaporate it in vacuo. Purify the resulting residue by flash chromatography (silica gel; 2% methanol/dichloromethane) to provide 0.320 g (39%) of the title compound: mass spectrum (ion spray) m/z=689 (M+H).

Example 144

2-Benzyloxy-8-fluoro-6-methyl-5-[4-(2-piperidin-1-yl-ethoxy)-phenyl]-5,6-dihydro-benzo[i]phenanthridine

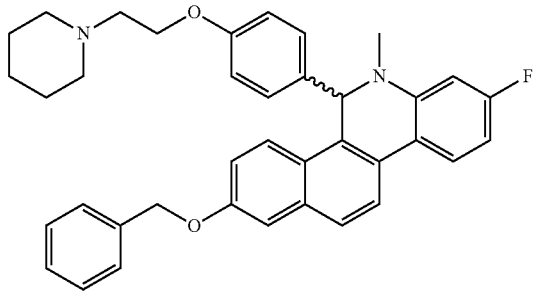

To a round bottom flask add (2-{6-benzyloxy-1-[4-(2-piperidin-1-yl-ethoxy)-benzoyl]-naphthalen-2-yl}-5-fluoro-phenyl)-methyl-carbamic acid tert-butyl ester (0.070 g, 0.10 mmol), dichloromethane (1.25 mL), anisole (0.012 mL, 0.11 mmol) and trifluoroacetic acid (0.25 mL). Stir the reaction for 1 hour at ambient temperature. Add trifluoroacetic acid (1.0 mL) and sodium cyanoborohydride (0.064 g, 1.02 mmol) and stir the reaction at ambient temperature for 1 hour. Add more sodium cyanoborohydride (0.064 g, 1.02 mmol) and trifluoroacetic acid (1.0 mL) and stir the reaction at 50° C. for 1 hour. Quench the reaction with saturated aqueous sodium bicarbonate. Extract the resulting aqueous mixture into ethyl acetate. Wash the combined extracts with saturated aqueous sodium bicarbonate, $H_2O$ and brine; then dry (sodium sulfate) and evaporate the filtrate in vacuo. Purify the resulting residue by radial chromatography over silica (2%-6% methanol gradient in dichloromethane) to provide the product, 32 mg (55%): mass spectrum (ion spray) m/z=573 (M+H).

Example 145

8-Fluoro-6-methyl-5-[4-(2-piperidin-1-yl-ethoxy)-phenyl]-5,6-dihydro-benzo[i]phenanthridin-2-ol To a round bottom flask add 2-benzyloxy-8-fluoro-6-methyl-5-[4-(2-piperidin-1-yl-ethoxy)-phenyl]-5,6-dihydro-benzo[i]phenanthridine (0.030 g, 0.052 mmol), ammonium formate (0.026 g, 0.42 mmol), methanol (5 mL) and a slurry of 10% Pd/C (0.005 g, ~15% by weight) and ethanol (2 mL). Heat the mixture, with stirring, at reflux for 30 minutes. Cool the reaction to ambient temperature and filter it through a pad of Celite, then rinse the Celite with hot methanol. Evaporate the filtrate in vacuo and purify the resulting residue by radial chromatography over silica (5-10% MeOH gradient in $CH_2Cl_2$) to provide the product 20 mg (80%); mass spectrum (ion spray) m/z=483 (M+H).

Example 146

[2-(4,5-Difluoro-2-methoxy-phenyl)-6-methoxy-naphthalen-1-yl]-[4-(2-piperidin-1-yl-ethoxy)-phenyl]-methanone

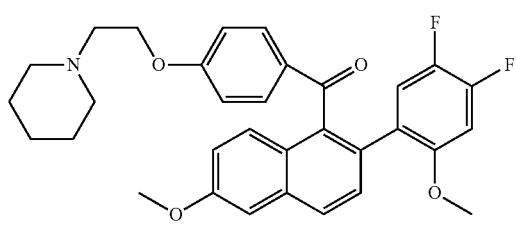

Add trifluoromethanesulfonic acid 6-methoxy-1-[4-(2-piperidin-1-yl-ethoxy)-benzoyl]-naphthalen-2-yl ester (2.3 gm, 4.2 mmoles), bis(pinacolato)diboron (1.3 gm, 5.1 mmoles), palladium II acetate (97 mg, 0.4 mmoles), triphenylphosphine (222 mg, 0.84 mmoles) and cesium fluoride (2.1 gm, 14.1 mmoles) in a 250 ml round bottom flask under nitrogen and add 100 ml of anhydrous acetonitrile. Stir and heat to reflux for 2 hours. Allow the mixture to cool and to this mixture add 2-bromo-4,5-difluoroanisole (2.8 gm, 12.5 mmoles), palladium II acetate (96 mg, 0.43 mmoles) triphenylphosphine (222 mg, 0.84 moles) and cesium fluoride (1.8 gm, 12.2 mmoles). Reflux the mixture for 18 hours and filter through Celite. Evaporate the solvent and pass through an SCX column eluting the product with 2N ammonia/methanol. The product is purified on a silica column eluting with a gradient of 25% THF/hexane to 5% 2N ammonia/methanol in 25% THF/Hexane. LC/MS gives a peak with the proper mass.

Preparation 17

8,9-Difluoro-5-methoxy-5-[4-(2-piperidin-1-yl-ethoxy)-phenyl]-5H-6-oxa-chrysen-2-ol

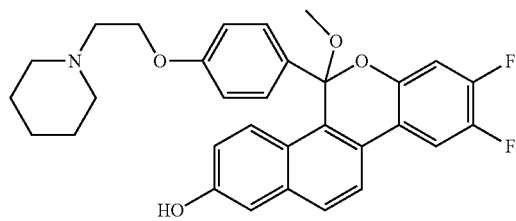

Convert [2-(4,5-Difluoro-2-methoxy-phenyl)-6-methoxy-naphthalen-1-yl]-[4-(2-piperidin-1-yl-ethoxy)-phenyl]-methanone to the HCl salt and add 1.6 grams of said salt to a 250 ml round bottom flask. Add 100 ml methylene chloride and place under nitrogen. Cool the solution to 0 degrees Celsius and add 3.0 ml of boron tribromide. Allow the reaction to warm to room temperature and stir for one hour. Quench the reaction with methanol and wash with saturated sodium bicarbonate solution. Extract the water with methylene chloride, combine the organic portions and remove the solvent. Purify the residue on an SCX column, eluting the product with 2N ammonia/methanol. Purify the compound further using a silica column eluting with a gradient of 0-5% 2 M ammonia/methanol in methylene chloride (78%).

Example 147

8,9-Difluoro-5-[4-(2-piperidin-1-yl-ethoxy)-phenyl]-5H-6-oxa-chrysen-2-ol

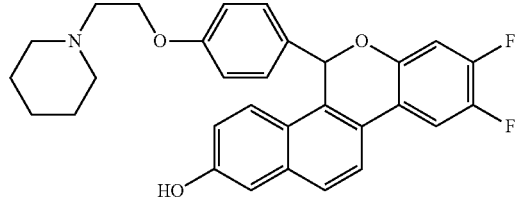

Dissolve 8,9-Difluoro-5-methoxy-5-[4-(2-piperidin-1-yl-ethoxy)-phenyl]-5H-6-oxa-chrysen-2-ol (1.1 gm, 21. mmoles) in 30 ml of methylene chloride and add 2 ml of triethylamine and 2 ml of trifluoroacetic acid. Stir at room temperature for 1 hour, neutralize with sodium bicarbonate solution and separate the organic layer. Wash the water layer with methylene chloride and combine the organic layers. Dry the liquid over sodium sulfate and remove the solvent. Purify as described in Preparation 17 to obtain an 18% yield of the racemic. Obtain the individual enantiomers by chiral chromatography using a Chiralpak AD column eluting with ethanol containing 0.2% dimethylethylamine and monitoring at 225 nm.

Example 148

5-[4-(2-Diethylamino-ethoxy)-phenyl]-8,9-difluoro-5H-6-oxa-chrysen-2-ol hydrochloride Dissolve 8,9-Difluoro-5-methoxy-5-[4-(2-piperidin-1-yl-ethoxy)-phenyl]-5H-6-oxa-chrysen-2-ol (1.72 g, 3.32 mmol) in chloroform (100 mL) and add triethylsilane (1.0 mL, 6.26 mmol) and trifluoroacetic acid (2.5 mL, 32.45 mmol). Heat the reaction to reflux for four hours. After cooling to room temperature, pour reaction into ice and 1.0 M sodium hydroxide (200 mL). Add saturated sodium bicarbonate solution until basic. Separate the organic and extract the aqueous with 25% isopropanol/chloroform (3×200 mL). Combine the organics, dry with sodium sulfate, and remove the solvent. Isolate the product by flash chromatography on silica gel [0-5% (2M ammonia/methanol)/(25% THF/hexanes)]. Wash the resulting solid with ether and collect by filtration. Dissolve solid in 1:1 acetonitrile/1.0M HCl (4 mL), freeze at −78° C., and lyophilize for 16 hours to afford 659.0 mg (37.9%) of the title compound: LCMS (5 min): 3.04 min, 488 (M+H).

Preparation 18

6-Boronic acid-5-[4-(2-piperidin-1-yl-ethoxy)-phenoxy]-naphthalen-2-ol hydrochloride salt

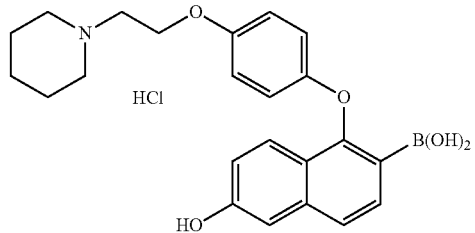

Charge a flask with trifluoro-methanesulfonic acid 6-methoxy-1-[4-(2-piperidin-1-yl-ethoxy)-phenoxy]-naphthalen-2-yl ester (10.0 g, 19.0 mmol) and dissolve in methylene chloride (100 mL). Add 2M HCl in ether (19 mL, 38 mmol) and remove solvent in vacuo. Redissolve in dry methylene chloride (200 mL) and cool to 0° C. under nitrogen. Add BBr$_3$ (9.0 mL, 95 mmol) slowly, and stir at 0° C. for 30 minutes. Pour reaction slowly into saturated aqueous sodium bicarbonate and extract with methylene chloride. Dry over sodium sulfate, filter and concentrate in vacuo. Dissolve crude material in methylene chloride (200 mL) and add N,N-diisopropylethylamine (16.5 mL, 95 mmol) and 4-dimethylaminopyridine (120 mg, 1.9 mmol) and stir at room temperature. Add acetic anhydride (3.6 mL, 38 mmol). Stir for 20 minutes and pour into saturated aqueous sodium bicarbonate. Extract with methylene chloride. Wash the organic layer with water, dry over sodium sulfate, filter and concentrate in vacuo to yield 10.5 g (100%) of acetic acid 5-[4-(2-piperidin-1-yl-ethoxy)-phenoxy]-6-trifluoromethanesulfonyloxy-naphthalen-2-yl ester.

Degas dry acetonitrile (100 mL) with nitrogen bubble for 10 minutes. Add palladium acetate (450 mg, 1.8 mmol), tricyclohexylphosphine (850 mg, 2.7 mmol) and cesium fluoride (11.6 g, 76 mmol) and stir for 20 minutes with degas. Add acetic acid 5-[4-(2-piperidin-1-yl-ethoxy)-phenoxy]-6-trifluoromethanesulfonyloxy-naphthalen-2-yl ester (5.6 g, 10.1 mmol) and stir under nitrogen for 3 minutes. Add bis(neopentyl glycolato)diboron (13.7 g, 60.6 mmol) and plunge into a 60° C. oil bath and stirred for 1 hr. Cool to room temperature and filter through celite and concentrate in vacuo. Dissolve the resulting solid in ether (100 mL) and add diethanolamine (1.0 g, 10.1 mmol) and stir for 1 hr. Filter the resulting white precipitate. Suspend the precipitate in water and add 1N HCl followed by methanol to dissolve the suspension. Stir for 36 hr. Extract with methylene chloride (×3), dry over sodium sulfate, filter and concentrate in vacuo to yield 2.7 g (66%) of the title compound. Mass spectrum (ion spray): m/z=408.2 (M+1−HCl).

Example 149

5-[4-(2-Piperidin-1-yl-ethoxy)-phenoxy]-6-(2,3,4-trifluoro-phenyl)-naphthalen-2-ol trifluoroacetate salt

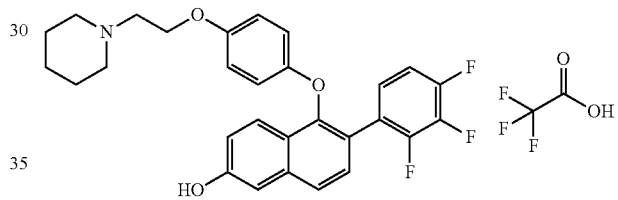

Add 6-boronic acid-5-[4-(2-piperidin-1-yl-ethoxy)-phenoxy]-naphthalen-2-ol hydrochloride salt (20 mg, 0.05 mmol) and freshly distilled dimethoxyethane and 2M sodium carbonate (9:1, 3 mL total volume) to a Quest210 under nitrogen. Add 2,3,4-trifluoro-bromobenzene (3 eq) followed by trans-dichlorobis(tri-o-tolylphosphine)palladium (10 mg, 0.01 mmol) and heat to 70° C. overnight under nitrogen. Cool reaction to room temperature and filter into tubes containing ~400 mg TsOH-MP and agitate for 3 hours. Solvent filtered off and washed with DME. Add 3N ammonia in methanol and filter. Wash resin three times with 3N ammonia in methanol. Concentrate in vacuo and purify by reverse phase HPLC.

Preparative HPLC's may be obtained, e.g., on a Mass Guided Waters Preparative System using a 20×100 mm C18 Symmetry column. The eluent is a binary system of bottle and bottle A (0.1% trifluoroacetic acid in water) B (0.1% trifluoroacetic acid in acetonitrile). The standard method is a gradient of 10-95% B. MS (IS+) m/e 494 (M+1−TFA).

Formulation (Pharmaceutical Composition)

Because the free base form of a compound of formula I contains a basic moiety (i.e., amino), said compound may be formulated as a pharmaceutical acid addition salt, e.g., as the hydrochloride salt or as a salt described in "Handbook of Pharmaceutical Salts: Properties, Selection and Use", Weinheim, N.Y.: VHCA; Wiley-VCH, 2002.

The present pharmaceutical compositions are prepared by known procedures using well-known and readily available ingredients. In making the formulations of the present invention, the active ingredient (a formula I compound) will usually be mixed with a carrier, or diluted by a carrier, or enclosed within a carrier which may be in the form of a capsule, sachet, paper or other container. When the carrier serves as a diluent, it may be a solid, semisolid or liquid material that acts as a vehicle, excipient or medium for the active ingredient.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents.

Biological Assays

Ishikawa Cell Proliferation Assay: This assay measures cell proliferation (using an alkaline phosphatase readout) in both an agonist mode in the presence of a compound of the present invention alone, and in an antagonist mode in which the ability of a compound of the present invention to block estradiol stimulation of growth is measured.

Ishikawa human endometrial tumor cells are maintained in MEM (minimum essential medium, with Earle's salts and L-Glutamine, Gibco BRL, Gaithersburg, Md.), supplemented with 10% fetal bovine serum (FBS) (V/V), (Gibco BRL). One day prior to assay, growth media is changed to assay medium, DMEM/F-12 (3:1) (Dulbecco's Modified Eagle Medium: Nutrient Mixture F-12, 3:1 Mixture, phenol red-free, Gibco BRL) supplemented with 5% dextran coated charcoal stripped fetal bovine serum (DCC-PBS) (Hyclone, Logan, Utah), L-Glutamine (2 mM), MEM sodium pyruvate (1 mM), HEPES (N-[2-hydroxyethyl]piperazine-N'-[2-ethanesulfonic acid] 2 mM) all from Gibco BRL). After an overnight incubation, Ishikawa cells are rinsed with Dulbecco's Phosphate Buffered Saline (1×) (D-PBS) without $Ca^{+2}$ and $Mg^{+2}$ (Gibco BRL), and trypsinized by a 3 minute incubation with 0.25% Trypsin/EDTA, phenol red-free (Gibco BRL). Cells are resuspended in assay medium and adjusted to 250,000 cells/mL. Approximately 25,000 cells in a 100 ul media are added to flat-bottom 96 wells microculture plates (Costar 3596) and incubated at 37° C. in a 5% $CO_2$ humidified incubator for 24 hours. The next day, serial dilutions of compounds are prepared in assay medium (at 6 times the final concentration in the assay). The assay is run in dual mode, agonist and antagonist modes.

For the agonist mode, plates receive 25 μl/well of assay medium followed by 25 μl/well of a diluted compound of the present invention (at 6× the final concentrations). For the antagonist mode, plates receive 25 μl/well of 6 nM $E_2$ (β-Estradiol, Sigma, St. Louis, Mo.) followed by 25 μl/well of a diluted compound of the present invention (at 6× the final concentrations). After an additional 48-hour incubation at 37° C. in a 5% $CO_2$ humidified incubator, media is aspirated from wells and 100 μl fresh assay medium is added to each microculture. Serial dilutions of compounds are prepared and added to the cells as described above. After an additional 72 hour incubation at 37° C. in a 5% $CO_2$ humidified incubator, the assay is quenched by removing media and rinsing plates twice in Dulbecco's Phosphate Buffered Saline (1×) (D-PBS) (Gibco BRL). The plates are dried for 5 minutes and frozen at −70° C. for at least 1 hour. The plates are then removed from the freezer and allowed to thaw at room temperature. To each well, 100 μl of 1-Step™ PNPP (Pierce Chemical Company, Rockford, Ill.) is added. After a 20-minute incubation, plates are read on a spectrophotometer at 405 nm.

The data is fitted to a linear interpolation to derive EC50 (for agonist mode) or IC50 (for antagonist mode) values. For the antagonist mode, a % efficacy for each compound is calculated versus E2 (1 nM) alone. For the agonist mode, a % efficacy for each compound is calculated versus the response to tamoxifen.

3-Day Rat Uterus Antagonist Assay: This model for uterine antagonism utilizes immature (3 week old) female rats that are highly sensitive to estrogenic stimulation of the uterus given that their circulating estrogen levels are prepubertal. The uteri from immature rats are fully responsive to exogenous estrogen, yet are quiescent in the absence of exogenous estrogen. Administration of exogenous estrogen to immature rats produces a reliable elevation of uterine weight, which can be used to study uterine antagonist effects. The rats are treated with both estradiol and 4 different concentrations of a compound of the present invention for 3 days and then uterine wet weights are measured.

Nineteen to twenty-one day old (or 45-50 g) female rats are orally treated with E2 (0.1 mg/kg, a maximal stimulatory estrogenic stimulus for reliably increasing uterine weight) and 10, 1.0, 0.1 and 0.01 mg/kg test compound for 3 days, 6 rats per group. Test compounds are dissolved in 20% β-hydroxycyclodextrin and administered by oral gavage in a volume of 0.2 mL daily (15 min, prior to the ethynyl estradiol gavage). A vehicle control, E2 alone and E2+raloxifene are also done as controls. The animals are fasted overnight following the final dose. On the following morning, the animals are weighed, then euthanized (by carbon dioxide asphyxiation) and the uteri rapidly collected (via a mid-line ventral incision) and weighed.

Uterine weight/body weight ratios (UWR) are calculated for each animal. The percent inhibition of the estrogen-induced response is then calculated by the following formula: percent inhibition=100×($UWR_{estrogen}$−$UWR_{test\ compound}$/$UWR_{estrogen}$−$UWR_{control}$). $ED_{50}$ values are derived from a semi-log regression analysis of the linear aspect of the dose response curve. Both the UWR data and the percent inhibition data are statistically analyzed by one way analysis of variance (ANOVA) with post-hoc testing by Fisher's PLSD when indicated by a $p \leq 0.05$. Statistical analyses are performed using the Statview® 4.0 software package.

Morphine withdrawal, rat hot flash model: Simpkins et al. (1983) first published morphine withdrawal in the rat as a putative model for hot flashes, based on observations highlighting the similarity of symptoms of gonadal steroid withdrawal to those of opioid withdrawal. Although less severe, the signs and symptoms associated with clinical hot flashes, or estrogen deficiency, in the rat parallel those produced by naloxone-precipitated withdrawal in morphine dependent rats, including: 1) an increase in tail skin temperature, 2) a surge in luteinizing hormone and 3) an increase in heart rate. Each of these responses are associated with an increase in sympathetic outflow, which is a current mechanistic hypothesis for hot flashes. As, a corollary, morphine addicted humans show a withdrawal pattern suggesting increased sympathetic outflow and symptoms that include hot flashes. A key feature of animal models, is that they mimic the treatment efficacy observed with the human disease. The morphine withdrawal hot flash model, either in its originally described form, or with the modifications described herein, is responsive to agents typically used in the treatment of human hot flashes. This includes various forms of estrogen (Simpkins et al., 1983; LRL data), clonidine (LRL data), tibolone (LRL data), and medroxyprogesterone (LRL data). Furthermore, the model is sensitive to agents known to be associated with the induction of hot flashes in postmenopausal women.

A modification of the original procedure of Simpkins et al. (1983) is used which employs ovariectomized Sprague-Dawley rats. Animals at 60 days of age (or 200-225 grams) are ovariectomized, and allowed a 14-day rest period to insure surgical recovery and clearance of endogenous ovarian hormones. Administration of a compound of the present invention (po or sc) is initiated on day 14 post-ovariectomy in a volume of 1 ml/kg. Once daily administration of test compound continues through the end of the experiment. On days 15 and 17 post-ovariectomy, the rats are lightly anesthetized with isoflurane and a single 75 mg morphine (free base) pellet is surgically implanted subcutaneously.

On day 21 post-ovariectomy, animals are given ketamine (80 mg/kg; IM) 2-hours after final administration of the test compound. Following induction of the anesthesia, rats are then placed in individual plexiglass cages and temperature sensitive probes are applied to the dorsal side of the tail base. Temperature monitoring is initiated 30 minutes after administration of ketamine and is recorded every 15 seconds for a 1-hr period. To induce morphine withdrawal, 1 mg/kg naloxone is given subcutaneously 15 minutes after start of temperature monitoring. A sharp rise in tail skin temperature typically occurs within 5 minutes post-naloxone injection, and two quantitative endpoints are made: 1) tail skin temperature at 15 min post-naloxone, and 2) area under the temperature response curve for the 45-min post-naloxone measurement period. Following the 1-hour temperature collection period, the animals are sacrificed by decapitation and trunk blood is collected for assessment of serum LH levels (by ELISA). Uteri are also removed at this time, and wet weight recorded.

Representative compounds of formula I were tested at or below 30 mg/kg PO and caused an attenuation of tail skin temperature increase, as measured by temperature change 15 minutes post naloxone injection or AUC over 45 minutes post naloxone administration.

Utilities

As previously stated, the compound of formula I is useful in the treatment of vasomotor symptoms, particularly hot flashes, in a woman, particularly a post-menopausal woman. Typically, the compounds of the present invention are employed in a woman who has suffered at least one vasomotor symptom event. Thus, the compounds of the present invention are most typically employed to reduce the likelihood that the patient will further incur vasomotor symptoms.

Dose

The specific dose administered is determined by the particular circumstances surrounding each situation. These circumstances include, the route of administration, the prior medical history of the recipient, the symptom being treated, the severity of the symptom being treated, and the age of the recipient. The recipient patient's attending physician should determine the therapeutic dose administered in light of the relevant circumstances.

Generally, an effective minimum daily dose of a compound of formula I will exceed about 5 mg. Typically, an effective maximum daily dose will not exceed about 350 mg. The exact dose may be determined, in accordance with the standard practice in the medical arts of "dose titrating" the recipient; that is, initially administering a low dose of the compound, and gradually increasing the dose until the desired therapeutic effect is observed.

We claim:

1. A compound of the formula:

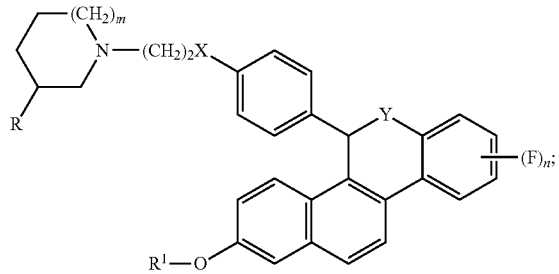

wherein:

m is 0, 1 or 2;

n is 2 wherein the corresponding fluoro moieties are at the 3- and 5-positions;

R is H or methyl provided that if m is 1 or 2, then R must be H and that if m is 0, then R must be methyl;

$R^1$ is H, $SO_2$ (n-$C_4$-$C_6$ alkyl) or $COR^2$;

X is O or $NR^3$;

Y is O, S, SO or $NR^4$;

$R^2$ is $C_1$-$C_6$ alkyl; $C_1$-$C_6$ alkoxy; $NR^5R^{5a}$; phenoxy; or phenyl optionally substituted with halo;

$R^3$ and $R^4$ are independently H or $C_1$-$C_6$ alkyl; and $R^5$ and $R^{5a}$ are independently H, $C_1$-$C_6$ alkyl or phenyl; or a pharmaceutical acid addition salt thereof.

2. The compound of claim 1 wherein m is 1 or 2.

3. The compound of claim 2 wherein $R^1$ is H or $COR^2$ and $R^2$ is $C_1$-$C_4$ alkyl, $NHCH_3$ or phenyl.

4. The compound of claim 3 wherein $R^1$ is H.

5. The compound of claim 4 wherein X is O.

6. The compound of claim 5 wherein m is 1 and Y is O.

7. The compound of claim 5 wherein m is 1 and Y is S.

8. A method for treating hot flash comprising administering to a woman in need thereof an effective amount of a compound of claim 7.

9. A compound of the formula

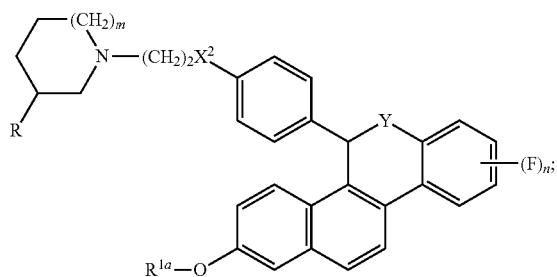

wherein:
m is 0, 1 or 2;
n is 2 wherein the corresponding fluoro moieties are at the 3- and 5-positions;
R is H or methyl provided that if m is 1 or 2, then R must be H and that if m is 0, then R must be methyl;
$R^{1a}$ is H, $SO_2CH_3$, $SO_2$(n-$C_4$-$C_6$ alkyl), $COR^2$, $C_1$-$C_6$ alkyl or benzyl;
$X^2$ is O or $NR^7$;
Y is O, S, SO or $NR^4$;
$R^2$ is $C_1$-$C_6$ alkyl; $C_1$-$C_6$ alkoxy; $NR^5R^{5a}$; phenoxy; or phenyl optionally substituted with halo;
$R^4$ is H or $C_1$-$C_6$ alkyl;
$R^5$ and $R^{5a}$ are independently H, $C_1$-$C_6$ alkyl or phenyl;
$R^7$ is H, $C_1$-$C_6$ alkyl or $CO_2$($C_1$-$C_6$ alkyl); provided that if $R^{1a}$ is H, $SO_2$(n-$C_4$-$C_6$ alkyl) or $COR^2$, then $X^2$ is $NR^7$ and $R^7$ is $CO_2$ ($C_1$-$C_6$ alkyl); or an acid addition salt thereof.

10. The compound of claim 9 wherein m is 1 or 2 and $R^{1a}$ is $SO_2CH_3$, benzyl or methyl.

11. The compound of claim 10 wherein $X^2$ is O.

12. The compound of claim 11 wherein m is 1 and Y is O.

13. The compound of claim 11 wherein m is 1 and Y is S.

14. A compound of the formula:

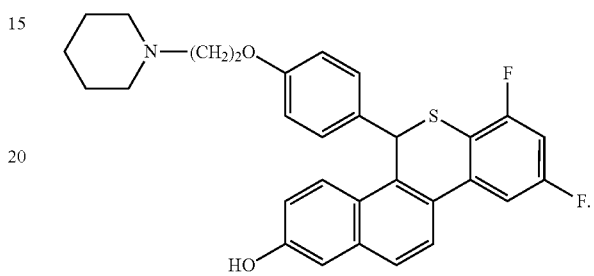

* * * * *